(12) United States Patent
Brust et al.

(10) Patent No.: US 9,171,048 B2
(45) Date of Patent: Oct. 27, 2015

(54) GOAL-BASED CONTENT SELECTION AND DELIVERY

(71) Applicant: Wellclub, LLC, Saint Paul, MN (US)

(72) Inventors: Thomas Edwin Brust, White Bear Lake, MN (US); Phil Kennedy, Eagan, MN (US); Jamal Khan, Redding, CT (US); Jay W. Johnson, Minnetrista, MN (US); Tom Waddell, New Brighton, MN (US)

(73) Assignee: Wellclub, LLC, Saint Paul, MN (US)

( * ) Notice: Subject to any disclaimer, the term of this patent is extended or adjusted under 35 U.S.C. 154(b) by 186 days.

(21) Appl. No.: 13/772,405

(22) Filed: Feb. 21, 2013

(65) Prior Publication Data

US 2014/0157171 A1 Jun. 5, 2014

Related U.S. Application Data

(60) Provisional application No. 61/732,676, filed on Dec. 3, 2012.

(51) Int. Cl.
*G06F 3/048* (2013.01)
*G06F 17/30* (2006.01)
(Continued)

(52) U.S. Cl.
CPC ........ *G06F 17/30554* (2013.01); *G06F 3/0481* (2013.01); *G06F 17/30386* (2013.01); *G06F 17/30598* (2013.01); *G06F 19/363* (2013.01)

(58) Field of Classification Search
CPC ............ G06F 17/30554; G06F 3/0481; G06F 17/30386; G06F 17/30598

USPC .......... 715/771, 758, 759, 753, 760; 705/2, 3; 600/300; 128/920, 921
See application file for complete search history.

(56) References Cited

U.S. PATENT DOCUMENTS

| 4,853,854 A | 8/1989 | Behar et al. |
|---|---|---|
| 5,251,126 A | 10/1993 | Kahn et al. |
| 5,596,994 A | 1/1997 | Bro |

(Continued)

OTHER PUBLICATIONS

"Lift", Powered by Tumblr, [Online]. Retrieved from the Internet: <URL: https://web.archive.org/web/20121116235453/http:/blog.lift.do/, (Nov. 16, 2012), 17 pgs.

(Continued)

*Primary Examiner* — Amy M Levy
(74) *Attorney, Agent, or Firm* — Schwegman Lundberg & Woessner, P.A.

(57) ABSTRACT

Systems and methods for implementing and performing goal-based workflows to assist a human user with achieving a goal or set of goals are described. In one example, a goal-based workflow includes operations for obtaining information from the human user relevant to a goal, performing a psychological and psychological assessment of the human user, selecting and providing goal-based content to the human user, and obtaining and processing a response to the goal-based content from the human user. The operations may be conducted in connection with a subscription or membership to an information service. In further examples, the information service may integrate the content delivery with a social network of "supporter" human users, used to provide encouragement and motivation to the human user for achieving the goal. In other further examples, rewards and adjustments may be provided to the human user based on previous responses to the goal-based content.

20 Claims, 33 Drawing Sheets

(51) Int. Cl.
  *G06F 19/00* (2011.01)
  *G06F 3/0481* (2013.01)

(56) References Cited

U.S. PATENT DOCUMENTS

| | | |
|---|---|---|
| 5,933,136 A | 8/1999 | Brown |
| 6,039,688 A | 3/2000 | Douglas et al. |
| 6,059,724 A | 5/2000 | Campell et al. |
| 6,101,478 A | 8/2000 | Brown |
| 6,144,837 A | 11/2000 | Quy |
| 6,240,394 B1 | 5/2001 | Uecker et al. |
| 6,294,999 B1 | 9/2001 | Yarin et al. |
| 6,381,577 B1 | 4/2002 | Brown |
| 6,547,727 B1 | 4/2003 | Hashiguchi et al. |
| 6,697,783 B1 | 2/2004 | Brinkman et al. |
| 7,216,084 B2 | 5/2007 | Brinkman et al. |
| 7,223,235 B2 | 5/2007 | Brown |
| 7,258,666 B2 | 8/2007 | Brown |
| 7,261,690 B2 | 8/2007 | Teller et al. |
| 7,287,031 B1 | 10/2007 | Karpf et al. |
| 7,297,109 B2 | 11/2007 | Brown |
| 7,299,192 B2 | 11/2007 | Luttrell |
| 7,302,398 B2 | 11/2007 | Ban et al. |
| 7,395,216 B2 | 7/2008 | Rosenfeld et al. |
| 7,412,511 B2 | 8/2008 | Curry |
| 7,478,129 B1* | 1/2009 | Chemtob ............ 709/204 |
| 7,493,264 B1 | 2/2009 | Kelly et al. |
| 7,555,436 B2 | 6/2009 | Brown |
| 7,584,108 B2 | 9/2009 | Brown |
| 7,590,549 B2 | 9/2009 | Brown |
| 7,636,667 B2 | 12/2009 | Brown |
| 7,647,234 B1 | 1/2010 | Ruderman et al. |
| 7,653,556 B2 | 1/2010 | Rovinelli et al. |
| 7,684,999 B2 | 3/2010 | Brown |
| 7,685,000 B1 | 3/2010 | Petit et al. |
| 7,689,437 B1 | 3/2010 | Teller et al. |
| 7,689,440 B2 | 3/2010 | Brown |
| 7,739,124 B1 | 6/2010 | Walker et al. |
| 7,752,056 B2 | 7/2010 | Brown |
| 7,756,722 B2 | 7/2010 | Levine et al. |
| 7,765,112 B2 | 7/2010 | Brown |
| 7,769,600 B2 | 8/2010 | Iliff |
| 7,778,845 B2 | 8/2010 | Brown |
| 7,788,113 B2 | 8/2010 | Fuhrman et al. |
| 7,801,745 B2 | 9/2010 | Walker et al. |
| 7,809,584 B2 | 10/2010 | Morag et al. |
| 7,822,621 B1 | 10/2010 | Chappel |
| 7,822,625 B2 | 10/2010 | Brown |
| 7,827,039 B2 | 11/2010 | Butcher et al. |
| 7,827,040 B2 | 11/2010 | Brown |
| 7,827,042 B2 | 11/2010 | Jung et al. |
| 7,840,420 B2 | 11/2010 | Brown |
| 7,862,506 B2 | 1/2011 | Brown |
| 7,867,165 B2 | 1/2011 | Brown |
| 7,869,852 B2 | 1/2011 | Brown |
| 7,870,249 B2 | 1/2011 | Brown |
| 7,871,376 B2 | 1/2011 | Brown |
| 7,877,274 B2 | 1/2011 | Brown |
| 7,877,276 B2 | 1/2011 | Brown |
| 7,890,346 B2 | 2/2011 | Padron et al. |
| 7,904,530 B2 | 3/2011 | Partridge et al. |
| 7,921,186 B2 | 4/2011 | Brown |
| 7,925,522 B2 | 4/2011 | Brown |
| 7,941,323 B2 | 5/2011 | Brown |
| 7,941,326 B2 | 5/2011 | Brown |
| 7,941,327 B2 | 5/2011 | Brown |
| 7,944,342 B2 | 5/2011 | Sekura |
| 7,944,448 B2 | 5/2011 | Iwamura et al. |
| 7,945,461 B2 | 5/2011 | Sekura |
| 7,955,219 B2 | 6/2011 | Birrell et al. |
| 7,970,620 B2 | 6/2011 | Brown |
| 7,972,247 B2 | 7/2011 | Daikeler et al. |
| 7,979,284 B2 | 7/2011 | Brown |
| 7,985,164 B2 | 7/2011 | Ashby |
| 7,993,267 B2 | 8/2011 | Iliff |
| 8,013,736 B2 | 9/2011 | Derrick et al. |
| 8,015,025 B2 | 9/2011 | Brown |
| 8,015,030 B2 | 9/2011 | Brown |
| 8,015,033 B2 | 9/2011 | Brown |
| 8,015,138 B2 | 9/2011 | Illiff |
| 8,019,618 B2 | 9/2011 | Brown |
| 8,024,201 B2 | 9/2011 | Brown |
| 8,032,399 B2 | 10/2011 | Brown |
| 8,034,294 B1 | 10/2011 | Goldberg |
| 8,036,912 B2 | 10/2011 | Jensen et al. |
| 8,038,577 B2 | 10/2011 | McIntosh |
| 8,055,516 B2 | 11/2011 | Iliff |
| 8,066,514 B2 | 11/2011 | Clarke |
| 8,069,131 B1 | 11/2011 | Luechtefeld et al. |
| 8,073,707 B2 | 12/2011 | Teller et al. |
| 8,075,451 B2 | 12/2011 | Dugan |
| 8,078,492 B2 | 12/2011 | Brown et al. |
| 8,095,522 B2 | 1/2012 | Welti et al. |
| 8,100,757 B2 | 1/2012 | Melendez |
| 8,108,226 B2 | 1/2012 | Barrett |
| 8,109,874 B2 | 2/2012 | Kong et al. |
| 8,131,570 B2 | 3/2012 | Levin et al. |
| 8,140,663 B2 | 3/2012 | Brown |
| 8,160,901 B2 | 4/2012 | Heywood et al. |
| 8,165,893 B1 | 4/2012 | Goldberg et al. |
| 8,170,807 B2 | 5/2012 | Barnett et al. |
| 8,180,592 B2 | 5/2012 | Yuen et al. |
| 8,182,267 B2 | 5/2012 | Katz et al. |
| 8,182,424 B2 | 5/2012 | Heckerman |
| 8,202,202 B2 | 6/2012 | McGlynn et al. |
| 8,234,127 B2 | 7/2012 | Naik et al. |
| 8,277,377 B2 | 10/2012 | Quy |
| 9,037,578 B2 | 5/2015 | Brust et al. |
| 2001/0027403 A1 | 10/2001 | Peterson et al. |
| 2001/0039503 A1 | 11/2001 | Chan et al. |
| 2002/0026333 A1 | 2/2002 | Endou |
| 2002/0055857 A1 | 5/2002 | Mault |
| 2002/0055859 A1 | 5/2002 | Goodman et al. |
| 2002/0072932 A1 | 6/2002 | Swamy |
| 2002/0087358 A1 | 7/2002 | Gilbert |
| 2002/0128861 A1 | 9/2002 | Lan et al. |
| 2002/0133377 A1 | 9/2002 | Brown |
| 2002/0183598 A1 | 12/2002 | Teraura et al. |
| 2002/0184056 A1 | 12/2002 | Tsuboi et al. |
| 2003/0014279 A1 | 1/2003 | Roman et al. |
| 2003/0061065 A1 | 3/2003 | Keeley |
| 2003/0061215 A1 | 3/2003 | Messina |
| 2003/0065561 A1 | 4/2003 | Brown et al. |
| 2003/0101076 A1 | 5/2003 | Zaleski |
| 2003/0182161 A1 | 9/2003 | Vanderlei et al. |
| 2004/0131997 A1 | 7/2004 | McGuire et al. |
| 2004/0176666 A1 | 9/2004 | Chait |
| 2004/0242973 A1 | 12/2004 | Tanabe et al. |
| 2004/0243443 A1 | 12/2004 | Asano et al. |
| 2005/0095628 A1* | 5/2005 | Krempin et al. ............ 435/6 |
| 2005/0113650 A1* | 5/2005 | Pacione et al. ............ 600/300 |
| 2005/0117527 A1 | 6/2005 | Williams et al. |
| 2005/0240434 A1 | 10/2005 | Wooten et al. |
| 2005/0240438 A1 | 10/2005 | Day |
| 2005/0240444 A1 | 10/2005 | Wooten et al. |
| 2005/0283385 A1 | 12/2005 | Hunkeler et al. |
| 2005/0283386 A1 | 12/2005 | Powers et al. |
| 2006/0004611 A1 | 1/2006 | Brown |
| 2006/0010014 A1 | 1/2006 | Brown |
| 2006/0026036 A1 | 2/2006 | Mahmood |
| 2006/0064322 A1 | 3/2006 | Mascarenhas et al. |
| 2006/0189853 A1 | 8/2006 | Brown |
| 2006/0224416 A1 | 10/2006 | Lloyd et al. |
| 2006/0235722 A1 | 10/2006 | Brown |
| 2007/0005395 A1 | 1/2007 | Singh |
| 2007/0016446 A1 | 1/2007 | Brown |
| 2007/0021984 A1 | 1/2007 | Brown |
| 2007/0061167 A1 | 3/2007 | Brown |
| 2007/0100595 A1 | 5/2007 | Earles et al. |
| 2007/0190501 A1 | 8/2007 | Brown |
| 2007/0260511 A1 | 11/2007 | Bender, II |
| 2007/0282842 A1 | 12/2007 | Messinaq |
| 2008/0004902 A1* | 1/2008 | Leong-Fern et al. ............ 705/2 |
| 2008/0103814 A1 | 5/2008 | Fabius et al. |

(56) References Cited

U.S. PATENT DOCUMENTS

| | | | |
|---|---|---|---|
| 2008/0103855 A1 | 5/2008 | Hernandez et al. | |
| 2008/0124689 A1 | 5/2008 | Williams et al. | |
| 2008/0126276 A1 | 5/2008 | Williams et al. | |
| 2008/0126277 A1 | 5/2008 | Williams et al. | |
| 2008/0140449 A1 | 6/2008 | Hayes | |
| 2008/0162352 A1* | 7/2008 | Gizewski | 705/50 |
| 2008/0168032 A1 | 7/2008 | Criou et al. | |
| 2008/0172246 A1 | 7/2008 | Larkin | |
| 2008/0183757 A1 | 7/2008 | Dorogusker et al. | |
| 2008/0243543 A1 | 10/2008 | Jung | |
| 2008/0287748 A1 | 11/2008 | Sapounas et al. | |
| 2008/0318678 A1* | 12/2008 | Stivoric et al. | 463/36 |
| 2009/0030732 A1 | 1/2009 | Jung | |
| 2009/0043613 A1 | 2/2009 | Jung | |
| 2009/0069643 A1 | 3/2009 | Quy | |
| 2009/0070141 A1 | 3/2009 | Jolley | |
| 2009/0112617 A1 | 4/2009 | Jung et al. | |
| 2009/0118593 A1 | 5/2009 | Jung | |
| 2009/0119154 A1 | 5/2009 | Jung | |
| 2009/0132275 A1 | 5/2009 | Jung et al. | |
| 2009/0199230 A1 | 8/2009 | Kumar et al. | |
| 2009/0312668 A1 | 12/2009 | Leuthardt et al. | |
| 2010/0063833 A1 | 3/2010 | Mahoney | |
| 2010/0150384 A1 | 6/2010 | Waldmann | |
| 2010/0250497 A1 | 9/2010 | Redlich et al. | |
| 2011/0172497 A1* | 7/2011 | Ruby et al. | 600/300 |
| 2011/0209037 A1 | 8/2011 | Yoon et al. | |
| 2012/0011139 A1 | 1/2012 | Drissi et al. | |
| 2012/0221345 A1* | 8/2012 | McClure et al. | 705/2 |
| 2012/0272278 A1 | 10/2012 | Bedi | |
| 2013/0124218 A1 | 5/2013 | Masloski et al. | |
| 2014/0100955 A1 | 4/2014 | Osotio et al. | |
| 2014/0156308 A1* | 6/2014 | Ohnemus et al. | 705/3 |
| 2014/0156645 A1 | 6/2014 | Brust et al. | |
| 2014/0156646 A1 | 6/2014 | Brust et al. | |
| 2014/0156676 A1 | 6/2014 | Brust et al. | |

OTHER PUBLICATIONS

"U.S. Appl. No. 13/772,697, Examiner Interview Summary mailed Dec. 17, 2014", 3 pgs.

"U.S. Appl. No. 13/772,697, Non Final Office Action mailed Sep. 3, 2014", 12 pgs.

"U.S. Appl. No. 13/772,697, Notice of Allowance mailed Jan. 20, 2015", 7 pgs.

"U.S. Appl. No. 13/772,697, Response filed Dec. 23, 2014 to Non Final Office Action mailed Sep. 3, 2014", 16 pgs.

"U.S. Appl. No. 13/801,048, Examiner Interview Summary mailed Mar. 27, 2015", 3 pgs.

"U.S. Appl. No. 13/801,048, Non Final Office Action mailed Nov. 25, 2014", 8 pgs.

"U.S. Appl. No. 13/801,048, Response filed Mar. 25, 2015 to Non Final Office Action mailed Nov. 25, 2014", 15 pgs.

"U.S. Appl. No. 13/801,315, Non Final Office Action mailed Apr. 6, 2015", 20 pgs.

* cited by examiner

GOAL-BASED CONTENT SELECTION AND DELIVERY

CROSS-REFERENCE TO RELATED APPLICATIONS

This application claims priority under 35 U.S.C. §119(e) to U.S. Provisional Patent Application Ser. No. 61/732,676, filed Dec. 3, 2012, which is incorporated herein by reference in its entirety.

TECHNICAL FIELD

Embodiments pertain to techniques and systems for content selection and management. Some embodiments relate to workflows in an information system to select, suggest, recommend, and deliver content to particular human subjects based on an environmental goal or set of goals.

BACKGROUND

Various data services select or recommend content for display to users. For example, in the self-help setting, a variety of data services provide tips, recommendations, and focused content to assist a subject human user with goal-based outcomes such as exercise goals, weight loss, smoking cessation, medical therapy, and the like. Some of these data services provide recommended content to a user in response to user-indicated preferences, user-indicated activity history, or manual user requests for content. Other data services rely on an expert human user to determine which content is most appropriate for delivery to the subject human user to achieve a goal-based outcome.

To the extent that existing data services provide automated recommendations or selections of content, the timing, delivery, and substance of content from these data services is determined by complex predetermined rules and attributes, or other selections influenced by manual human intervention. For example, recommendations may be hard-coded in a content delivery system to deliver suggestive content at scheduled intervals, or in response to the user's manual indications that a certain accomplishment has or has not been reached. Existing systems and techniques do not provide real-time recommendations and content selections without extensive programming or oversight. Further, the workflows involved with existing content delivery systems call for extensive human selection and specification of content, and are not fully automated, responsive, or adaptive to user needs.

DETAILED DESCRIPTION

Figure 1:
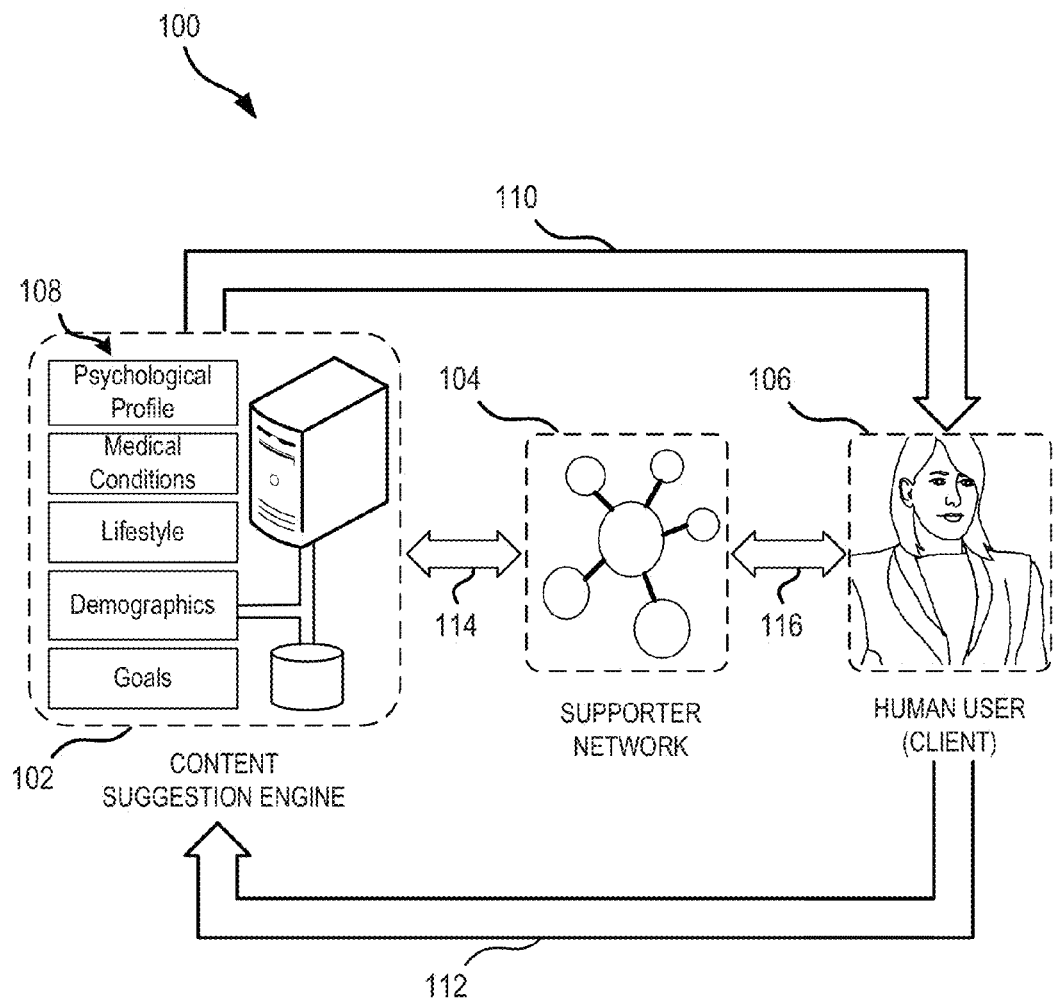
FIG. 1 illustrates an information flow diagram of interaction with an example information system and a content suggestion engine according to an example described herein.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

The present disclosure illustrates various techniques and configurations to enable a series of dynamic workflows for the selection and presentation of content from an information system relevant to goal-based activities of a human user. The dynamic workflows described herein enable the integration of user interfaces and user communication platforms to achieve relevant and timely communication among users, to encourage progress and achievement of the goal and related actions. The dynamic workflows described herein further may be integrated with social networks and portable communication mediums, to provide additional availability and delivery of content to users in a variety of settings.

In one example, an internet-hosted information service is offered to users through a series of dynamically changing user interfaces. For example, widgets hosted in an interactive webpage or software application may be used to collect, display, and deliver relevant and timely communication, suggestions, and content to and from a user. The information service may be used to directly interact and implement aspects of a goal-based workflow with a subject human user, while also facilitating interaction during the goal achievement with other humans or agents, such as supporters, experts, professionals, and the like.

The goal-based workflows may integrate with various evaluations that dynamically assess a user's current state and receptivity to achieving an action or goal. For example, user interaction from a series of evaluations may be collected to monitor and measure a user's personality, goals, likes, and demographics, and used as feedback to facilitate real-time, full-duplex interaction with the client. This user interaction may be used to set, adjust, and achieve moving goals in a continuous automated feedback loop to constantly provide the needed mutually agreed upon behavior suggestions and actions needed to accomplish an overall goal or smaller actions that provided progress towards the overall goal.

The goal-based workflows may be exposed through a series of user interfaces that involve social aspects and communications. For example, various circles of personal influence in a connected group (e.g., trusted sets of friends) may be leveraged to keep a user motivated to achieve lifestyle improvements in a fun and inviting manner. The interactions may be integrated with features of a social network and social network communications to engage supports of friends and professionals to publicly or privately encourage a user to accomplish various activities and achieve goals. A series of scripted or self-generated directives, "destinations", and action playlists may also be used to direct a client onto the path of incremental improvements towards achievement of an ultimate goal.

In further examples of a goal-based workflow, the workflow may integrate an automated routine involving a series of "check-in" communications with a human subject. For example, the human subject may be queried with a series of episodic questions that trigger other responses from the information system. The responses to the episodic questions (or the lack of responses to the episodic questions) may trigger conditions in the information system. For example, failure to perform any requested actions a certain number of times in a row, such as three times in a row, may trigger a condition to alert connected users in the supporter network and produce relevant follow-up content.

In another further example of a workflow, behavior conditioning techniques may be implemented through interaction with a virtual health game or like virtual activities. The virtual health game and the achievement of various virtual and real-life goals may result in tangible rewards provided to the client. The activities and rewards occurring from the virtual health game may be provided into corresponding communications with the supporter network, for example as various accomplishments in the virtual health game are posted and communicated to the supporter network. In some examples, the tangible rewards may be donated on behalf of the human user to charitable organizations, thus encouraging the client to perform an action and achieve a goal that is not only beneficial for the client, but also beneficial to other individuals not directly connected with the action.

Information System Configuration

The dynamic workflows and the various interaction widgets and applications described by the present disclosure may be configured for receipt, processing, and delivery of relevant content from an electronic information system. The information system, as further described herein, may implement human interaction with a series of goal-based workflows and goal-based processing activities that deliver relevant content to encourage human activity and progress towards an ultimate goal. Relevant content may be provided in a push or pull manner, on schedule or in response to determined conditions, and manually or automatically from the information system, in accordance with the following techniques.

The computing systems and platforms encompassed by the present disclosure include a mobile or web-based social networking information service, interacting with a suggestion engine, that is used to motivate the human user to change behavior (such as healthy lifestyle choices and activities that are likely to lead to a positive health outcome) through a persistent intelligent coaching model. The information service may provide intelligent decision making and reinforcement of certain content and content actions, to facilitate encouragement or motivation that increases the likelihood of change in human behavior to achieve the goal. In particular, the information service focuses on encouraging a human user to complete a series of discrete, separate actions or activities (small goals) that in combination will help achieve a larger overall goal. For example, in a weight loss setting, this may include a series of tens, hundreds, or thousands of discrete diet and exercise actions that in combination will help the human user achieve a weight loss goal.

In conjunction with operations of the suggestion engine, the information service may adapt to learn a user's behavior patterns and offer personalized, relevant, or timely suggestions, motivations, or other directed content to help the human user achieve the goal. The information service also may enable peer and professional support for a human user by creating and maintaining human connections relevant to the goal, such as through establishing social networking connections and social networking interactions customized to the goal. As the social network or the behaviors of the human user change, the information service may adapt to alter the actions, motivations, or other directed content to remain relevant, personal, or timely to the human user. In this fashion, the information service is intended to cause behavior changes of the human users, through promotion to achieve the user's goals with social encouragement by friends, family, or team members (supporters), personal motivations reinforced with reminders, or new structures in their living environment, such as may be helpful in altering habits to achieve the goal.

The information service may include various applications and corresponding user interfaces to be viewed by the human user and supporters of the human user to encourage beneficial interactions between the human user and the supporters. These interactions, which may be driven by suggested content and suggested content delivery types or timings, are used to cause activities that lead to the intended behavior change(s) in a human user. Accordingly, the content suggestion engine acts in a larger environment of an "intelligent" information system that provides appropriate messages and content selections to the human user and supporters at the right time.

FIG. 1 illustrates an information flow diagram of interaction with an example information system 100 configured for providing content (e.g., motivations, recommendations, suggestions, facts, or other relevant material) to human users. The information system 100 may include a suggestion engine 102, participation from a supporter network 104 of various human or automated users, and participation from a subject human user (further referred to herein as a "client") 106.

The suggestion engine 102 may be configured to make decisions to deliver relevant content dynamically (e.g., at the proper time, in the proper context, and with the proper communication medium) using data conditions 108 maintained for the client 106. The data conditions 108 maintained for the client 106 may include information such as: one or more goals of the client 106; demographic information such as gender, age, and familial information; medical information such as medical conditions, medical history, and medical or physical restrictions; a psychological profile and other psychological information such as personality type, daily routines or habits, emotional status, likes and dislikes; and available external devices (e.g., smart phone or smart phone applications, smart weight scales, smart TV, video game systems, etc.); client-desired coaching programs and models (e.g., diet style, exercise focus, or mental health); information relevant to discrete activities, such as present or scheduled locations of the client 106, and time to accomplish activities; information relevant to the goal, such as time to achieve the goal, difficulty of achieving the goal; and like information for conditions relevant to the human user, supporters of the human user, or the overall goal.

The specific content selection operations of the suggestion engine 102 are directed to change the behavior of the client 106, such as to help the client 106 achieve a defined or derived goal with a series of content messages that invoke action by suggested activities and events. Delivery of the content may be provided directly from the suggestion engine 102 to the client 106 with a content delivery flow 110. With the content delivery flow 110, the suggestion engine 102 may query the client 106, such as by periodically or randomly querying, to gain information and feedback that may affect what content is delivered to the client 106. Responses by the client 106 may be provided back to the content suggestion engine 102 through a content feedback flow 112 to indicate the results of such querying or feedback.

The suggestion engine 102 may also provide indirect content delivery flows 114, 116 through a supporter network, to enable the supporter network 104 to provide content to the client 106 at appropriate times. Specifically, the suggestion engine 102 may indirectly provide content selections to the client 106 using indirect content delivery flow 114, and orchestrate resources of the supporter network 104 by engaging influential persons (e.g., family, friends, or others that influence the client 106) to forward or deliver the content.

The supporter network 104 may also facilitate interaction from healthcare providers or other professionals (e.g., nutritionists, personal trainers, psychologists, or behavior coaches, among others). Such interaction from the supporter network 104 may be used to proactively guide personalized and critically timed suggestions (e.g., such as by sending a message to the client 106 that encourages a specific activity), or persistently coaching, guiding, motivating, or focusing the client 106 to complete actions to achieve their goal.

Additionally, members of the supporter network 104 may generate and provide suggestions back to the suggestion engine 102, directly or with crowdsourcing-type mechanisms distributed among a plurality of persons. For example, a supporter may directly author suggestions that are sent to the human user, or edit, modify, or unify suggestions with slight modifications for user with human users. Based on the effectiveness of the content created by the supporter network 104, a pool of suggestions may be created.

Thus, the supporter network 104 may be used to generate or forward content selected by the suggestion engine 102, using indirect content delivery flow 116. For example, the suggestion engine 102 may provide a supporter of the supporter network 104 with pre-formatted action content that may be sent directly from the supporter to the client 106 using a recognized communication medium, such as by forwarding and customizing a text message, an email message, a social network message, and the like. Suggestions directly received from members of the supporter network 104 are more likely to reduce barriers or excuses and empower the client 106 to take action that will help achieve their goals. Feedback may also be provided back to members of the supporter network 104 from the client 106 (such as a confirmation that the client 106 performed the activity, a message that the client 106 enjoyed the suggestion, a message asking for support to perform the activity, and the like).

The suggestion engine 102 may communicate with the supporter network 104 and the client 106, such as to obtain information about the client 106 or provide messages to the client 106 or to the supporter network 104. The supporter network 104 may personalize the message and send it to the client 106, such as shown in FIG. 1. By having the client 106 receive the message from the supporter network 104 the message may have more impact, and potentially be more motivating, than if it came directly from the suggestion engine 102.

Suggestion Content Types and Delivery

Appropriate messages, multimedia, and other content delivered to the client 106 from or on behalf of the information system 100 are referred to herein as "suggestion content," as may be selected and produced by the content suggestion engine 102. Suggestion content may include content from one or more messages that the client 106 and supporter network 104 receive that are collectively intended to cause human attention and cause the client 106 to perform some action. The suggestion content may be tailored and customized to be appropriate to the client 106, time, and individual intended actions. The suggestion content may include a variety of formats, such as content that indicates greetings, actions, motivations, prompts, reminders, and rewards. Further, the suggestion content may be delivered and interacted with according to particular goal-based workflows or rule sets.

As used herein, suggestion content may include content delivered to the client 106 intended to cause an action related to an ultimate goal. Suggested action content sent to the client 106, may be constructed from content that includes an action statement, and a pre statement or a post statement.

As used herein, motivational content is a specific subset of suggestion content that is intended to improve the likelihood of the client 106 performing a suggested action by appealing to some human interest. Motivational content may be embodied by: various prompts that include a request of the client 106 or supporter network 104 for a response; reminders that include a statement that reminds the client 106 or a supporter from the supporter network 104 that an action on their part is due; rewards that include statements provided to the client 106 or supporter that are congratulatory or explain something being given to the client 106 or supporter; supporter messages that include content specifically intended for the supporter.

Content provided by the information system 100 may be stored and maintained in structured and unstructured form. Unstructured content may include suggestion content not yet edited, tagged, or final reviewed; whereas structured content may include content that has been edited, tagged, and reviewed, and is ready for use by the suggestion engine 102 (as further illustrated with reference below to FIGS. 2A and 2B).

Content may be tagged for use in defined retrieval operations. Such tagging may include a psychological assessment matching. A client 106 may be asked to take assessments for engagement, receptivity, or social style. The content may be tagged in such a way that the information system 100 matches the client 106 with the style of the content suited for them. This may "personalize" the interactions between the information system 100 and the client 106, such as to provide a more effective or engaging environment. The information system 100 may provide content for each of eating, movement (e.g., actions to physically accomplish), and self-view. The tags may provide this information.

The tagging of data may include "behavior change" tagging. A current behavior change theory promotes a combination of "sources of behavior change" that promote a higher probability of changing people's behavior. These sources of behavior change include items that improve an individual's intrinsic/extrinsic motivation and aptitude, group factors and power to cause behavior change, and environmental factors and power to cause behavior change. Presenting suggestions that fit in multiple behavior change areas may be more effective than presenting suggestions in just one or a few of the areas. Additionally, the client 106 may fill out a lifestyle questionnaire, which determines, such as by using Boolean logic, different "problems" that the client 106 may have. Content may be tagged with these problems, such as to tag content that relates to the problem. The client 106 may work on the problem by choosing specific suggestions or playlists tagged with that problem.

In one example use of a suggestion engine 102, the client 106 is the person that the information system 100 is intended to help; the supporter network 104 may include one of the persons providing aid to the client 106—this person could be a team member, friend, family member, or paid supporter such as personal trainer, among others. Thus, overall users of the suggestion engine 102 may include any person using the information service (and accompanying applications, websites, and services), including the client 106, supporters in the supporter network 104, an administrator, and the like.

The information system 100 facilitates interaction with the client 106 and supporters in the supporter network 104, such as encouraging clients and supporters to interact in the social network, to accompany several types of content. Content may be created that gives clients and supporters specific actions to do, and this content may be delivered in a way that encourages the supporter or client 106 to do the action. The content may be designed to be delivered to the client 106 either directly or through the supporter. A plurality of action statements providing respective suggested actions may be presented to the client 106 for participation. Other types of content may be used to increase the probability of the client 106 performing the suggested actions.

Figure 2A:
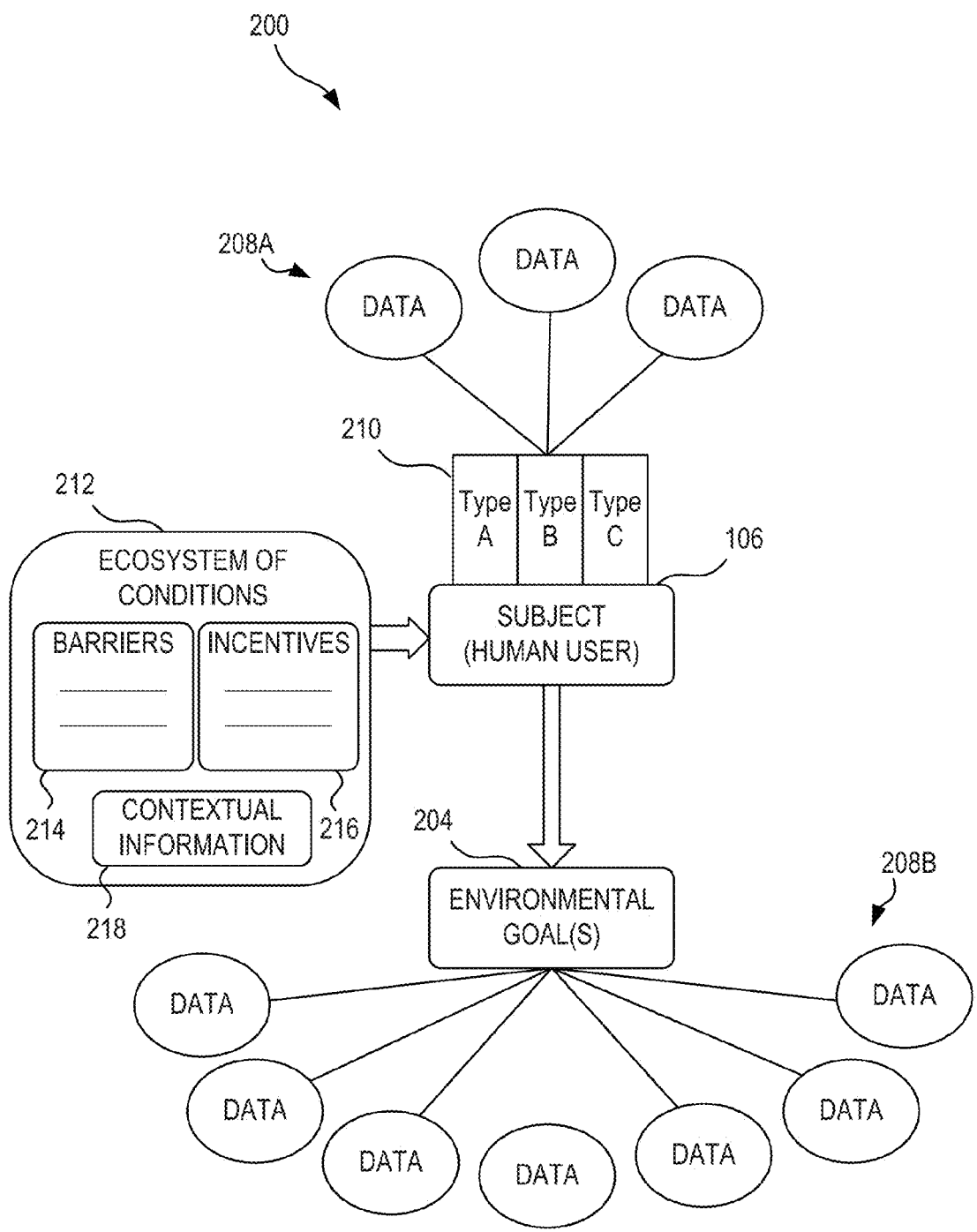
FIG. 2A illustrates an information flow diagram of data operations for factoring activities relevant to an environmental goal according to an example described herein.

FIG. 2A illustrates an information flow diagram of an example of data operations 200 of the suggestion engine 102. Data 208A and 208B, illustrated as various inputs, may be provided in a structured format. Structured data in one example is unstructured data that has undergone a formalization, structuring, categorization, and tagging process in the information system 100 illustrated in FIG. 1. The data operations 200 serve to map data 208A to a personality or behavior type 210 or characteristic of a human user such as the client 106, and an ecosystem of conditions 212 is factored to produce appropriate data 208B that addresses one or more environmental goals 204.

Data input for operations 200 of the suggestion engine 102 may originate from a variety of data sets and data types, but not all data types and data inputs may impact a human subject to attain a particular goal at a particular time. Data 208A may be provided from client personal data, such as location, the psychological state, lifestyle, occupation, relationship status, or coaching style, among others, collected or determined for the client 106. A client's behavior type 210, such as caregiver, colleague, competitor, authoritarian, optimist, skeptic, fatalist, activist, driver, analytical, amiable, expressive, or combinations thereof, may be inferred or otherwise determined from the data 208A (and changed or adapted as appropriate using contextual user information 218 or data 208B).

An ecosystem of conditions 212, including barriers 214 to and incentives 216 for achieving the one or more environmental goals 204 may be determined. The ecosystem of conditions 212 generally reflects information items that the information system 100 is aware of, and relevant factors to achieve success. This may include data such as the time of day, client location, medical records of the client 106, and like information or conditions that affect the client 106.

Barriers 214 considered with the ecosystem of conditions 212 may include the client 106 having a physical ailment, such as a bad knee or asthma, not having a phone, not having supporters, does not like working out, cannot afford the services, having a busy schedule, medical conditions (such as allergies or taking medications), among others. Incentives 216 considered with the ecosystem of conditions 212 may include things that the client 106 likes (e.g., brand name shoes or specific music), peer pressure, a good feeling gained from performing some activity (e.g., working out), a discount on goods or services provided, or an upcoming event (e.g., a half marathon). The data 208A, 208B and the ecosystem of conditions 212 may be determined through obtaining answers to questions, such as through answers to episodic questions posed to the client 106 (the episodic questions resulting at determined times, places, or contexts). The ecosystem of conditions 212 further may provide contextual user information 218 to provide additional data to help interpret or understand the barriers 214, incentives 216, or the data 208A, 208B.

The data 208B may be directly or indirectly related to the one or more environmental goals 204. The data 208B may include a reward for achieving the goal(s) 204 (e.g., kudos), a type of diet to be followed, a reason for wanting to achieve the goal, or a date to achieve the goal by, among others. The environmental goal(s) 204 may include physical activity goals, such as to lose a certain amount of weight, change a habit, such as to quit smoking, biting fingernails, workout a specific number of times in a period of time, or to achieve a physical challenge such as running a marathon or climbing a mountain, among others.

The one or more environmental goals 204 are not necessarily limited to a central, ultimate goal (such as losing weight, or stopping smoking), but may include a number of subordinate or associated goals (such as developing healthy habits, a positive self-image, or confidence or enjoyment of the goal-reaching process) that help achieve the ultimate goal in a positive fashion. Thus, the environmental goals 204 may be broader than a single goal and may include a number of additive, complimentary, or interrelated actions and results that produce beneficial outcomes and experiences for the client 106.

Different humans have preferred ways of being talked to and interacted with. The information system 100 may facilitate the client 106 taking several questionnaires that show these preferences. A personality style may be inferred or determined from answers to questions in the questionnaires. The personality styles may indicate a client's receptivity (e.g., the preference for a certain tone of message); engagement (e.g., a bias towards immediate action versus thoughtful consideration when presented with a challenge to change); or social style (e.g., an intersection of assertiveness and responsiveness). The content may be designed to fulfill all these preferences.

Figure 2B:
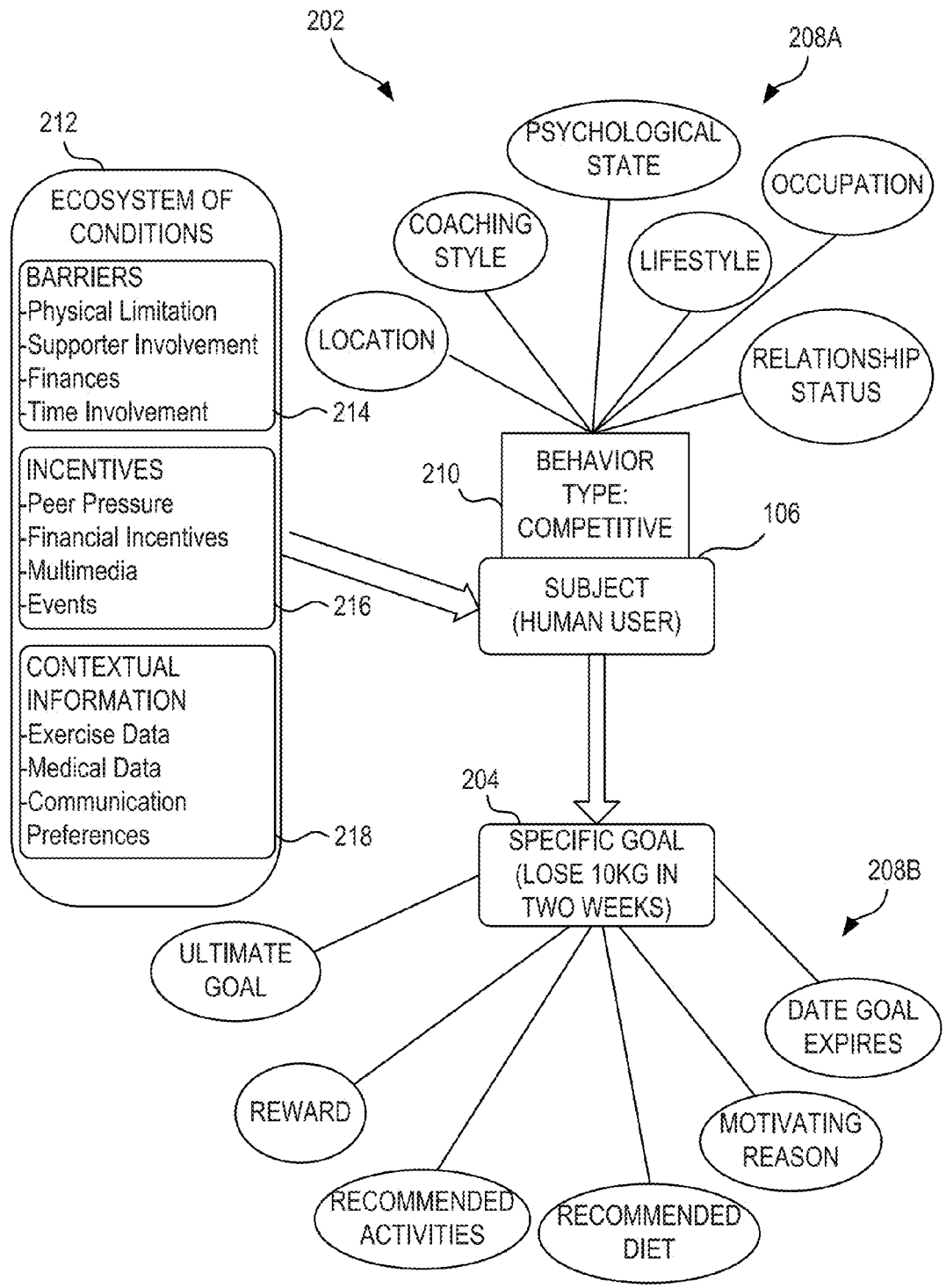
FIG. 2B illustrates an information flow diagram of data operations for factoring activities relevant to a specific physiological goal according to an example described herein.

FIG. 2B provides an illustration of an information flow diagram of an example of data operations 202 of the suggestion engine 102 applied to a specific weight loss goal 204 (e.g., to lose 10 kilograms in two weeks). In particular, the data operations 202 illustrate the association of specific data points 208A with the client 106 and the client's behavior type 210, the association of specific data points 208B with a specific goal 204, and the provision of an ecosystem of conditions 212 that affect the client 106.

As illustrated in FIG. 2B, some of the specific data points 208A associated with the client 106 and the client's behavior type 210 might include data related to: the client's location; the client's preferred coaching style; the client's current or historical psychological state; the client's lifestyle; the client's occupation; or the client's relationship status. As shown, the client's behavior type 210 is classified as "competitive", which may serve to filter or weight usage for some of the data points 208A.

As also illustrated in FIG. 2B, some of the conditions that affect the client 106 include various barriers, incentives, and contextual information data points. The data points relevant to the client 106 may include barriers such as physical limitations; limitations on supporter involvement; limited finances; or limited time involvement. The data points relevant to the client 106 may also include incentives such as peer pressure; financial incentives; multimedia (e.g., a favorite song); and events and enjoyable activities. The data points relevant to the client 106 may also be contextual user information 218 such as exercise data (such as data provided from physiological monitoring device); medical data (such as provided from a medical device, a psychological monitoring device, or medical records); and communication preferences (to accomplish more effective communications). Each of these conditions may provide further classifications and conditions. For example, communication preferences may be established not just for the type of communications, but also for the particular sender (because some clients may be more receptive to communications from particular people).

As also illustrated in FIG. 2B, some of the specific data points associated with the specific weight loss goal 204 might include data related to: the ultimate goal; reward status or reward history; recommended activities and history of progress toward recommended activities; recommended diet and history of progress toward recommended diet; motivating reason(s); and timeliness such as the date that the goal expires.

The content and goal-based workflows delivered from the information system 100 may not only be customized to the specific goal or the ultimate goal, but may also be customized to the personality style, barriers, incentives, contextual information, behavior type, and preferences of the client 106. Each of the various data values maintained in the ecosystem of conditions 212 and the data points 208A, 208B may serve to direct the content, timing, availability, and communication methods of the goal-based workflows and workflow results.

Series-Based Goal Actions

Figure 3:
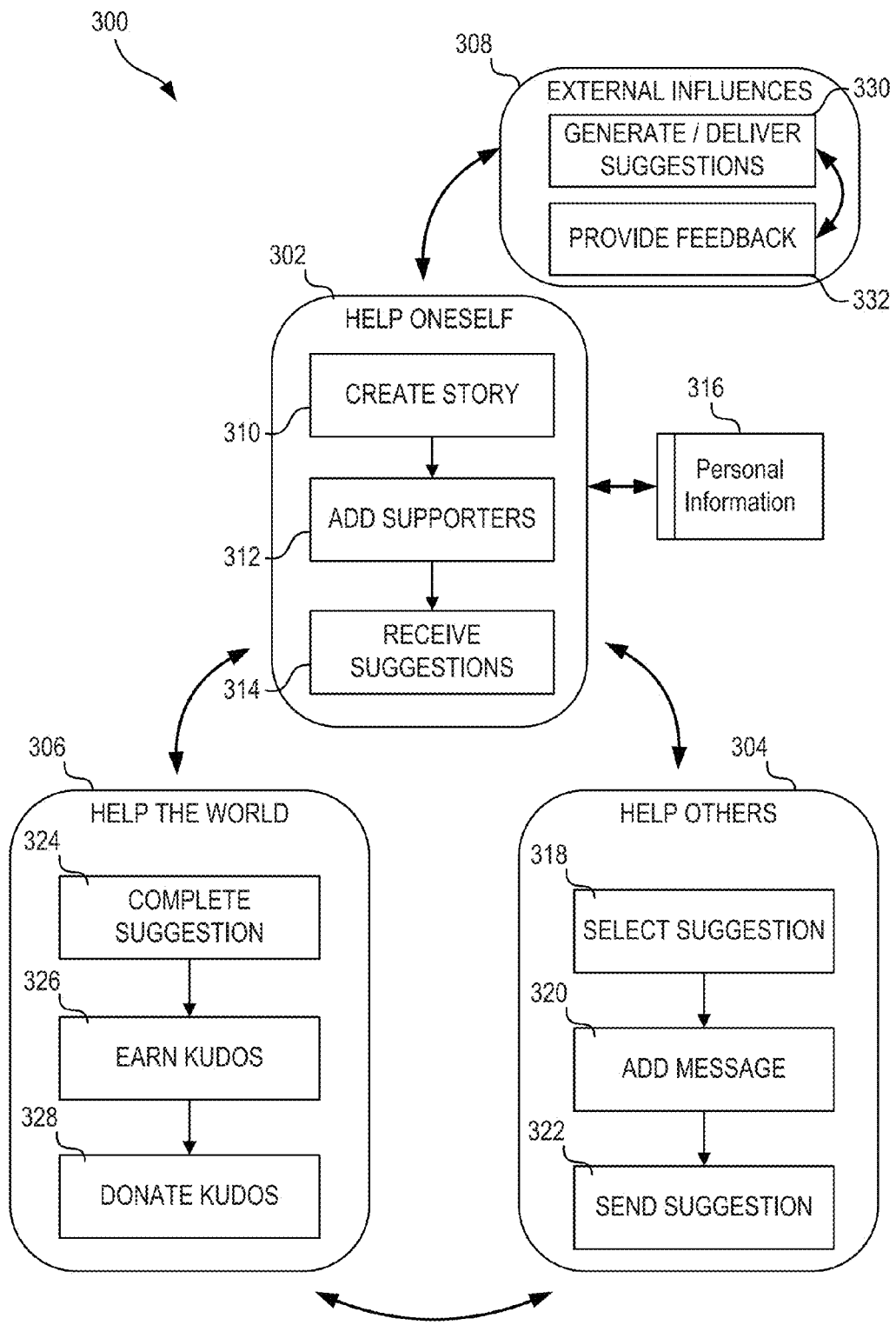
FIG. 3 illustrates an overview of goal-based workflows integrated with an information system according to an example described herein.

FIG. 3 provides an illustration of a framework 300 for a series of integrated goal-based workflows according to examples described herein. Within the framework 300 a user can help oneself (operation 302), help others within the system (operation 304), or can help others outside the system—help the world (operation 306). These and other aspects of the user's activity may also be affected by outside/external influences (operation 308). Helping oneself may include creating a story (operation 310), adding supporters (operation 312), and receiving suggestions (operation 314) from other users, such as supporters. Creating a story (operation 310) may include indicating or otherwise providing personal information (data 316). Personal information (data 316) may include likes and dislikes, demographic information, medical conditions, goals, lifestyle, or a psychological profile, among others. Helping others may include selecting a suggestion (operation 318), adding a message to the suggestion (operation 320), and sending the suggestion to the user (operation 322). The suggestion can be an encouraging message or some other form or personalizing the suggestion to the user. Helping the world may include a user completing a suggestion (operation 324), earning kudos (operation 326) (a reward currency) for completing the suggestion, and donating the kudos (operation 328) to a charity or other altruistic destination. The interaction between the user activity (such as helping oneself (operation 302)) and the receipt of external influences (operation 308) may include various suggestions generated or delivered by one or more third parties (operation 330) and the one or more third parties providing feedback (operation 332) to improve operation of the information system 100.

Figure 4A:
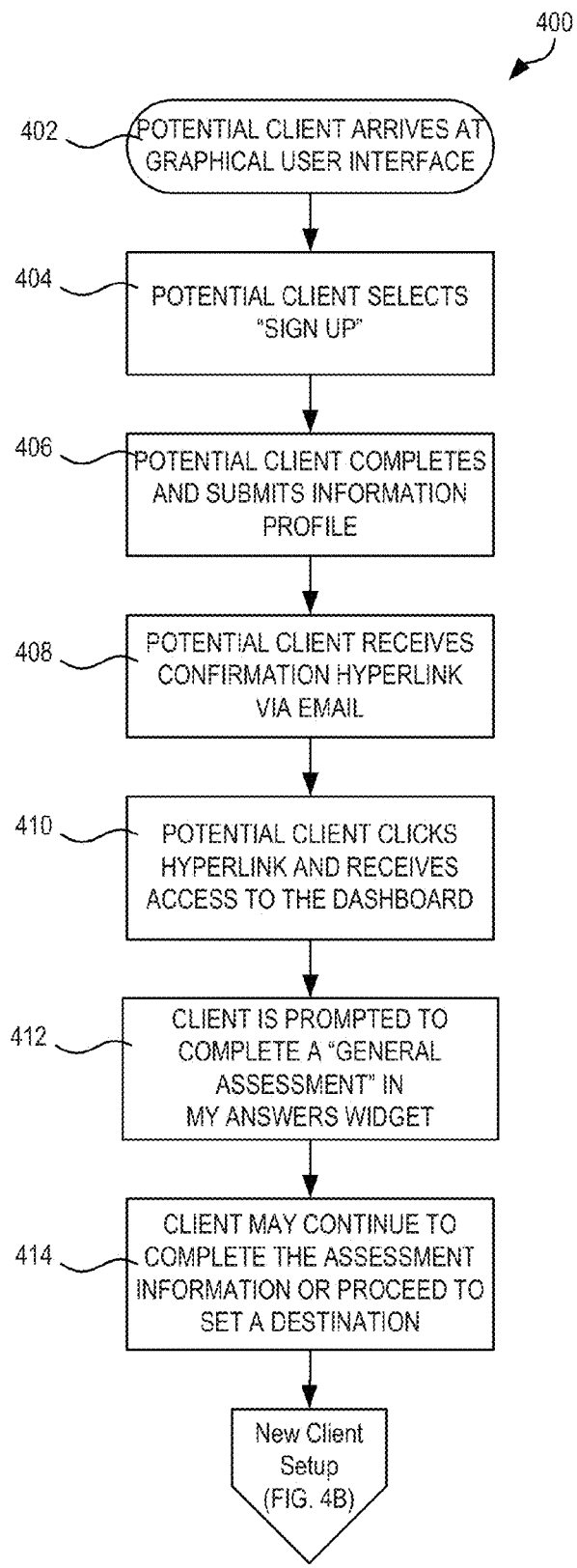
FIG. 4A illustrates a flowchart depicting operations for starting a goal-based workflow according to an example described herein.

FIG. 4A provides an illustration of a flowchart for starting a goal-based workflow 400 according to an example described herein. (It will be understood that the order of operations in this flowchart is illustrative of one example, and thus the order is not intended to be limiting). As shown, a potential user may arrive at a website or other graphical user interface of the information service (operation 402). The potential user may then select the "Sign Up" feature of the website (operation 404). The website may then prompt the potential user to complete an information profile for the potential user. If the potential user is under the age of 18, for example, the potential user may not be allowed to register for the information service. Upon the potential user completing and submitting the information profile (operation 406), the potential user may receive (operation 408) a confirmation hyperlink via email.

After the potential user clicks the hyperlink (operation 410), the information system 100 may consider the potential user to be a user of the system. The user may then receive access to an information system dashboard or other user interface. The dashboard may contain widgets, which may include the "My Answers," "My Destination," and "My Support" widgets. Other widgets may be added to the system as appropriate.

The information system 100 may prompt the user to complete a "General Assessment" in the "My Answers" widget (operation 412). The system may use the user's answers to the general assessment questions, as well as other data, to determine whether the user is in a demographic group that may receive suggestions from the system. If so, the user becomes a "client" of the system. The user may continue to complete the assessment information or may proceed to set a destination (operation 414).

Figure 4B:
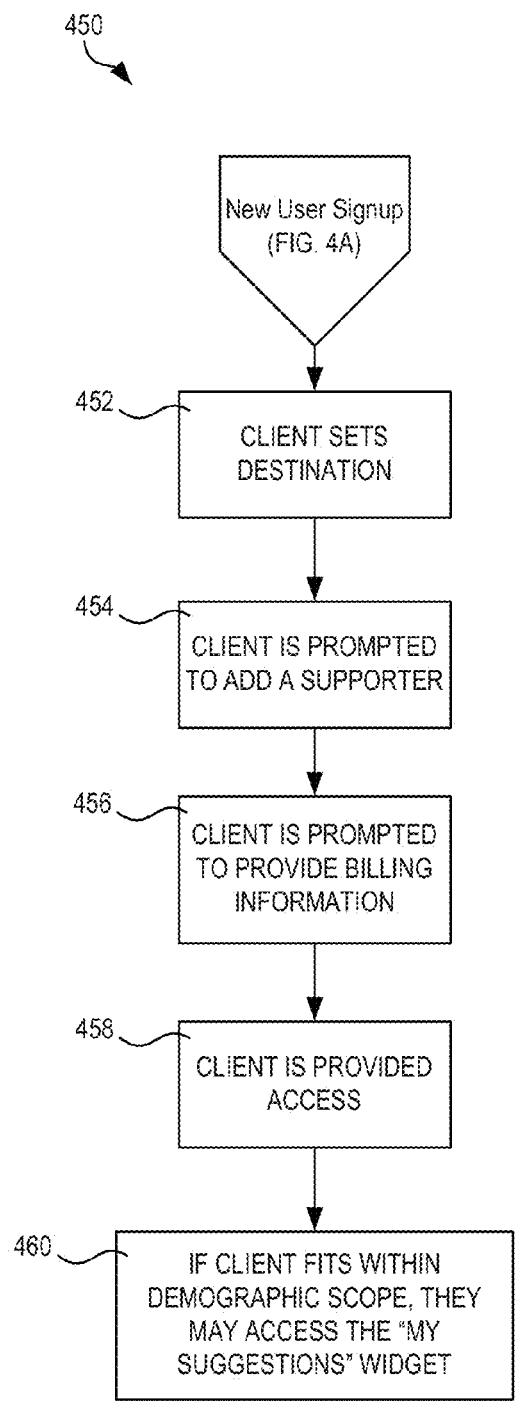
FIG. 4B illustrates a flowchart depicting operations for continuing in the goal-based workflow according to an example described herein.

FIG. 4B provides an illustration of a flowchart for continuing in a goal-based workflow 450 according to an example described herein. After enrolling in the information system 100, the user may set a destination (operation 452). After the user has set a destination, the system may prompt the user to add a supporter (operation 454). After the user has added a supporter, the system may prompt the user to complete the user's billing information (operation 456). The system may harness peer pressure, through the user's supporter(s), to influence the user to enter the user's billing information. The system may then provide access to the user (operation 458). In some cases, the system may notify the user that the user will not be billed for the first 30 days (or some other period) after enrolling in the service.

If the user fits within a demographic currently served by the system, the user may access the "My Suggestions" widget of the information system dashboard. Conversely, if the user does not fit within a demographic currently served by the system, the user may not access the "My Suggestions" widget of the information system dashboard.

The workflows and goals performed in connection with the information system 100 may be implemented with specific strategies and accomplishments to be Specific, Measurable, Attainable, Relevant/Realistic, and Time-bound. As used herein, the "overall goal" may be an environmental goal or result that may be achieved through performance of the strategies or accomplishments by the client 106. The overall goal may be further divided or segmented into time-based or activity-based goals, such as a series of short term goals, intermediate goals, and long term goals.

The client 106 may set the overall goal (within appropriate conditions and business rules), while the information system 100 may provide smaller goals to measure progress towards the overall goal. The overall goal may be a more abstract concept (e.g., "feel better, be healthier, and lose weight") while the time- or activity-based goal may be more specific and quantifiable. Specifically, the time- or activity-based goal may be quantifiable in order to reach some measurable health goal such as: an amount of weight or body measurement lost; a reduction in smoking a number of cigarettes; a self-measurement on a scale of 1 to 10; an assessment by a medical professional; and the like.

The time- or activity-based goal may be provided with a start and end date. When a goal is met, and another is chosen, the start date (by default) may be established from the end date of the previous goal. In some examples, a client 106 may change the start date. Business rules may be established for achieving the time or activity-based goal within a period of time. For example, in a weight loss setting, if the amount of weight that can be lost in a healthy manner in a given timeframe (such as a maximum of 5 kilograms per week) exceeds the "healthy" rate, the client 106 may be prompted to either push back the end-date or reduce the amount of weight to be lost. Business rules may also be applied to automatically adjust and change the goal as appropriate.

In some examples, the client 106 may set the long-term goal, and the information system 100 responds by providing short-term and intermediate goals to measure progress, and establishing satisfaction of the long-term goal from the short-term and intermediate goals. The short-term and intermediate goals may be provided through use of suggested action and suggested action messages, with the performance of the various suggested actions resulting in an increment of progress towards the ultimate goal. The suggested action and goals are therefore structured to allow specific, quantifiable measurements and results (such as success or failure).

Figure 5A:
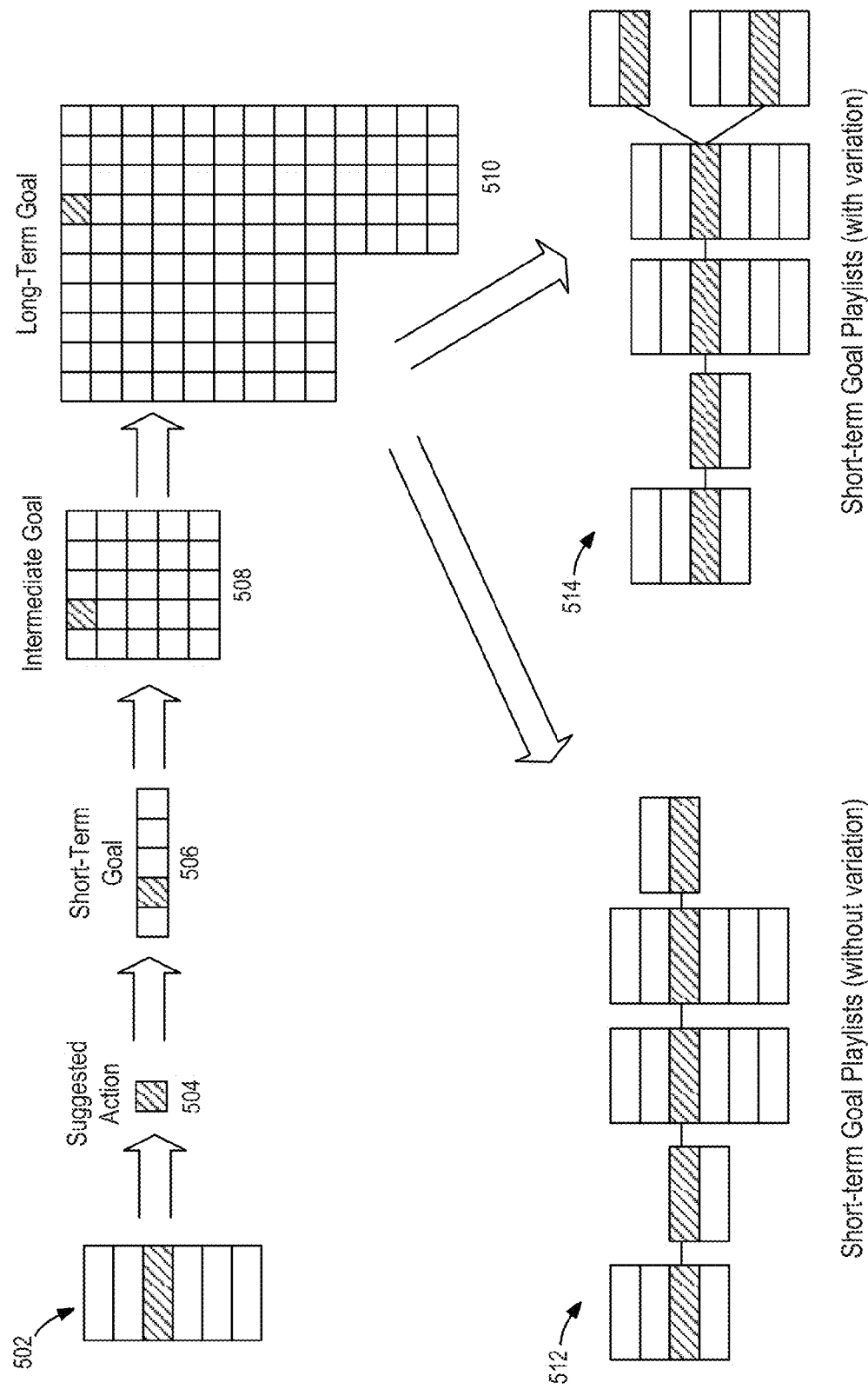
FIG. 5A illustrates a progression of actions and goals in a goal-based workflow according to an example described herein.

FIG. 5A provides an illustration of progression of actions and goals in a goal-based workflow according to one example. As shown, a suggested action 504 is provided in playlist 502 of suggested actions, and may be performed individually as a suggested action, as part of a short-term goal 506, as part of an intermediate goal 508, and as part of a long-term goal 510.

The suggested action and the goals may be accompanied by a temporal aspect of performance, such as a suggested action having performance in under 24 hours; a short-term goal of 5 suggested actions having performance in 2-7 days; an intermediate goal of 5 short-term goals having performance in 8-30 days; and a long-term goal of 5 intermediate goals having performance in 30 days-6 months.

Playlists

Individual suggestions and suggested actions may be linked together to create playlists or programs. For example, as a comparison to a chemistry-like composition, just as atoms are organized together to create molecules and molecules strung together to create large structures with a specific purpose, individual suggestions and playlists of suggestions combine to create programs with a unique purpose and flavor.

A playlist (e.g., playlist 502) is a set of suggested actions (each suggested action being introduced to the user through suggested content) that may be presented to the client 106 as a single "set of suggested actions", individually or as part of a short-term goal 506, intermediate goal 508, or long-term goal 510. Providing a playlist can make user actions to choose or select actions less frequent, and provide a short term context for the client 106. The client 106 may want repetition, variety, to concentrate on a particular area, to see progress in a particular area, or to be generally healthy. Playlists may be designed to link suggested actions together to create a coordinated effort that may consider the desires of the client 106.

The playlist 502 may be chosen as a specific item by the client 106. The playlist 502 may include suggested actions over a period of time, such as a day, week, ten days, months, quarter, year, etc. The client 106 may wish to choose a (somewhat) coordinated effort that is longer than a single action. For example, making sure they eat a healthy breakfast for one week. The playlist feature may allow the client 106 to choose this as a single item. Each suggested action 504 in the playlist may be set for specific times as designated in the playlist (e.g., every x period).

A playlist may be linked as part of a larger program. A program can be: 1) a designation of a specific type of suggested action 504 by keywords (e.g., Mayo Clinic diet, weight watchers diet, etc.), where the suggestion engine 102 preferentially chooses actions or playlists to present to the client 106 as a function of the keywords; or 2) a set of playlists presented in a series, such as a series that has a defined objective (for example, eat a good breakfast for four (4) weeks, which may include suggested actions for both purchasing the materials for a good breakfast, such as oatmeal, as well as allowing enough time to eat it before starting the day's other activities).

For programs of the first type, the client 106 may be offered the option of choosing a program to follow. For programs of the second type, users, such as employees or professional supporters, can create programs by selecting a series of playlists, and then giving a definition, keywords, or additional tags to be included by the program. The program may include a "creator" designation for the user who created the program and the "creator" may title the program. Choosing a program may give the client 106 context for why they are doing the specific eating/movement/self-view suggested action(s) 504.

Supporters may quickly organize suggestions and suggested actions 504 into unique content playlists 502 that are targeted towards groups of clients. Playlists may be short or long (one day or one week), generic or commercial program. A generic eating program might be following a low carbohydrate, low fat, or low calorie diet versus a commercial weight loss or diet. The information system 100 may allow the client 106 to follow their desired type of playlist for their custom environmental goal based on their structured data profile settings or other data input.

An environmental or specific goal 204 set by the client 106 can be a powerful motivation. The goal 204 may be used to determine what percentage of suggested action messages will be, for example, in each of the eating/movement/self view areas. The goal 204 may be used in motivating the client 106 by reminding them of the goal 204 they have chosen.

As depicted in FIG. 5A, short term goal playlists 512 may be established to be predetermined without variation, upon the establishment of the playlist. The short term goal playlists 512 may vary in the number of suggested actions over time, and retain a link between common suggested actions. Short-term goals may be strung together based on difficulty rating, or on other ratings for the appropriateness of the specific suggested action(s). The same short-term goal (or a set of playlists for suggested actions) may also be repeated at appropriate times.

As also depicted in FIG. 5A, short term goal playlists 514 may be configured with variation based on user input, user responses, user preferences, or other factors. For example, the short term goal playlists 514 may provide a branching opportunity to choose one sub-playlist of suggested action if a certain suggested action is performed; if the suggested action is not performed or does not achieve certain results, then another sub-playlist of suggested action may be chosen. As such, the path an individual client takes to get to his or her long-term goal is unique, with n-number of short-term goals, and a variable amount of time.

The suggestion engine 102 may deliver appropriate suggested action content separately or in connection with the playlist(s) to the supporter network 104 or client 106 as a function of a set of rules. These rules can include how the content will be delivered to the client 106 or supporter network 104. The suggestion engine 102 may determine one or more suggested action message or playlists based on the client's psychological, lifestyle, or preference and restriction assessment, or the client goal(s) 204. The suggested action message may be sent to the supporter for forwarding on to the client 106 or directly to the client 106 depending on rules or preferences.

Figure 5B:
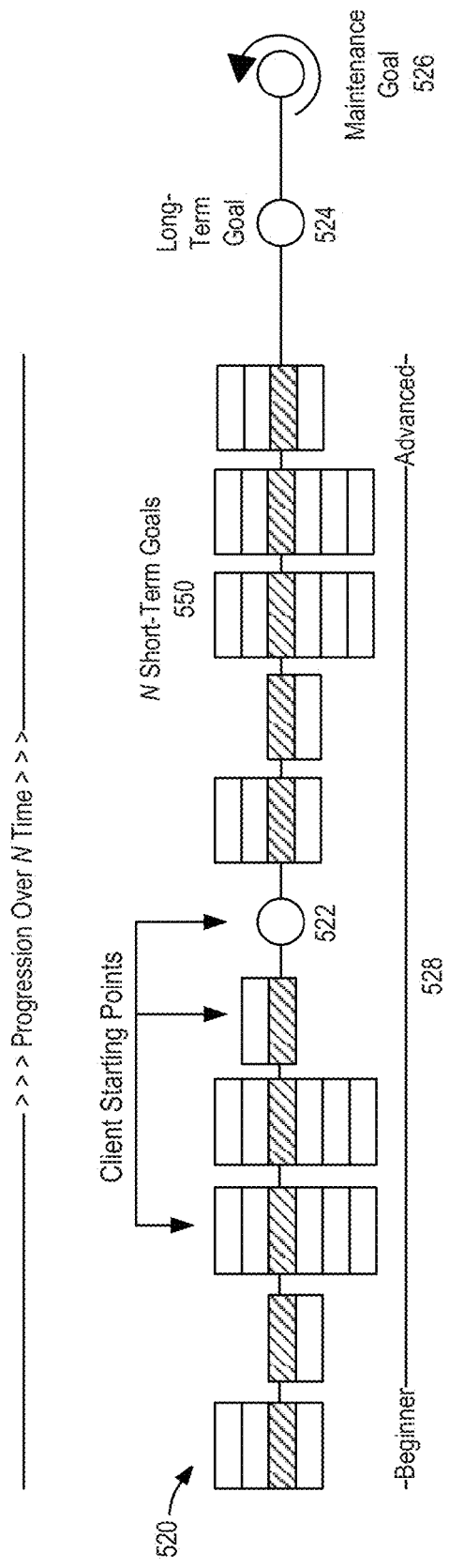
FIG. 5B illustrates a progression of actions and goals in a series of goal-based playlists according to an example described herein.

FIG. 5B provides an illustration of a series of playlists 520 for a particular client 106, having a progression of suggested actions linked during a period of time N towards completion of an intermediate goal 522, completion of a long-term goal 524, and performance of a maintenance goal 526.

The client's starting point along the timeline 528 may be dependent on an experience scale and certain assessments. Such assessments may be conducted to measure progress and receptivity to performance of the overall goal or time-based goals, and the overall execution of the playlist or progress along the experience scale. The assessments may be derived from questions based on general intentions of an initial assessment result, or may be derived according to a specific plan. A client 106 may be considered a "beginner" in some areas but not others. For example, the client 106 may be a beginner in healthy eating, but an expert in exercise and physical activity. The information system may attempt to factor multiple areas when measuring overall progress, to ensure multidimensional attention to different areas of progress and concern.

The progression over N time along the timeline 528 may result in changes to communications and results of the workflow. For example, less interaction (e.g., delivered reminders) may be sent the closer that the client 106 advances to achieving the Long-Term Goal set by the client 106 for a certain date. Upon completion of the long-term goal 524, a maintenance goal 526 may be established. A maintenance goal 526 may be used to reinforce certain behavior through less interaction. A maintenance goal 526 may be used where the client 106 does not necessarily need to "make progress" but would like to continue beneficial activities.

The content provided by the goal-based workflows may follow a general flow. The client 106 may be presented with a number of suggested action messages (or playlists 520), from which they may choose one or more. Messages for the suggested action 504 may be presented as just the action statement with no personalization. A timer of a specified period, such as twenty-four hours, may begin at or around the time the suggested action 504 is chosen. The suggested action 504 may have a designated time of day associated with it, such as morning when the action is breakfast, for when a reminder should be sent—the client 106 may designate times that they regularly do things like breakfast, lunch, or dinner, when they exercise, and when they struggle with being hungry; when the client 106 has not set preferred times when choosing a suggested action, the system may ask the client 106 when they typically do that type of action.

One or more reminders may be sent to the client 106 in connection with the goal-based workflows. The reminder may include personalization—the reminder may be provided at the beginning of the next day, or at or around the time the designated time arrives. A motivation or prompt may be sent to the client 106 at times before or after the reminder. A prompt may be sent to the client 106 after the specified period of time has lapsed. This prompt may ask the client 106 if they have completed the suggested action. If the client 106 has completed the suggested action, they may be rewarded with reward points (also referred to herein as "kudos") or given a congratulatory motivation. If the client 106 has not completed the suggested action, they may be given a conciliatory motivation, such as "you will get it next time!!" The client 106 may be asked if: 1) they would like to try again; or 2) move on to the next suggested action, or something similar. If the response is to try again, the previous action may be presented at the appropriate time with appropriate motivations and prompts; and if the response is to move on, the system may log the incomplete suggested action as not completed and send the client 106 to the next task. If the client 106 has chosen a playlist of suggested action messages, the steps above may be substantially followed, such as without the client 106 being asked if they would like to try again. If the client 106 does not perform a suggested action they may be presented with a conciliatory motivation, and then reminded of the next task in the play list. When a client 106 is sent a suggested action message from a playlist, the playlist name, or the order of the suggested action message may be included in the information available to the client 106.

After the client 106 has chosen a suggested action 304, the system may provide an appropriate motivation, prompt, reminder, or reward statement. The number of motivations, reminders, and prompts may be defined in a suggestion engine 102 database, and may be based on the clients' psychological assessments. A psychological assessment may include determining a receptivity of the client 106 to a motivational or encouraging statement, such as whether the client 106 is a caregiver, colleague, competitor, or authoritarian; a client's engagement in achieving their goal 204, such as whether the client 106 is an optimist, fatalist, activist, or skeptic; a client's social style, such as whether the client 106 is a driver, amiable, analytical, or expressive; or a combination thereof. For example, a message for a caregiver may take the form of admonition, can communicate to the client 106 that the substance of the message is good for them, or be supportive yet direct. Such persons may tend to assume a hierarchical relationship in which they have some form of power over another, yet tend to be more challenging than nurturing in their interactions. A message for an optimist may include encouragement to act, support or pressure from their social network, increasingly persistent reminders to act, or a combination thereof. Such persons tend to think about the suggested action, search for ways to ensure success, overthink or overplan, or have a high level of excitement that may diminish without action. A message for an analytical person may include statistics or data that provide support for why the action should be accomplished, or it may be more task-oriented than person oriented. Such persons may be perfectionists, critical of themselves, systematic or well-organized, prudent, or a combination thereof.

Assessments and Motivation Workflow Examples

The goal-based workflows may be configured to integrate selection and delivery of suggested content with insight and input from supporters in the supporter network 104.

Figure 6A:
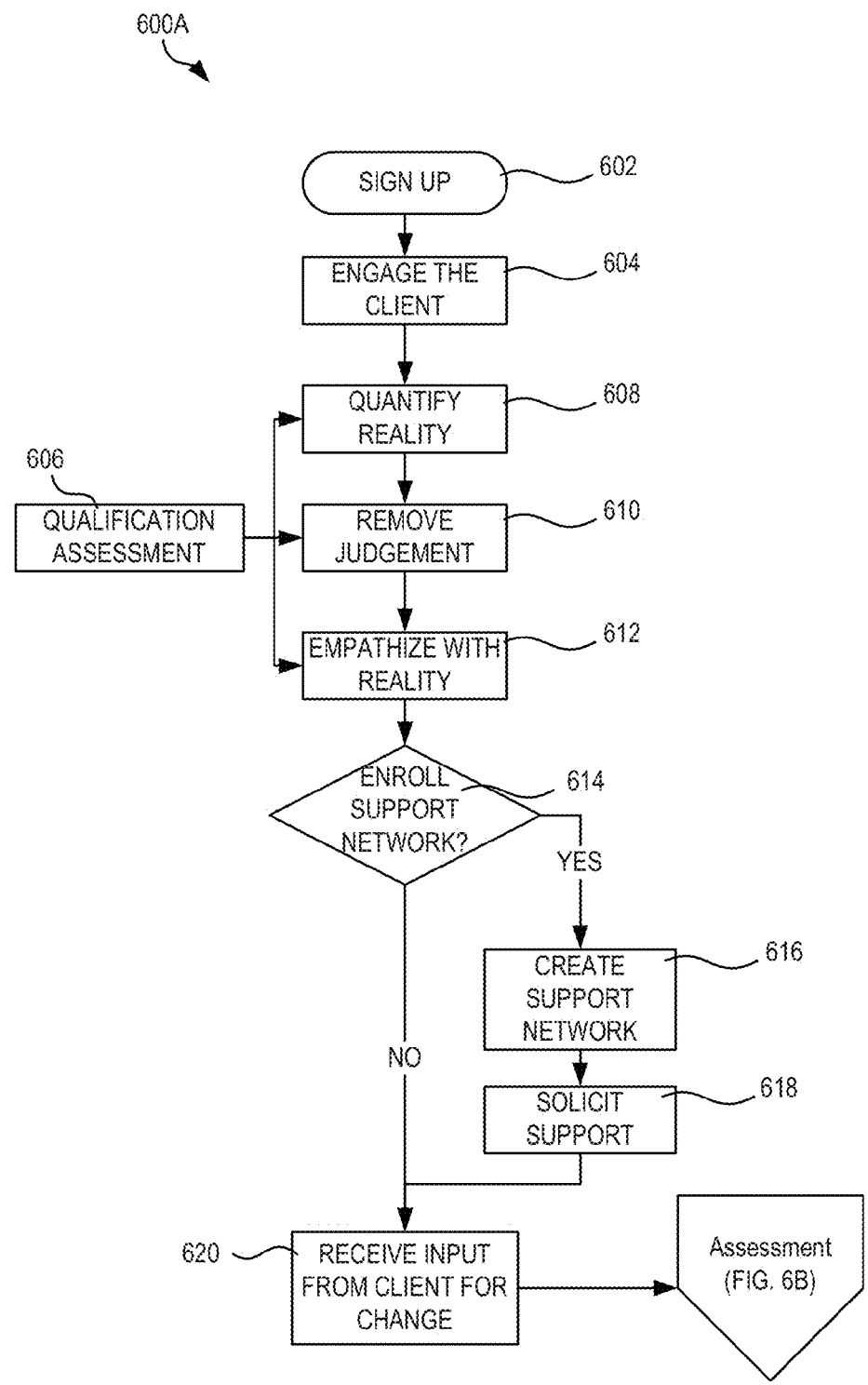
FIG. 6A illustrates a flowchart of client assessment for a client sign-up of a goal-based workflow according to an example described herein.

FIG. 6A illustrates a flowchart of assessment and supporter interaction in a goal-based workflow 600A performed with the information system 100 according to an example described herein. First, a customer (e.g., a client 106, supporter from supporter network 104, or both) may sign up to use the system (operation 602), as the information system operates to engage the client (operation 604). Engaging the client 106 may include receiving personal information or other data 208 about the client 106. A qualification assessment of the particular client 106 then may be conducted (operation 606). The qualification assessment may include using the personal information or other data to verify and quantify the reality the client 106 faces (operation 608). Any words, language, or other indications of a judgment or in the qualification assessment may be identified and removed (operation 610). The information system 100 may further use results of the qualification assessment to provide empathy consistent with the client's reality or situation (operation 612). Empathizing with the client's reality may include personal anecdotes of clients in similar situations, sending encouraging messages including success stories of people in similar situations, or other actions indicative of empathy.

A client 106 may choose to enroll or setup a supporter network 104 to assist with achieving the goal (operation 614). If the client 106 chooses to enroll the supporter network immediately, a support network may be created (operation 616) and the client 106 may solicit support from the support network (operation 618). The support network may be created by a user directly choosing supporters, or from the system assigning supporters suited for the client 106, or a combination thereof. The types and interactions with the support network may also be defined. The ways in which support may be modified include a client choosing a setting, for example, that indicates whether they desire a public or private celebration of a confession or an achievement.

Next, the client 106 may provide input indicating a decision on what he or she wants to change, and what associated destination to reach from the change (operation 620). Deciding what the client 106 wants to change may include choosing goals, indicating that the client 106 wants a particular lifestyle change (such as taking on a more active lifestyle), identifying and modifying desired or undesired behaviors, among others.

Figure 6B:
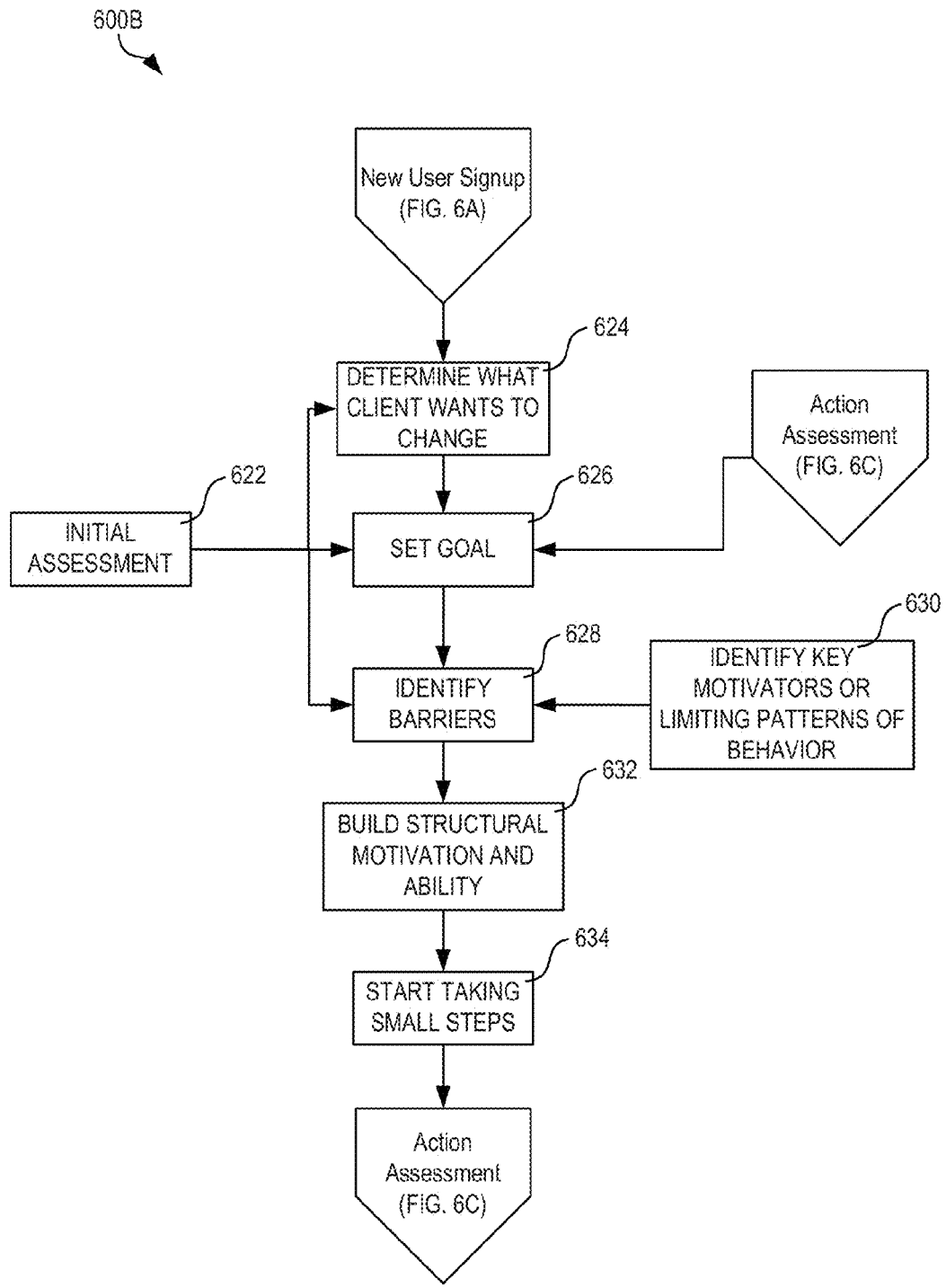
FIG. 6B illustrates a flowchart of additional client assessment and behavior management in a goal-based workflow according to an example described herein.

FIG. 6B illustrates a flowchart of additional assessment and behavior management in a goal-based workflow 600B performed with the information system 100 according to an example described herein. The additional assessment and behavior management in the goal-based workflow 600B may modify or be appended to the client assessment and support network setup and interaction in the goal-based workflow 600A.

An initial assessment, such as psychological or physiological assessment, may be performed upon the client 106 (operation 622). The initial assessment may include determining the client's personality, communication style, or how they like to execute actions or suggestions. For example, it can be determined whether the client appreciates short, concise communications or more elaborate and detailed communications, or if the client is a procrastinator or prefers to stay on top of things. The initial assessment may include the client 106 indicating or deciding what he or she would like to change (operation 624). This may include identifying desired or undesired behaviors or actions. From this assessment and determination, the information system 100 may assist the client 106 with setting one or more goals (operation 626).

Barriers to achieving the goal(s) may be identified (operation 628). Identifying barriers may include identifying key motivators or limiting patterns of behavior (operation 630). Such identification can help the suggestion engine 102 provide content and actions that help the client "rewire" what they see as good, bad, positive, negative, healthy, unhealthy, etc. Such identification may be accomplished by recognizing and evaluating client-provided stories to help identify the key motivators or limiting patterns of behavior.

The abilities of the client and the structural motivation to help the client may be built (operation 632). This can include insuring that behavior change aspects of content and actions are satisfied, such as from multiple behavior change categorizations. Small steps toward the goal can be taken as a result of small actions suggested by the suggestion engine 102 (operation 634). For example, if the goal is to run a half marathon, the suggestion engine 102 may suggest that the client 106 begins by walking a mile during some schedule. A greater likelihood of performance of the small steps can be ensured by sending the client 106 suggestions that are small deviations from the client's current actions.

Figure 6C:
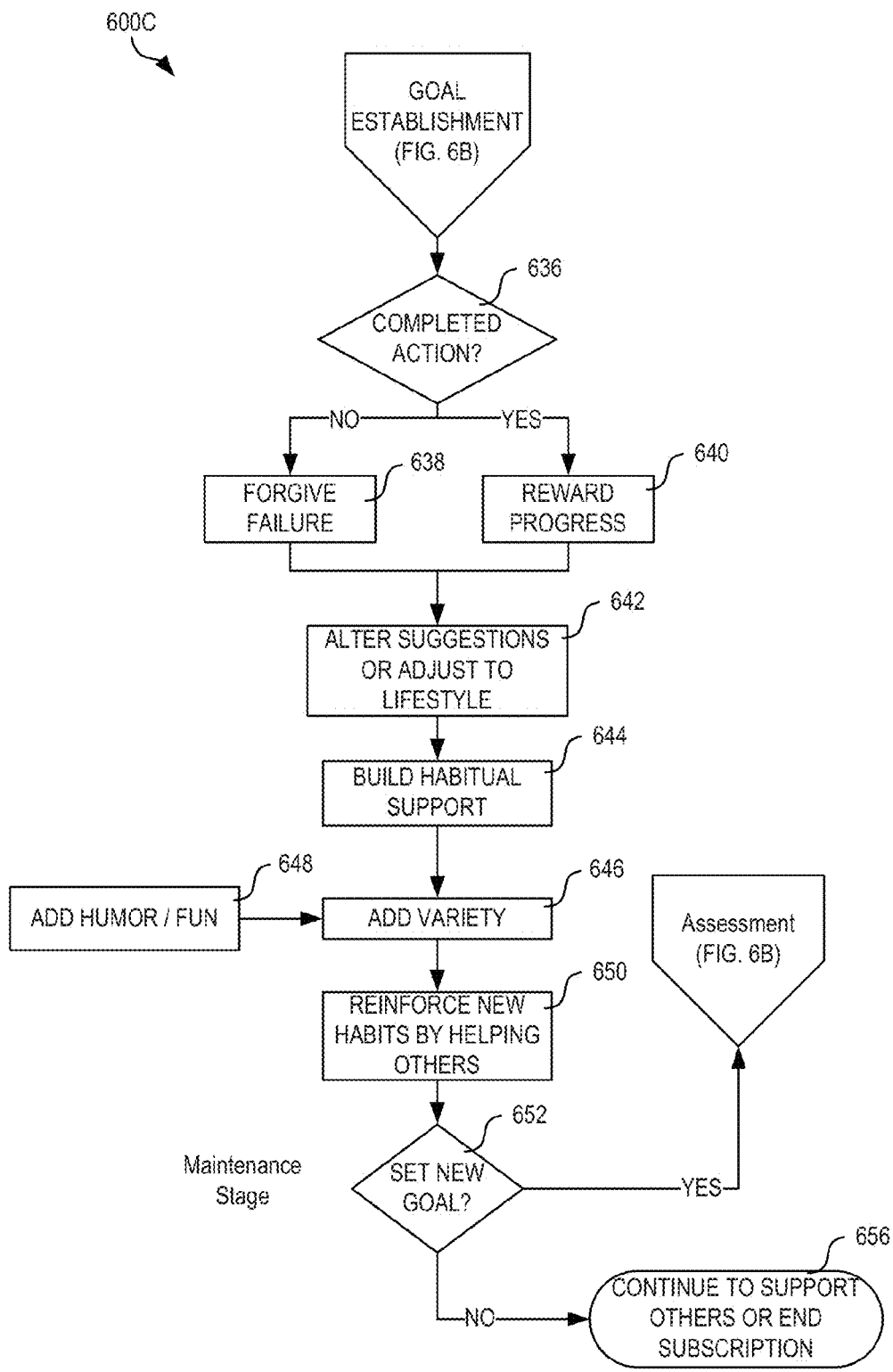
FIG. 6C illustrates a flowchart of client activity management in a goal-based workflow according to an example described herein.

FIG. 6C illustrates a flowchart of activity management in a goal-based workflow 600C of the information system 100 according to an example described herein. The additional assessment and behavior management in the goal-based workflow 600C may modify or be appended to the assessment and supporter interaction in a goal-based workflow 600A or the additional assessment and behavior management in a goal-based workflow 600B.

As a result of the various suggested content, the information system 100 can determine if the action or suggestion was completed (decision 636). If the action was not completed, then the failure to complete the action can be forgiven with an appropriate response conveyed to the client 106 (operation 638). If the action or suggestion was completed, then progress may be rewarded (operation 640). From the results, the suggestions presented to a client 106 may be altered or adjusted to the lifestyle of the client 106 (operation 642).

Habitual support may be built (operation 644). Habitual support may include the supporter network sending suggestions and encouraging messages regularly or on a schedule. Some variety in the suggestions may be added by the suggestion engine 102 (operation 646). This can include adding humor or fun to the suggestions or messages (e.g., video, text, or other messages) delivered to the client 106 (operation 648) in the suggestions. New habits can be reinforced (operation 650). Reinforcing new habits may include encouraging the client 106 to help others achieve their goals, such as becoming part of someone else's supporter network or sending a person facing a similar issue a personal success story, suggestion, or encouraging message. These actions can help the client 106 maintain the healthy or positive behavior through leading or supporting others by example.

The client 106 may be given an option to set a new goal (decision 652), such as at or around the time the client 106 achieves a previously set goal. If the client 106 chooses to set a new goal, then a new goal may be selected or determined and conveyed to the system (with the assessment of FIG. 6B conducted). If the client 106 chooses to not set a new goal, then they may be given the option to continue to support others or end the subscription to the system (operation 656).

Graphical User Interfaces

The presentation and control of information from the information system 100 may be provided in connection with an internet-delivered graphical user interface, such as embodied in a website or software application. FIGS. 7A, 7B, 7C, 7D each provide examples of graphical user interfaces for interaction with the information system 100 in connection with the techniques described herein.

Figure 7A:
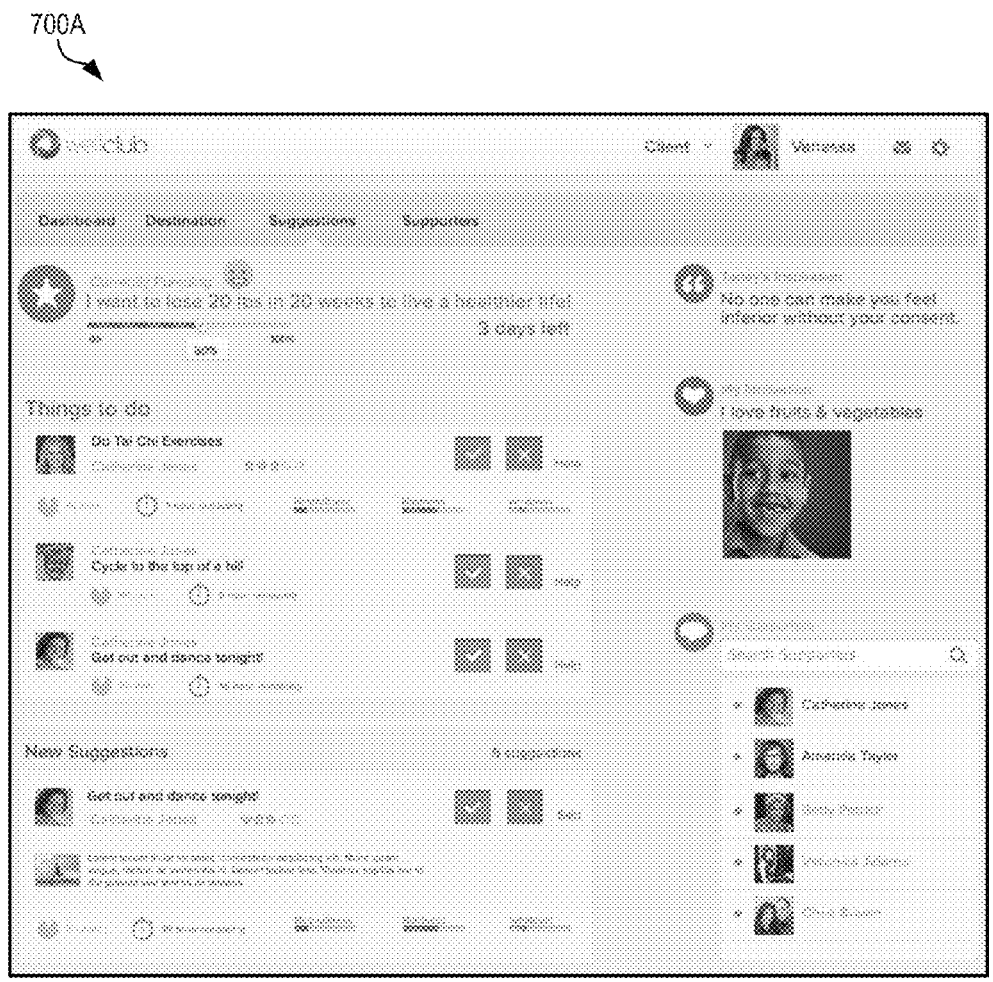
FIG. 7A illustrates a graphical user interface provided for displaying suggestions to a client in a goal-based workflow according to an example described herein.

FIG. 7A depicts a graphical user interface 700A providing a "suggestions" dashboard with a series of suggestions and suggested content. The suggestions dashboard may include a news feed of suggestions and suggestion-related events, incoming suggestions, accepted suggestions, and old suggestions. A summary or detailed view of individual suggestions may be launched from the initial view of the suggestions dashboard. The suggestions dashboard may also enable the user to select or refine the selection of additional suggestions.

The suggestions dashboard may enable the display of a suggestion provided from the information system, from a particular supporter or expert, or from a group of supporters, experts, or other users. The suggestion may be accompanied with summaries of information for the suggestion, such as a category (e.g., "eating", "movement"), estimated time to conduct the action in the suggestions, user ratings of the suggestions, ratings of helpfulness, difficulty, and timeliness of the suggestions, and notes and tips related to the suggestions. The suggestions dashboard may further enable detailed views of information for the suggestion, and the ability to select or interact with particular actions associated with the suggestion.

Figure 7B:
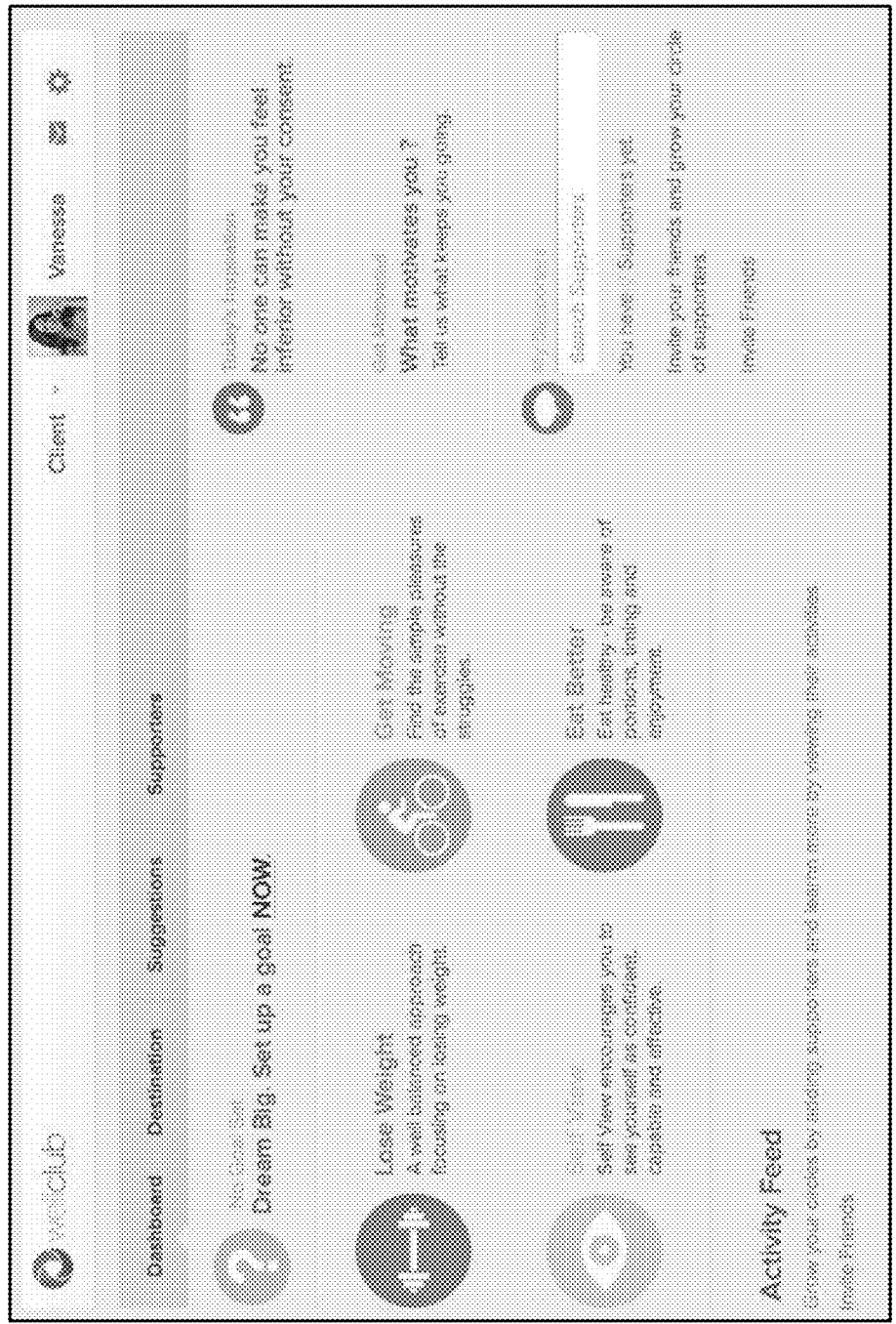
FIG. 7B illustrates a graphical user interface provided for establishing destinations and results for a client in a goal-based workflow according to an example described herein.

FIG. 7B depicts a graphical user interface 700B providing a "destination" goal dashboard for selection of particular goals or sub-goals, to receive and display a particular user focus related to the selected goal(s). The goal dashboard may include a news feed of goals and goal-related events, including supporter activities related to the goal, and a status of a particular user for the goal. The goal dashboard may enable the display and selection of one or multiple particular goals from certain categories (such as "lose weight"; "movement"; "eating", "self-view"). The goal dashboard may be accessed to refine or switch goals at later times.

Figure 7C:
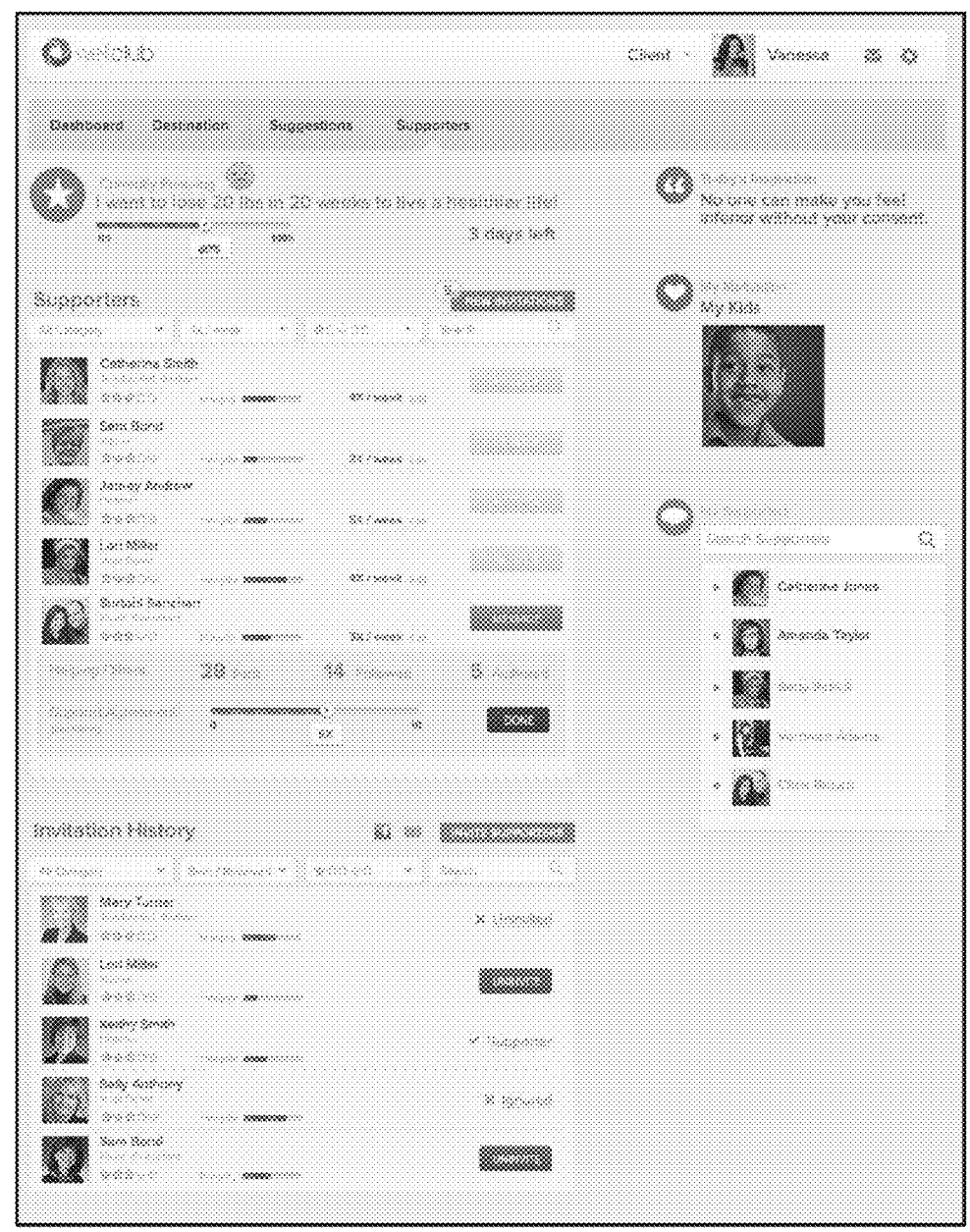
FIG. 7C illustrates a graphical user interface provided for displaying supporter information for supporter interaction with a client in a goal-based workflow according to an example described herein.

FIG. 7C depicts a graphical user interface 700C providing a "supporter's" dashboard for interaction with various supporters such as social network connections, friends, other clients, experts, and medical professionals. The supporter's dashboard may enable the display of a sortable or filterable list of supporters including a brief profile display (such as a picture, name, title, and the like). The supporter's dashboard may also enable the interaction of the user with new supporters discoverable from email services, social networks, and through manual invitations. The supporter's dashboard may also enable a client to send specific targeted messages and invitations to a user or group of users, and modify aspects of the supporter agreement.

Figure 7D:
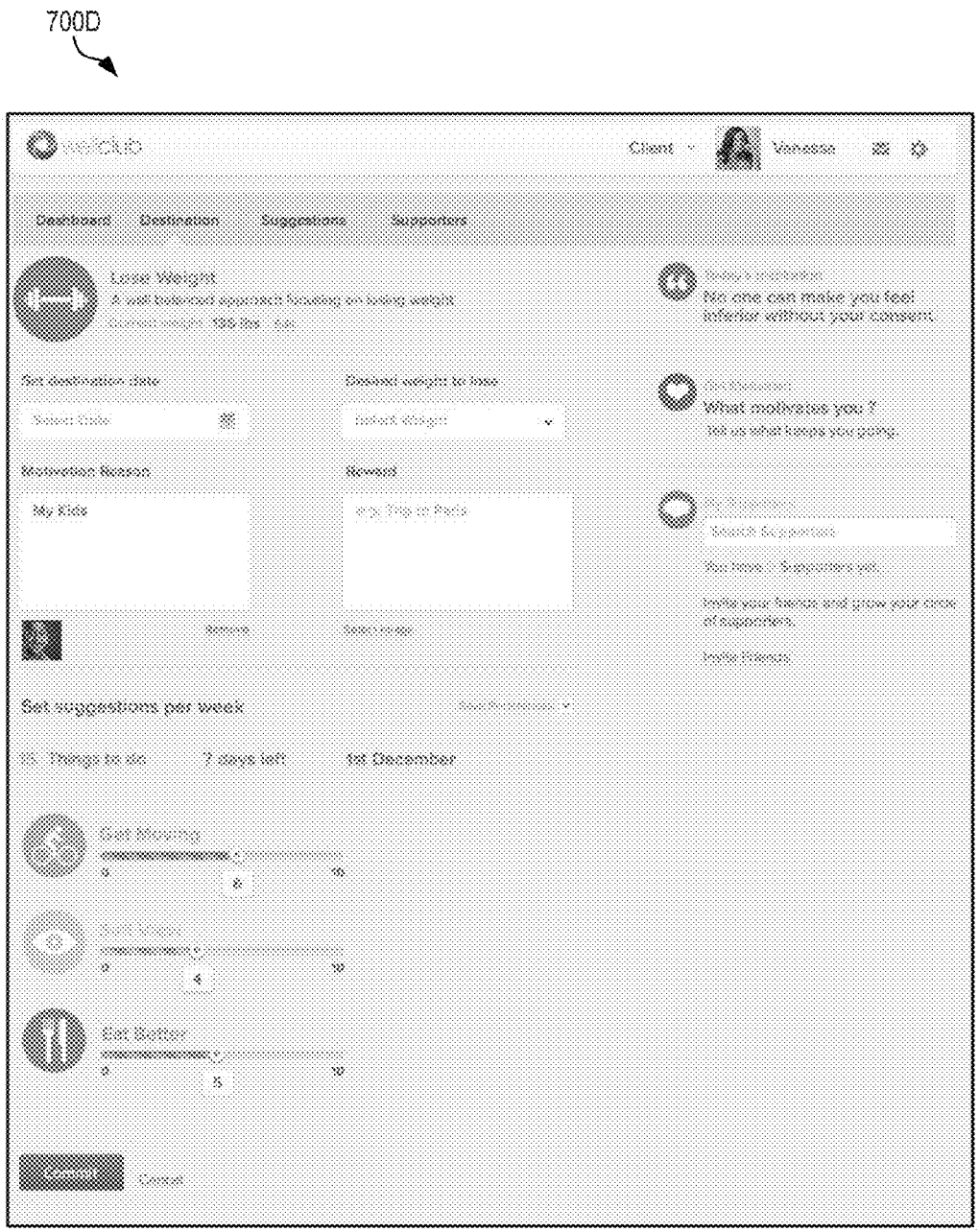
FIG. 7D illustrates a graphical user interface provided for displaying user information and activities to a supporter user in a goal-based workflow according to an example described herein.

FIG. 7D depicts a graphical user interface 700D providing a "snapshot" dashboard for display to a subject client who may also be a supporter of one or more clients. The snapshot dashboard may be used to display a quick view of multiple clients that the subject client is supporting, with appropriate flags (such as a yellow/red light) designating the status of supported clients who need assistance. The snapshot dashboard may also include graphical user interface elements such as charts, graphs, reports, and the like displaying the status of the subject client. The snapshot dashboard may also display various ratings and rewards earned through participation in a program, and statistics on achievement of the goal and overall participation in the program.

Figure 7E:
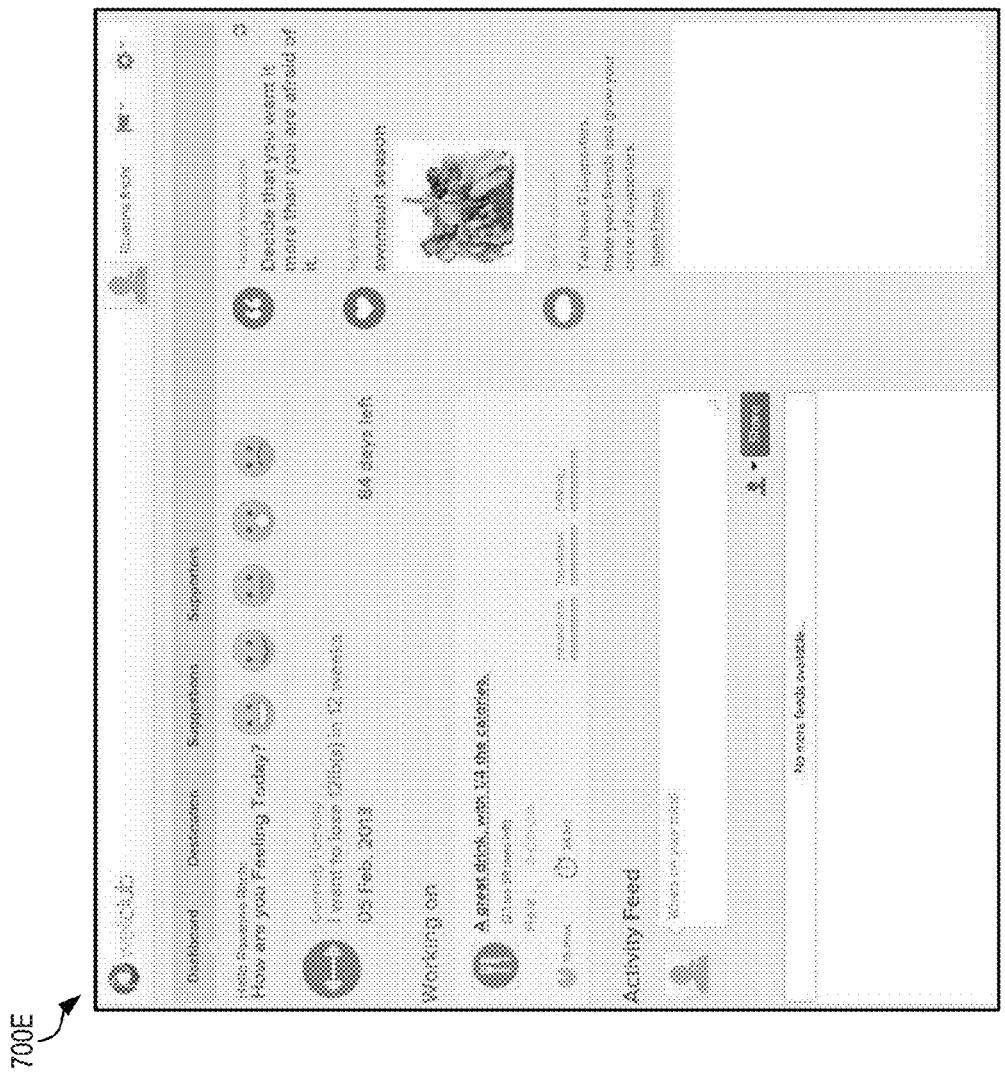
FIG. 7E illustrates another graphical user interface provided for displaying user information and activities to a client user in a goal-based workflow according to an example described herein.

FIG. 7E depicts a graphical user interface 700E providing another "snapshot" dashboard for display to a subject client, with a summarized view of an ongoing activity, ongoing goal, and activity messaging box. The activity messaging box may be used to record interaction with supporters and allow the client to share a status update related to the goal, the activity, and progress or delay. The "snapshot" dashboard may also include reminders of motivation, inspiration, and encouragement from other supporters in an effort to encourage the activity and goal progress.

Figure 7F:
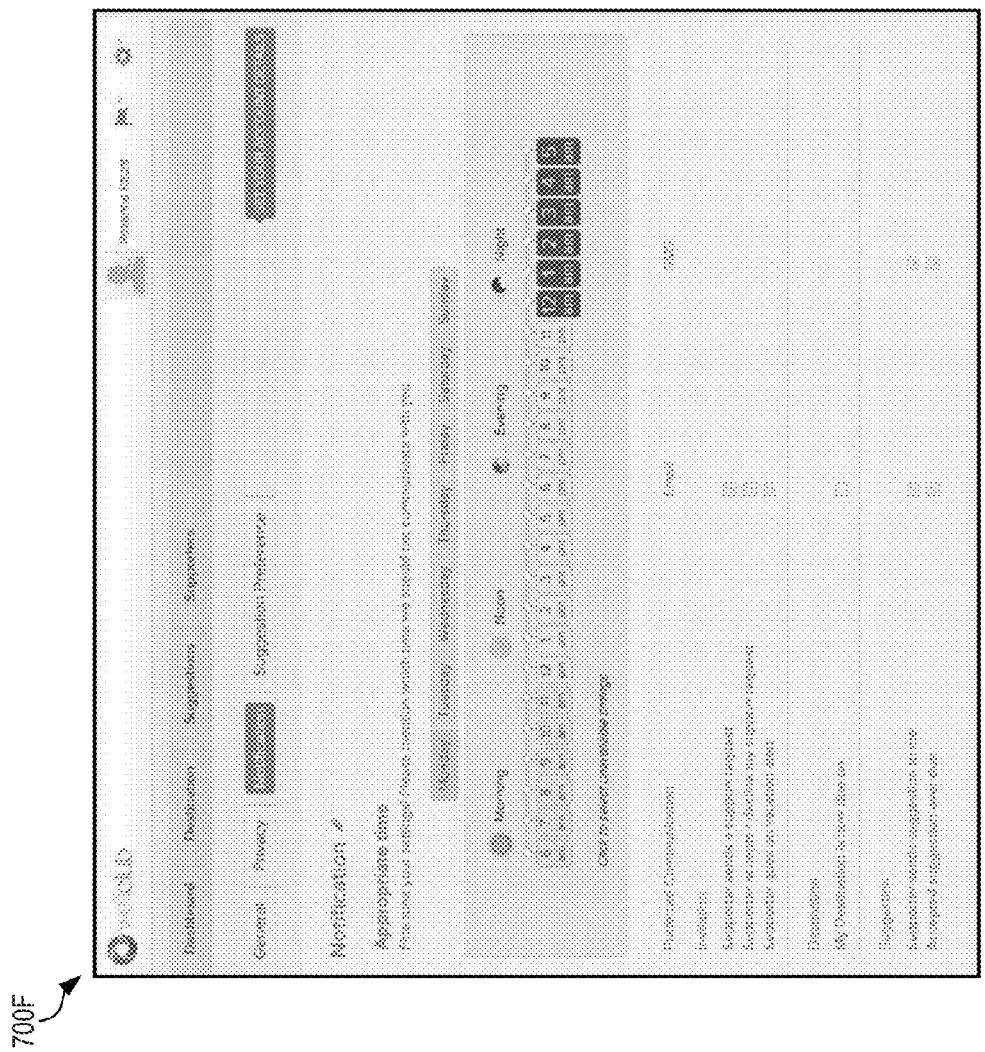
FIG. 7F illustrates a graphical user interface provided for customizing settings for a client user in a goal-based workflow according to an example described herein.

FIG. 7F depicts a graphical user interface 700F providing a "notification" setting for display to a subject client to customize communication settings. For example, particular times of days may be selected for availability with system communications. The user may also specify preferred communication medium settings, and set other suggestion delivery preferences.

Figure 7G:
FIG. 7G illustrates a graphical user interface provided for displaying a profile questionnaire to a client user in a goal-based workflow according to an example described herein.

FIG. 7G depicts a graphical user interface 700G providing a "personality type" profile questionnaire which allows a client to define certain personality characteristics and attributes for assessment. The profile questionnaire may include scaled questions with user-interactive inputs, allowing a user to provide subjective answers to psychological profiling questions. Assessments may also be offered in the graphical user interfaces in the information system using incremental, ongoing questions.

Although the graphical user interfaces 700A-700G were provided with particular examples and illustrations, it will be understood that a wide variety of other graphical user interfaces may be used and employed in connection with the goal-based workflows described herein.

Dynamic Content-Driven Feedback and Prompts

The delivery, presentation, and response mechanisms for providing suggested content and suggested actions may be provided in a linear process to encourage action and appropriate feedback. As reinforcement to the playlists and the coaching style, a prompting system may be performed in connection with the goal-based workflows.

Prompt two-way communication initiated on conditional logic (e.g., from completion of a countdown timer, a count up timer, or an event trigger) may demand a response to an action, or serve as a one-way message for informational purposes (e.g. "We sent a message to your supporter to help you out"). Prompts may be configured to follow a "3 strike rule"—such that if there is no response to the first prompt, another prompt will be sent. If the client 106 does not respond to three messages (by notifications, email, texts) then the information system 100 will stop sending them.

One set of examples of prompted actions requiring a response may include: Suggestion expired; Need to fill out profile; Need to set destination; Need to add a Supporter; Subscription expired; Haven't participated in three days, and not on "vacation mode"; Low on integrity—Client may restart goal.

Prompts are an enhanced feature of coaching that push the client 106 towards his or her environmental goal 204 in a variety of styles (e.g. a mild, moderate, or aggressive style). Rather than simply monitoring the client's progress towards their environmental goal 204, the information system 100 may incorporate a pushing strategy with feedback, to obtain clarification of the various ways (and reasons) that the client 106 can be motivated towards his or her environmental goal 204.

The content suggestion engine techniques and operations described herein may also incorporate a variety of machine-learning and artificial intelligence concepts to adapt to context information (such as feedback), and deliver the content to the client 106 using appropriate timings and mechanisms. As the suggestion engine 102 produces suggested actions and obtains client feedback, the suggestion engine 102 may start to learn what is successful, and apply greater weights to a particular suggested action with a higher likelihood to succeed, thereby producing a cycle of improvement with a greater likelihood of progress towards goals 204.

Figure 8:
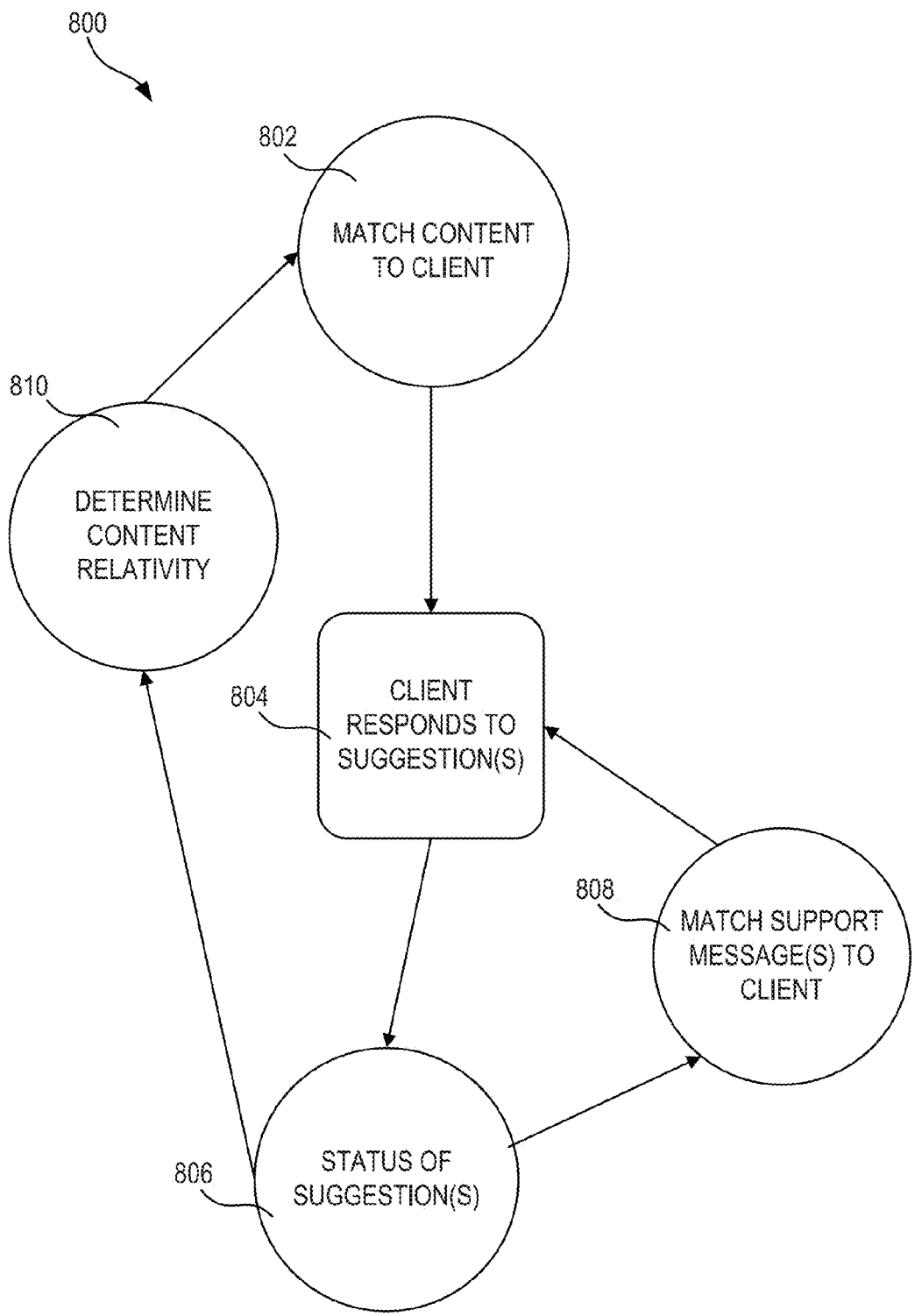
FIG. 8 illustrates an example technique of client interactivity with suggestions from a content suggestion engine in a goal-based workflow according to an example described herein.

FIG. 8 illustrates an example technique 800 of client interactivity with a suggested action generated from the suggestion engine 102. At operation 802, content can be matched to a client 106, such as through data processing techniques, and filtering and weighting techniques produced in connection with a content suggestion or selection engine. At operation 804, the client 106 may respond to the suggested action, such as by accepting or rejecting the suggested action message. A lack of response within a period of time may also serve as a response. At operation 806, the status of the suggested action may be determined, such as determining if the suggested action message was accepted or rejected, or when the suggested action message is accepted and whether the action in the suggested action message is completed or not. At operation 808, a support message may be sent to the client 106, such as sending the client 106 an encouraging or motivating message to try to get the client 106 to complete the action. At operation 810, content relativity may be determined, and such relativity may be recorded for use in a future suggested action.

If questionnaires or psychological/physiological profiling indicate that a problem exists in an area (e.g., movement, eating, self view, etc.) that is different from the goal(s) 204 created by the client 106, then the system may ask the client 106 to review the goal(s) 204 or suggest the client 106 add another goal and indicate what that goal is. The system may also encourage the client 106 to achieve the goal 204 by giving reward points (e.g., kudos) or other incentives.

As a new client signs into the system and is given the opportunity to fill out questionnaires or to begin a suggested action, he or she may decide to use the system right away without filling out much information about them. These clients may be given a suggested action without much data about the client 106 that the suggestion engine 102 can process. A new client may also choose a program from a group of pre-created programs. These programs may include a suggested action that encourages the client 106 to achieve goal(s) 204 related to movement, eating, or self view, encourages the client to perform suggested actions that helps them learn the different features of the system, record how the client 106 uses the system, and suggests that the client 106 fill out questionnaires, at intervals or regularly. Getting feedback on a suggested action may help the suggestion engine 102 determine which suggested action to recommend to the client 106 after the program is complete.

When completed, a suggested action may be put back into a suggested action database. Any completed suggested actions may be withheld from retrieval from the suggested action database for a specified period of time. Such withholding time may be based on a client preference, such as the client 106 indicating that they prefer variety or sameness in the suggested action messages 502 that are presented to them. For example, if a client 106 indicates that they prefer variety, a completed suggested action may be withheld for a longer period of time than if the client 106 indicates they prefer sameness.

A goal may be accomplished when the client 106 indicates the goal has been accomplished or when the system determines that the goal has been accomplished. For example, the system may ask the client 106 or the client's supporters if the goal has been accomplished.

A client 106 may indicate that the suggested action was not timely. In such situations the system may ask the client 106 when the suggested action message would be or would have been timely. A timing tag related to a suggested action message may be adjusted accordingly. Timing tags may indicate an amount of time that the client 106 may be given to complete the task, such as 15, 30, 45, or 60 minutes, etc.

The difficulty rating (a tag) of a suggested action may be altered in accordance with client feedback. The weight of a suggested action may be altered as a client's ability to complete a type of suggested action changes. For example, if a client 106 rates a suggested action as too hard, the weight of the suggested action may be decreased and the weight of suggested actions with lower difficulty may be increased.

Figure 9:
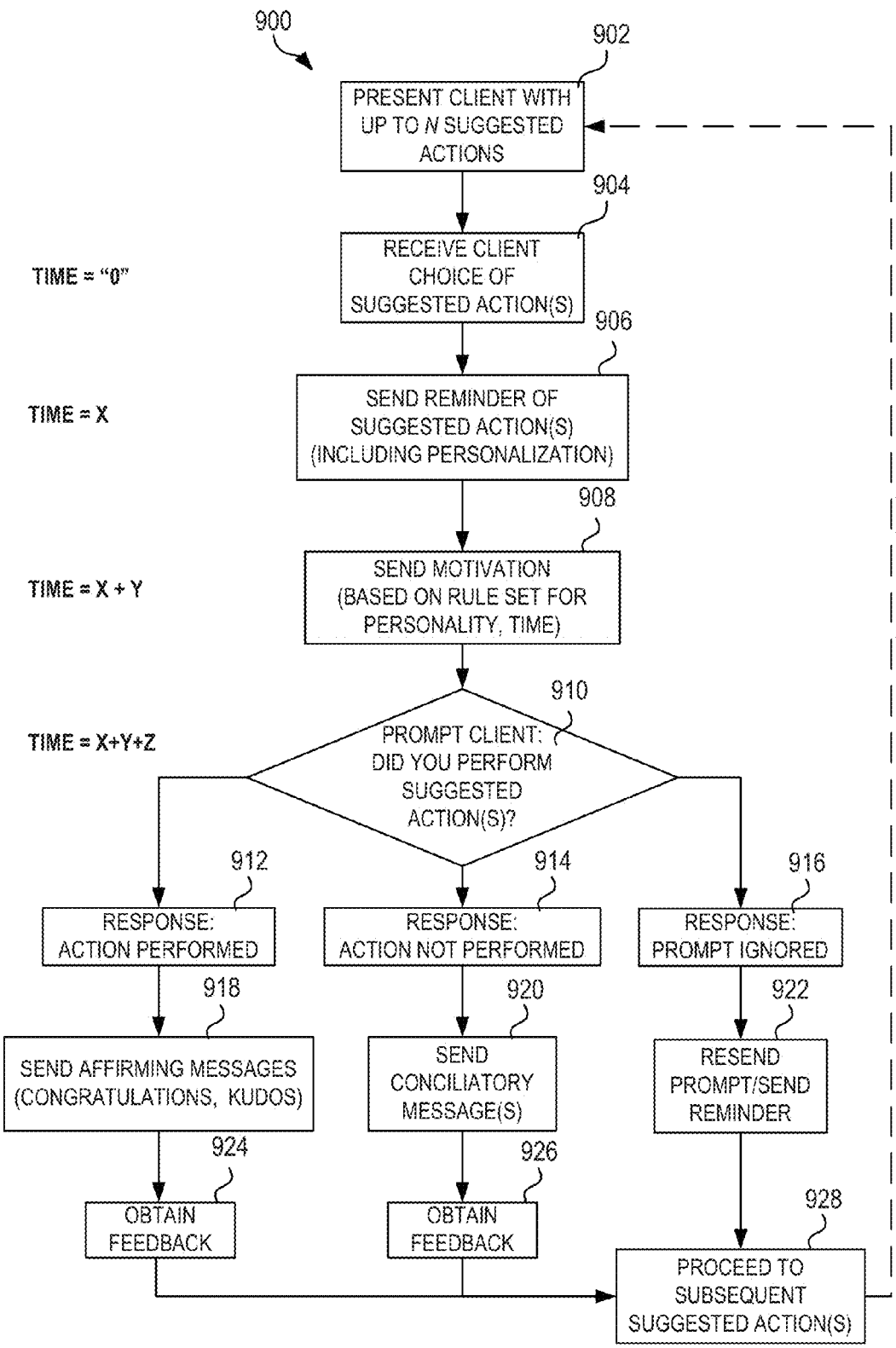
FIG. 9 illustrates an example technique of delivering suggested actions to and obtaining feedback from a client in a goal-based workflow according to an example described herein.

FIG. 9 provides an illustration of a technique 900 for delivering suggested actions and obtaining feedback from human users according to an example. The delivery, presentation, and response mechanisms for providing suggested content and suggested actions may be provided in a linear process to encourage action and appropriate feedback.

At operation 902, a client 106 may be presented with up to N suggested actions. The suggested actions may be chosen from a pool of possible suggested actions using various data processing techniques, such as filtering and weighting. At operation 904, the system may receive the client's choice of suggested action(s). At operation 906, the system may send a reminder to the client 106 that the chosen suggested action should be accomplished. At operation 908, a motivating message may be sent to the client 106. The motivating message may be configured as a function of the client's personality type 210, the goal(s) 204, the time frame which the client 106 set to accomplish the goal 204, other data 208, or contextual user information.

At operation 910, the system may prompt the client 106 to indicate whether they performed the chosen suggested action or not. There are at least three responses the client 106 may provide.

In one scenario, at operation 912, the client 106 may respond that the suggested action was performed. At operation 918, the system may send an affirming message (e.g., a congratulations or kudos) to the client 106. At operation 924, the system may obtain feedback from the client 106, such as by asking the client 106 questions about their experience in performing the suggested action.

In another scenario, at operation 914, the client 106 may respond that the suggested action was not performed. At operation 920, a conciliatory message may be sent to the client 106 from the system. At operation 926, the system may obtain feedback from the client 106, such as by asking why the suggested action was not completed.

In another scenario, at operation 916, the client 106 may respond by ignoring the prompt. At operation 922, the system may resend the prompt, send a reminder that the suggested action should be performed, or present a different set of suggested actions, such as at operation 904. Regardless of the response received from the client 106, the system may proceed to present subsequent suggested actions at operation 928 (e.g., the process may start over at operation 902).

Figure 10A:
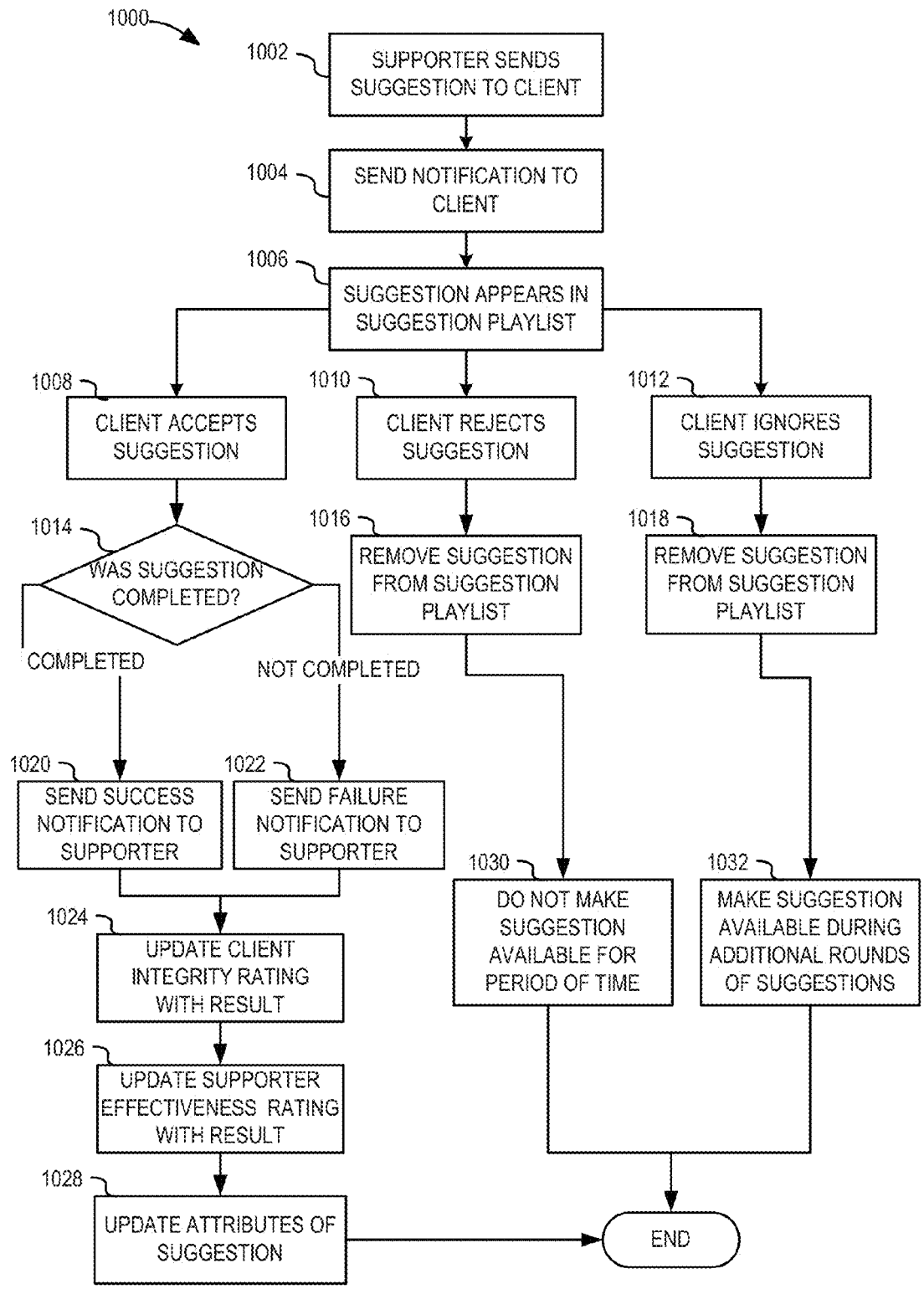
FIG. 10A illustrates an example technique of processing client interaction with suggested actions of a suggestion playlist in a goal-based workflow according to an example described herein.

FIG. 10 illustrates an example technique 1000 of processing user interaction with suggested actions of a suggestion in a suggestion playlist in a goal-based workflow according to an example described herein. First, a supporter may send a particular suggestion to a client 106 (operation 1002). A notification of the particular suggestion may be sent to the client 106 (operation 1004). The notification may indicate that the suggestion has been sent to the client 106. The suggestion may appear in a suggestion playlist for the client 106 (operation 1006).

At this point the client 106 may take one of at least three actions: 1) the client 106 may accept the suggestion to make the suggestion part of the playlist (operation 1008); 2) the client 106 may reject the suggestion and refuse to perform the suggested action in the suggestion (operation 1010); or 3) the client 106 may ignore the suggestion and not do anything with regard to the suggestion (operation 1012).

If the client 106 accepts the suggestion, it may be determined if the suggestion was completed (decision 1014), such as by asking the client 106 if they completed the suggestion. If the suggestion was completed, then a success notification may be sent to the supporter who sent the suggestion (operation 1020). If the suggestion is not completed, then a reminder may be sent to the client 106 or a failure notification may be sent to the supporter who sent the suggestion (operation 1022). A client integrity rating may be updated in accord with the result (whether or not the client 106 completed the action) (operation 1024). A supporter effectiveness rating may be updated with the result (operation 1026). Various attributes (e.g., difficulty, helpfulness, timeliness) of the suggestion also may be updated (operation 1028).

If the client 106 rejects the suggestion (operation 1010), the suggestion may be removed from the suggestion playlist (operation 1016) and the system may prevent the suggestion from being suggested again for a period of time or indefinitely (operation 1030).

If the client 106 ignores the suggestion, the suggestion may be removed from the suggestion playlist (operation 1018) and the suggestion may be made available for the next, or a subsequent round, of suggestions (operation 1032), or the system may prevent the suggestion from being suggested again for a period of time.

A reminder may be provided to the client 106 regarding the suggestion. The reminder is a message from the information system 100 that is sent at a time between when a suggested action is accepted or ignored and when their suggested action is completed. A reminder can take the form of a calendar reminder. Reminders may be configured as a function of a category that the suggested action belongs to, such as eating, movement, or self view. In some examples, a self-view suggestion may be accompanied by a reminder to complete the action about 6 hours before the suggestion may be completed. In some examples, an eating suggestion may be accompanied by a reminder that is sent to the client 106 about a half-hour before the meal or preparation for the meal. In some examples, a movement suggestion may be accompanied by a reminder that is sent to the client 106 about 12 hours before the client 106 is to complete the suggestion. Other notifications may be sent to the client 106 or other users of the application. A notification may be a "call to action" that directly impacts the client 106, a supporter in the supporter network 104, or a dual role user regarding their support network, progress, account settings, subscription, or other miscellaneous items.

Figure 10B:
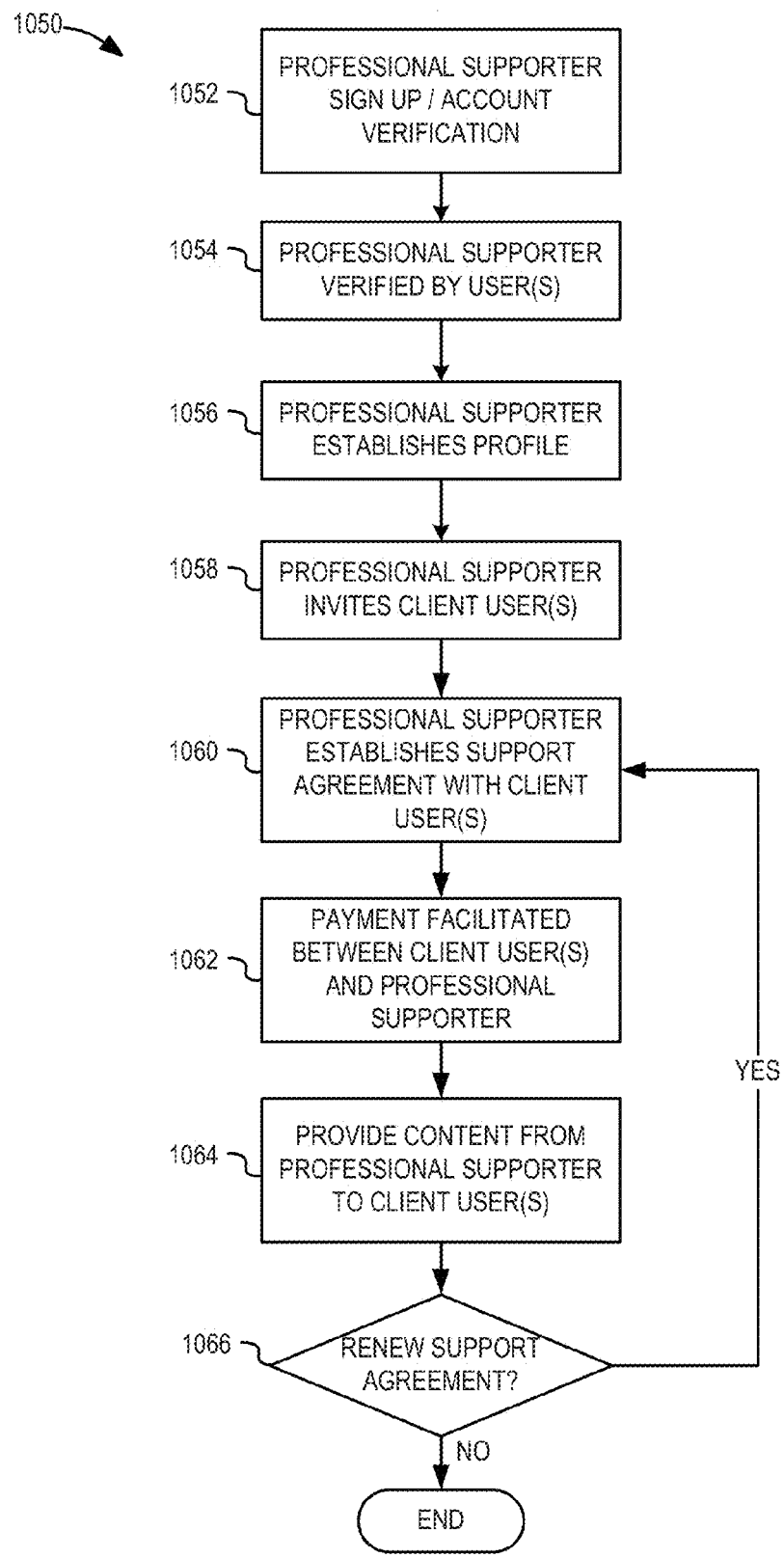
FIG. 10B illustrates an example technique of establishing a support agreement between a professional supporter and a client according to an example described herein.

In some examples, the supporter may be designated as a "professional supporter," and designated to provide fee-based or compensated support to various clients. FIG. 10B depicts an establishment of a support agreement with between client users and a professional supporter, in an example technique 1050 according to an example described herein.

As shown, a professional supporter may establish an account through a sign up and account verification process (operation 1052). This may include the professional supporter filling out a sign up form, and be subject to an account verification or confirmation process. The professional supporter then may be verified by one or more users (operation 1054), which may include administrative users, or recommendations from clients. For example, the professional supporter may be a "basic" or regular supporter until verified/confirmed. The professional supporter will then establish their profile (operation 1056) to include information such as area of practice/expertise, certification(s), qualifying degree, billing for services, biographical information, publications, client reviews, and contact information.

As shown, the professional supporter may invite one or more client users (operation 1058) or otherwise select certain clients for a supporting role. For example, invitations may be sent by email, social network, or based on client actions. After the respective clients accept the supporting role, the professional supporter will establish a support agreement with the one or more client users (operation 1060). This support agreement may include varying levels of support based on varying fee levels and charges. In some examples, the client user may also suggest changes to the support agreement for approval by the professional supporter.

After establishment of the support agreement, payment is facilitated between the one or more client users and the professional supporter (operation 1062). This payment may occur before, during, or after the term of the support agreement. The subscription system may take a portion of the payment (for example, compensating the professional supporter 70% of all payments received). During the support agreement, the professional supporter will provide content (including customized content) to the one or more client users (operation 1064). In some examples, the professional supporters may receive more status information about the psychological or activity status of one or more client users than basic supporters. Also in some examples, the support agreement may be renewed (decision 1066), which if renewed, will result in a new support agreement (operation 1060), payment (operation 1062), and content to the client (operation 1064).

Destination-Based Goals and Workflows

The goal-based workflows may be configured to consider a specific type of goal and the destination associated with each. The workflows may be configured to consider the type of goal that the client 106 has set. The workflows may consider the goal, experience, and personality of the client 106 to cater a playlist or a pool of suggestions to the client 106.

Figure 11A:
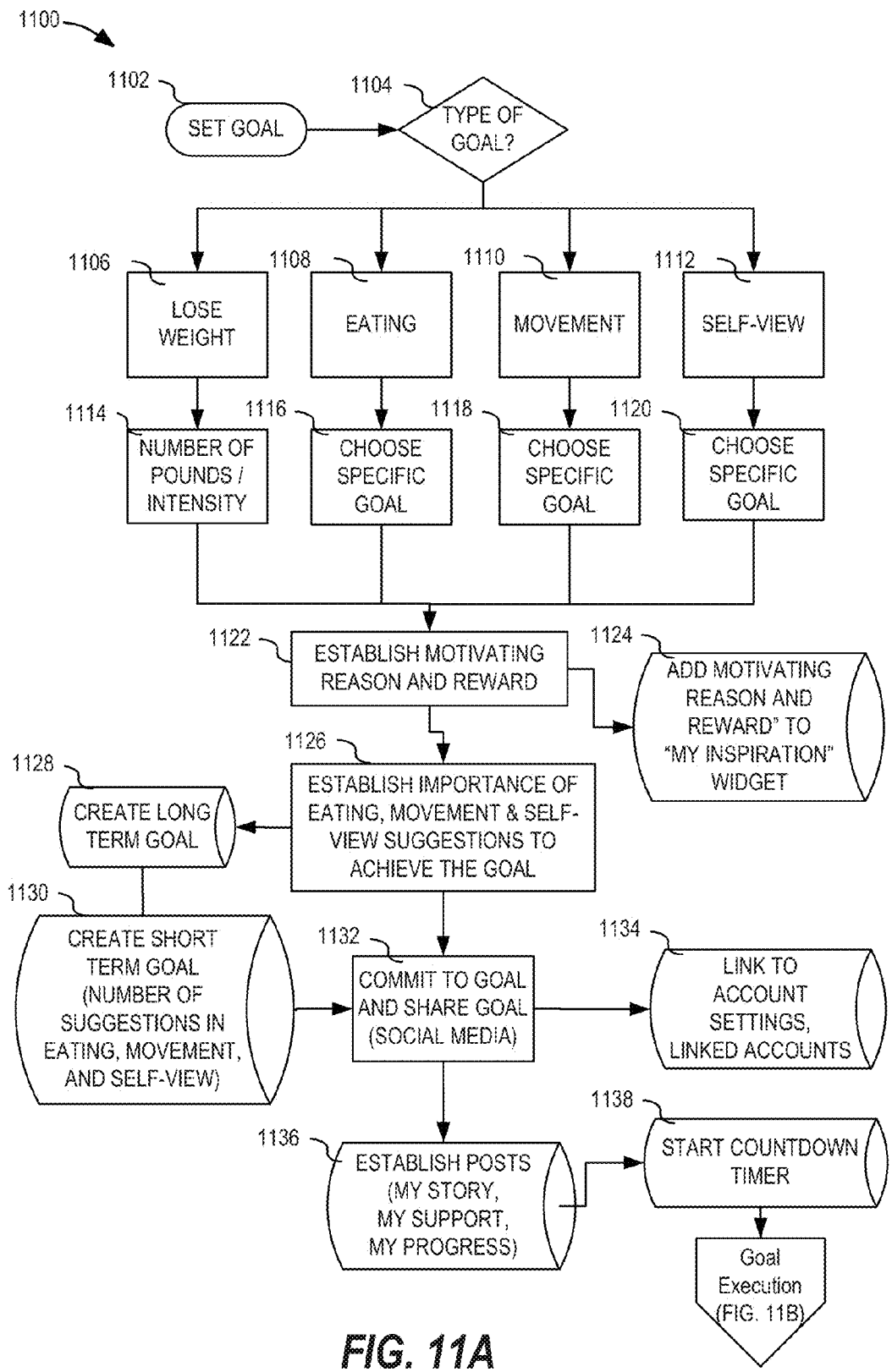
FIG. 11A illustrates a flowchart of goal selections and interactions in a goal-based workflow according to an example described herein.

FIG. 11A illustrates a flowchart of goal-based actions and responses in a goal-based workflow 1100 according to an example described herein. The various action and responses may occur in connection with a software or other user-interactive application, such as provided with a graphical user interface to the information system 100. First, a goal can be set by the client 106 (operation 1102). The particular type of goal that was set may be evaluated further as follows (decision 1104).

When the goal is to lose weight (choice 1106), the number of pounds to lose and the intensity desired may be determined (operation 1114). When the goal is to improve eating habits (choice 1108) (e.g., eat healthier), the client 106 may choose a more specific goal (operation 1116). The more specific goal may be chosen from a list provided by the application. The list may be provided as a dropdown menu, an interactive list that allows the client 106 to click on the specific goal, or other form of providing the client 106 with more specific goal options. Some examples of more specific eating goals include eating well, better drinking habits, following a meal plan, cooking healthier meals, etc.

When the goal is to improve movement (choice 1110) (e.g., to lead more active lifestyle or be more mobile), the client 106 may choose a more specific goal (operation 1118). The more specific goal may be chosen from a list provided by the application. The list may be provided as a dropdown menu, an interactive list that allows the client 106 to click on the specific goal, or other form of providing the client 106 with more specific goal options. Some examples of more specific movement goals include going to the gym a specified number of times a week, running more or a specific distance (e.g., a marathon or a half-marathon).

When the goal is to improve self-view (choice 1112), the client 106 may choose a more specific goal (operation 1120). The more specific goal may be chosen from a list provided by the application. The list may be provided as a dropdown menu, an interactive list that allows the client 106 to click on the specific goal, or other form of providing the client 106 with more specific goal options. Some examples of more specific movement goals include calming the client's mind, feeling better about oneself, or being more comfortable with one's appearance.

The motivating reason, or the reward for achieving the goal may be chosen or determined (operation 1122). The motivating reason or the reward may be added to a widget that may be randomly displayed on a display device used by the client 106 (operation 1124). The relative importance of eating, movement, or self-view suggestions to achieving a client's goal may be determined (operation 1126). A long-term goal may be identified or created (operation 1128). One or more short term goals may be identified or created (operation 1130). Creating the short term goal may include establishing a number of suggestions of various categories (e.g., eating movement, or self-view). The client 106 may commit to the goal and share that the client 106 has committed to the goal with others (operation 1132). The application may post on the client's wall on a social media site such as Facebook, on the client's Twitter account, or broadcast to another social media site that the client 106 is taking on the challenge of achieving the goal, such as through a hot link that may be set up by the client 106 (data operation 1134). Information regarding the client's commitment to the goal may be posted to their profile, their support page, or their progress page, on the application (data operation 1136). A timer, such as a countdown timer, may be started that indicates to the client 106 how long they have to achieve the goal (data operation 1138).

Figure 11B:
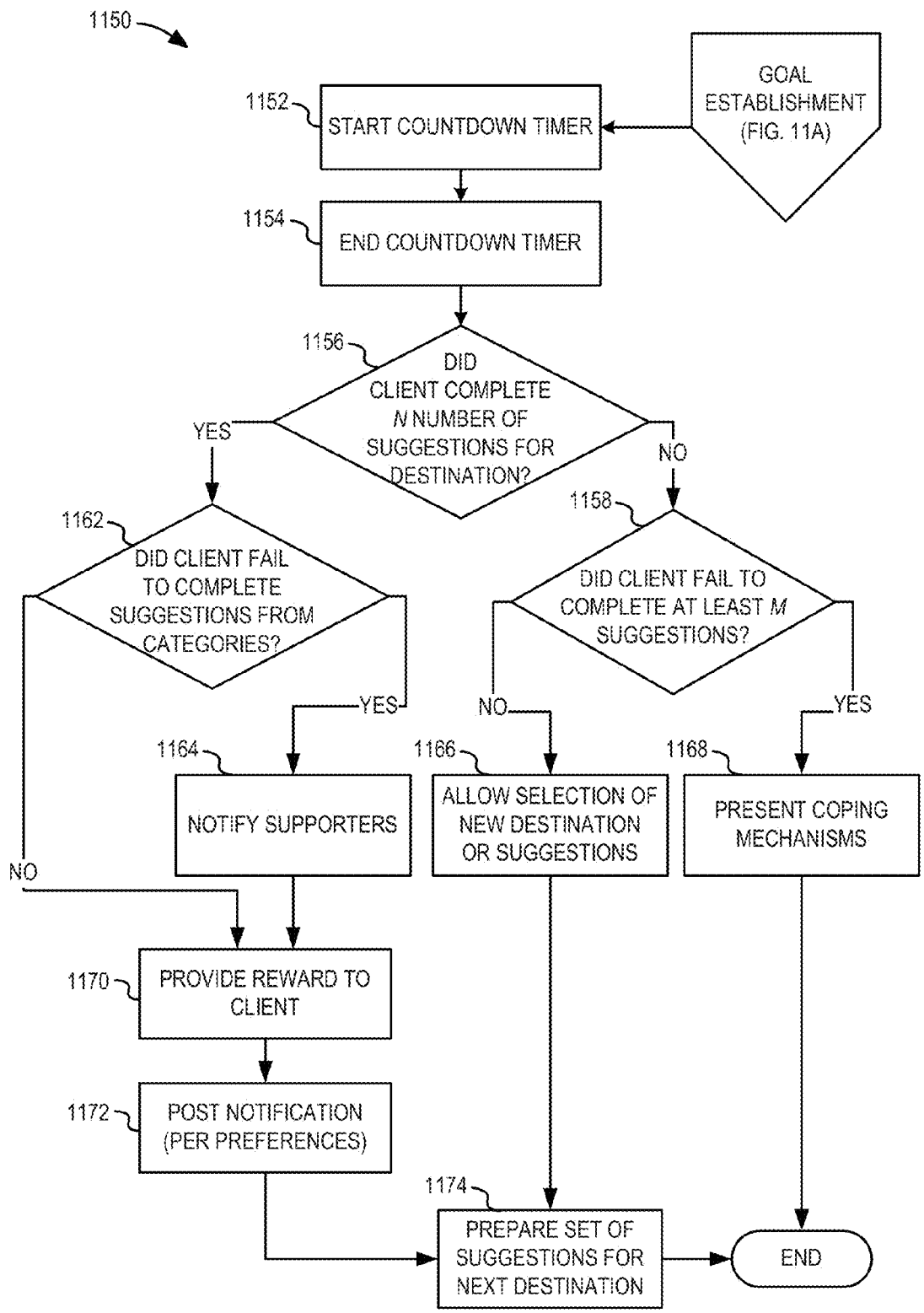
FIG. 11B illustrates an example technique of generating a response to a client based on completion of suggested actions in a goal-based workflow according to an example described herein.

FIG. 11B illustrates an example technique of generating a response to the client 106 based on user completion of suggested actions in a goal-based workflow 1150 according to an example described herein. The countdown timer may be started (operation 1152) and finish (operation 1154). At or around the time the countdown time ends, the number of suggestions that the client 106 completed related to the destination (e.g., a long term or a short term goal) may be determined (decision 1156).

When the client 106 has completed a sufficient number of suggestions to reach the destination, then it may be determined if the client 106 failed to complete suggestions from specific categories (e.g., psychological categories, goal categories, or other categories) (decision 1162). If the client 106 failed to complete a sufficient number of suggestions in a certain category then one or more of the client's supports may be notified (operation 1164). If the client 106 did not fail to complete suggestions from all the categories, or if one or more of the client's supporters have been notified, then the client 106 can be provided with a reward (operation 1170). The reward may be kudos or a suggestion to do a fun activity. Post notifications may be provided as a function of the client's preferences (operation 1172). For example, a post notification may include sending a notification to one or more of the client's supporters that the client 106 has succeeded or a post may be provided to and displayed on a social media website, such as Facebook or Twitter. A set of suggestions may be prepared for the client's next destination (operation 1174).

When the client 106 has not completed a sufficient number of suggestions to reach the destination, then it may be determined if the client 106 failed to complete a certain number (M) of suggestions (decision 1158). If the client 106 did not fail to complete at least M (an integer number greater than zero) suggestions then the user may be allowed to select a new destination or one or more suggestions (operation 1166). A set of suggestions may be prepared for the client's next destination (operation 1174). If the client 106 failed to complete at least M suggestions, one or more coping mechanisms may be presented to the client 106 or supporters of the client 106 (operation 1168).

Supporter Interaction and Workflow Examples

The goal-based workflows may be configured to integrate selection and delivery of suggested content with insight and input from supporters in the supporter network 104. A supporter may be a personal acquaintance of a client, a trained motivator, a dietary professional, a psychologist or other psychological expert, another client facing a similar problem, a random person interested in helping people achieve their goals, or any other person the client 106 may choose to help them achieve their goals. For example, a client may know that they need someone to "be on their case" about completing suggestions and may know somebody who is good at motivating them to complete actions. That person could be a supporter for that client. In another example, a client having trouble eating can have a supporter who is a dietary expert with experience in nutrition and curbing bad eating habits. The supporters may be chosen by the client 106 or assigned to the client 106 by the system. Another user of the application may request to be a supporter for the client 106 and the client 106 may be given an opportunity to either accept or reject the request.

Figure 12A:
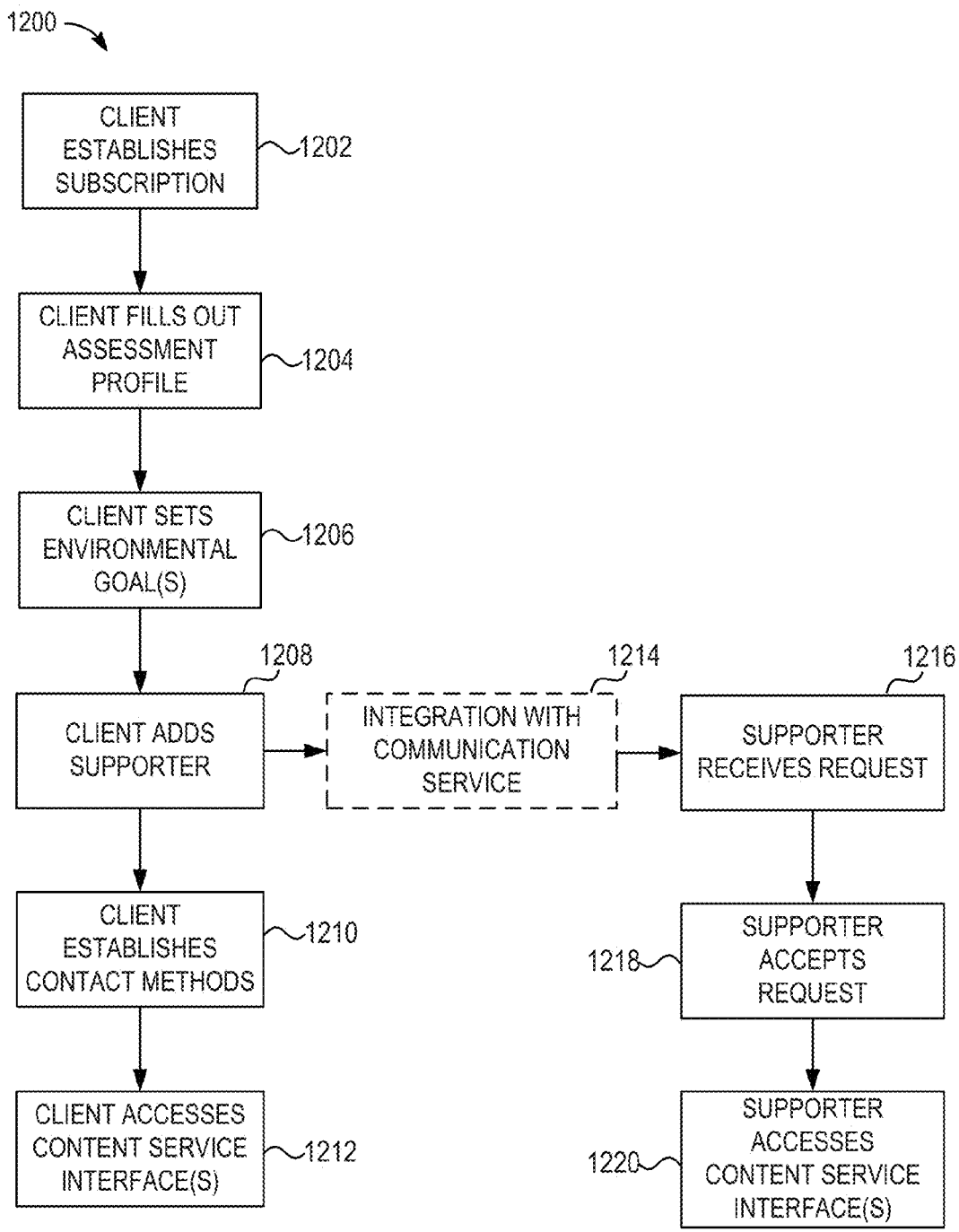
FIG. 12A illustrates a flowchart depicting a workflow for client and supporter interaction in connection with a client content service interface according to an example described herein.

FIG. 12A illustrates a flowchart depicting a workflow 1200 for client and supporter interaction within an information service providing a software or other user-interactive application for clients and supporters. A client may establish a subscription to the application (operation 1202). This may be accomplished by visiting a website or purchasing/downloading software and following steps suggested by the website or software. The client 106 can fill out an assessment profile (operation 1204). The assessment profile may be configured to obtain data 208 from the client 106. The client can set one or more goals (operation 1206). The client can choose supporters, supporters may be recommended to the client 106, supporters may request to work with the client 106, or supporters may be otherwise associated with the client 106 (operation 1208). The client 106 also establishes methods of which they would prefer to be contacted by supporters or the application (operation 1210). The client 106 can access the client content service interface of the application (operation 1212) (e.g., a client content service interface shown in FIG. 13).

When the client 106 adds a supporter (operation 1208), a request may be sent to the supporter. Optionally, this may be accomplished through interaction with the communication interface (operation 1214) (e.g., a communication interface shown in FIG. 13). The supporter may receive the request (operation 1216). Using the application, the supporter may accept the request to become a supporter for the client 106 (operation 1218). The supporter may access the supporter content service interface of the application (e.g., a supporter content service interface shown in FIG. 13) (operation 1220).

Figure 12B:
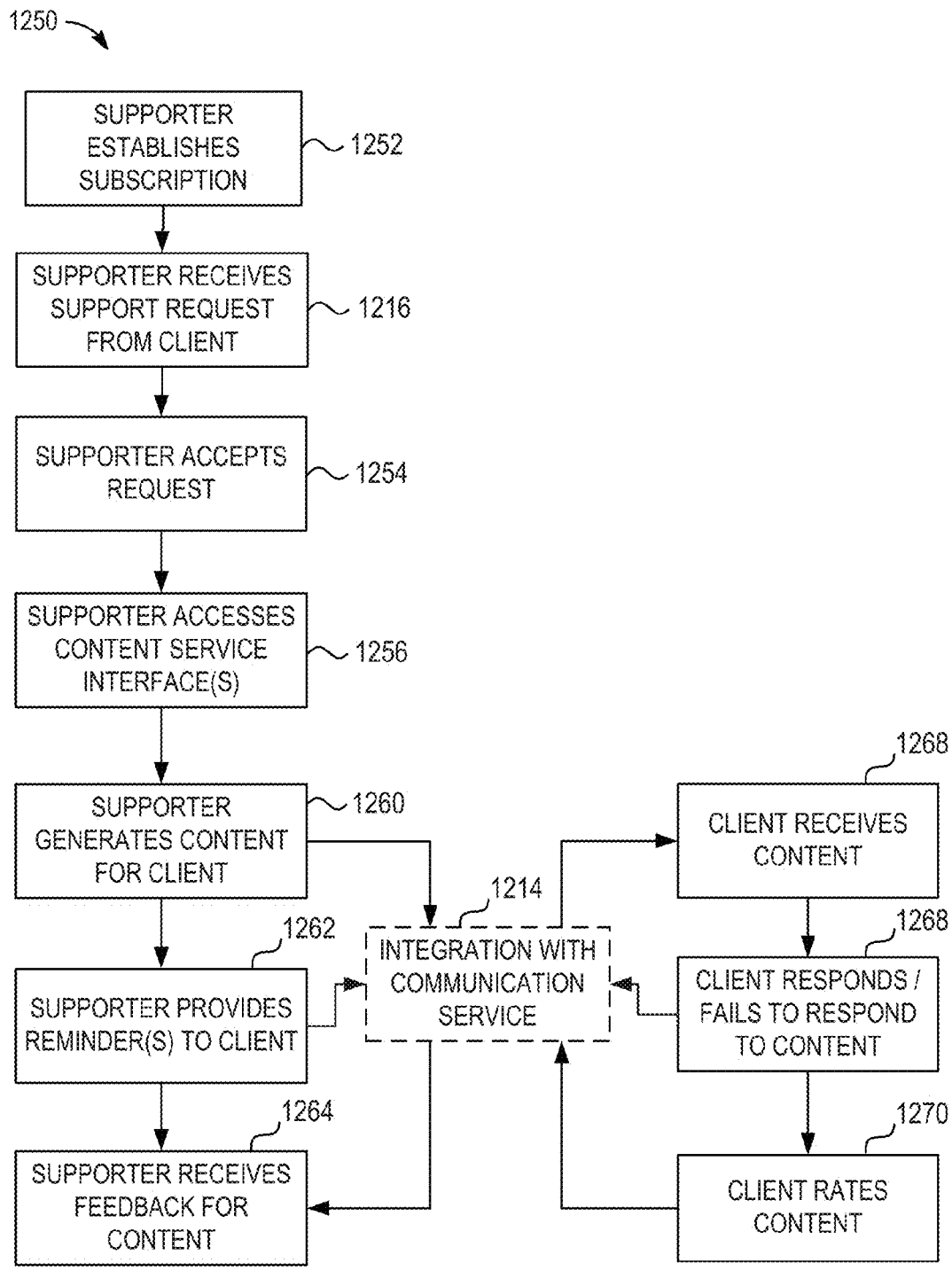
FIG. 12B illustrates a flowchart depicting a workflow for client and supporter interaction in connection with a supporter content service interface according to an example described herein.

FIG. 12B illustrates a flowchart depicting a workflow 1250 for supporter interaction within an information service providing a software or other user-interactive application for clients and supporters. In correspondence with the configuration of FIG. 12A, flowchart 1250 illustrates supporter-based operations to establish a subscription and generate content for communication to supported clients.

In the workflow 1250, a supporter may establish a subscription to the application (operation 1252). This may be accomplished by visiting a website or purchasing/downloading software and following steps suggested by the website or software. The supporter will receive the support request from a client (operation 1216). In response, the supporter will accept the request (operation 1254). The supporter then accesses the content service interface(s) (operation 1256), and uses the interface to generate content for the client (operation 1260). The content is then provided to the client through integration with the communication service (operation 1214).

In connection with the mechanisms provided by the integration with the communication service (operation 1214), the client may receive content from the supporter (operation 1268), and provide a response (or fail to provide a response) to the content (operation 1268). To encourage response to content, the supporter may provide one or more reminders to the client regarding the content and associated actions or goals (operation 1262). The client may also provide a rating of the content (operation 1270). The rating of the content, and appropriate reminders and feedback (operation 1264), may be exchanged through the integration with the communication service (operation 1214).

The supporter may be provided with feedback on a variety of environmental data values of the client, provided in context to transmit meaningful data about the client to the supporter. The environmental data values may include moment-in-time data used to craft informed and relevant selections, including environmental considerations, psychological or physiological considerations, even the weather at the location of the user. Further, the supporter may be able to choose suggested content among available choices and provide guidance to the communication process (such as choosing one option among three suitable options, based on the supporter's understanding of which suggested content is most relevant or would be most well-received by the client).

Figure 13:
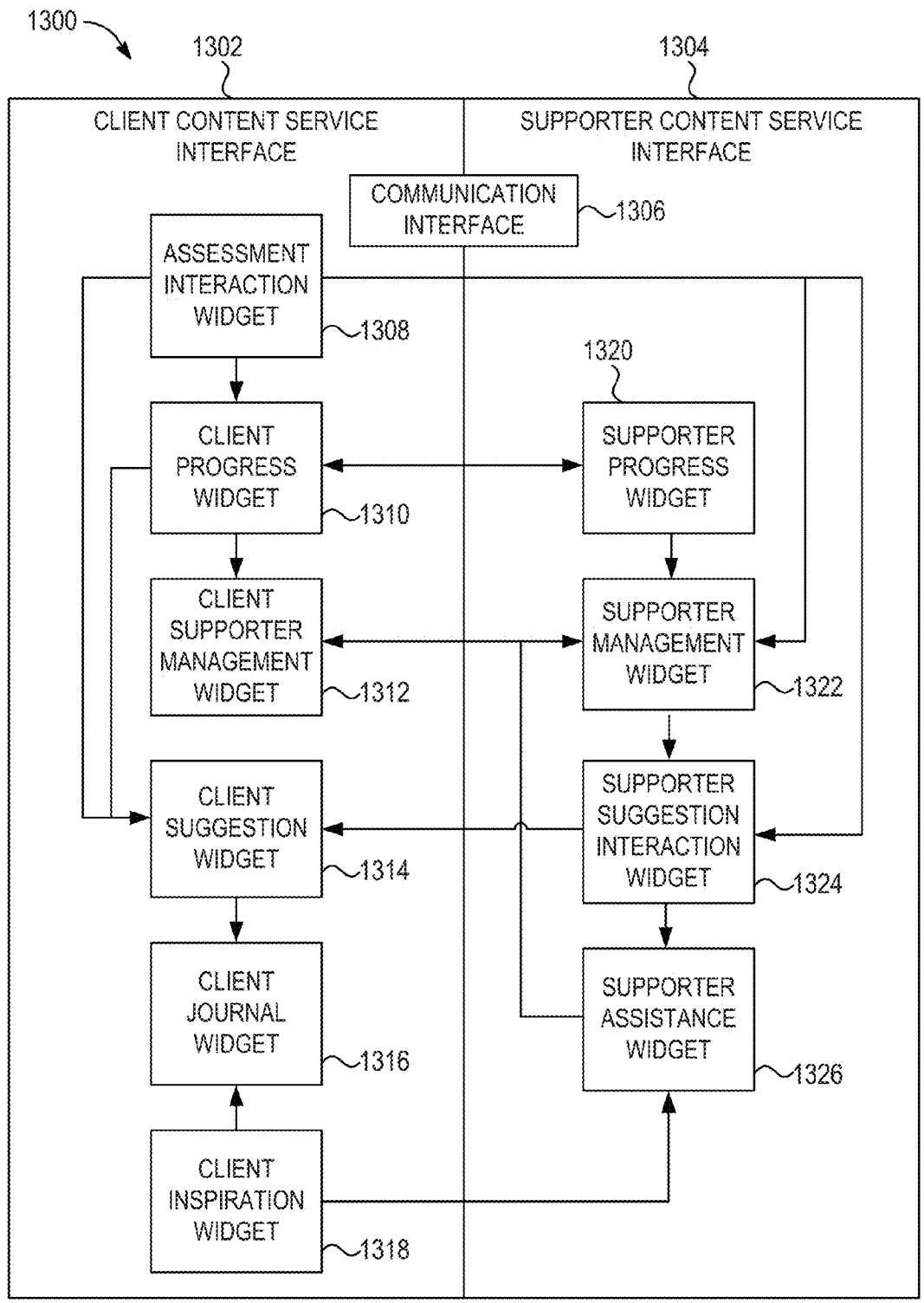
FIG. 13 illustrates a block diagram of interface components for client and supporter interaction within a content service according to an example described herein.

FIG. 13 illustrates a block diagram of interface components 1300 for client and supporter interaction within a content service according to an example described herein. The interface components 1300 may include a client content service interface 1302, a supporter content service interface 1304, or a communication interface 1306 between the client content service interface 1302 and the supporter content service interface 1304.

The client content service interface 1302 may include an assessment interaction widget 1308, a client progress widget 1310, a client supporter management widget 1312, a client suggestion widget 1314, a client journal widget 1316, or a client inspiration widget 1318. The assessment interaction widget 1308 may be communicatively coupled to the client suggestion widget 1314 or the client progress widget 1310. The assessment interaction widget 1308 may be communicatively coupled to the supporter content service interface 1304, such as to a supporter management widget or a supporter suggestion interaction widget 1324 of the supporter content service interface 1304. The assessment interaction widget 1308 may determine an amount of client involvement with the application and may cater the presentation of the suggestions and other messages based on the amount of client involvement.

The client progress widget 1310 may be communicatively coupled to the client supporter management widget 1312 or the client suggestion widget 1314. The client progress widget 1310 may be communicatively coupled to a supporter progress widget 1320 of the supporter content service interface 1304. The client progress widget 1310 may monitor a client's progress towards a goal. The client progress widget 1310 may send other widgets updates regarding the client's progress towards a goal, such as indicating when a suggestion is completed or how many suggestions the client 106 has left to complete before the goal is accomplished.

The client supporter management widget 1312 may be communicatively coupled to a supporter management widget 1322 or a supporter assistance widget 1326 of the supporter content service interface 1304. The client supporter management widget 1322 may be configured to prompt a client for data 208, feedback on the client's opinion of the system, and may send information to the supporter management widget 1322, such as information indicating to the supporter management widget 1322 that a supporter should send a suggestion to the client 106 or that the supporter should send an encouraging message to the client 106.

The client suggestion widget 1314 may be communicatively coupled to a supporter suggestion interaction widget 1324 of the supporter content service interface 1304. The client suggestion widget 1314 may present suggestions to the client 106, which the client 106 may then accept, reject, or ignore. The suggestions presented may be received from the supporter suggestion interaction widget 1324 or content suggestion engine.

The client journal widget 1316 may be communicatively coupled to the client inspiration widget 1318. The client journal widget 1316 may allow the client to have a sort of diary that records their experience(s) interacting with the application. The client journal widget 1316 may prompt the client for entries or may be passive and allow the client to create journal entries as the client desires.

The client inspiration widget 1318 may be communicatively coupled to the supporter assistance widget 1326. The client inspiration widget 1318 may record the reasons that the client 106 is trying to achieve a goal and remind the client 106 about those reasons. The reminders may be random, scheduled, or configured to not appear in some instances, such as when a client indicates that they do not want to receive these reminders.

The supporter content service interface 1304 may include the supporter progress widget 1320, the supporter management widget 1322, the supporter suggestion interaction widget 1324, or the supporter assistance widget 1326. The supporter progress widget 1320 may be communicatively coupled to the supporter management widget 1322. The supporter progress widget 1320 can keep a supporter abreast of how the client 106 is progressing towards the goal.

The supporter management widget 1322 may be communicatively coupled to the supporter suggestion interaction widget 1324. The supporter management widget 1322 may monitor how the supporter interacts with the client 106 and determine whether or not that interaction is effective. These determinations may be sent to the supporter suggestion interaction widget 1324.

The supporter suggestion interaction widget 1324 may be communicatively coupled to the supporter assistance widget 1326. The supporter suggestion interaction widget 1324 may prompt a supporter to send a suggestion, encouraging message, or other content, such as scientific articles or inspirational stories, to the client 106. The supporter suggestion interaction widget 1324 may indicate to the supporter that the supporter should leave the client 106 alone for a specified amount of time (e.g., minutes, hours, days, weeks, etc.).

The supporter assistance widget 1326 may help the supporter choose suggestions, personalize suggestions, or draft other messages to the client 106. The supporter assistance widget 1326 may help the supporter navigate the application or get in contact with other supporters, such as other supporters helping clients with similar goals or lifestyles.

The types and amount of communications between the various widgets (and between the client and supporter) may be customized, to be expanded or narrowed with user preferences. For example, various privacy settings and preferences may be set by a user to share more or less information about specific activities or conditions, or to send and receive more or less information from particular users. Many of the data points can be customized to different levels to control the types and amount of interactions.

Figure 14:
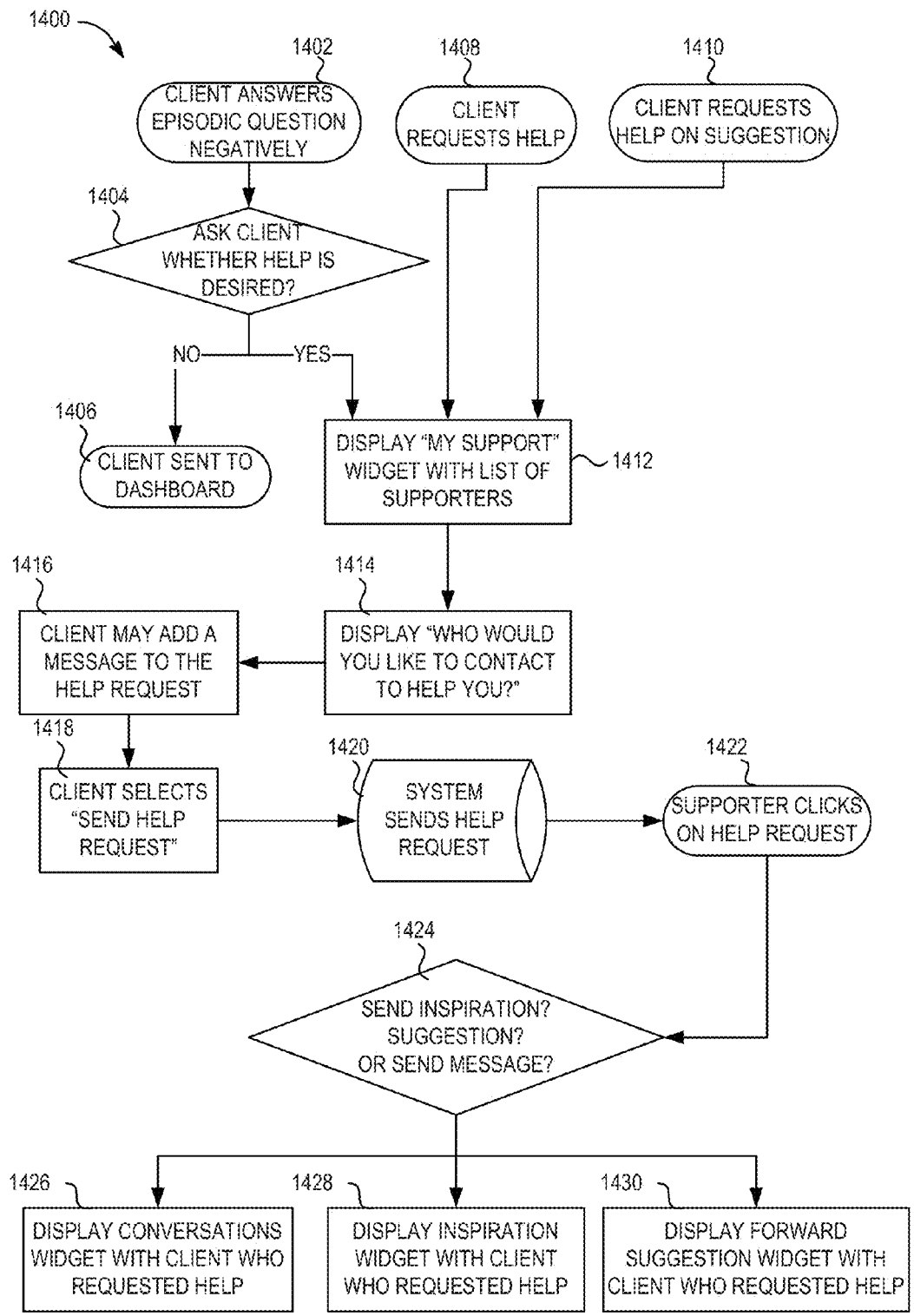
FIG. 14 illustrates a flowchart of interaction between a client and a supporter in a goal-based workflow according to an example described herein.

FIG. 14 illustrates a flowchart 1400 of supporter interaction with a client in a goal-based workflow according to an example described herein. When a client answers an episodic question (e.g., a question to the client 106 that is designed to obtain or measure the psychological state of the client 106) negatively, such as by responding "terrible", "not good", or the like to an episodic question "How are you today?" (operation 1402), the application can ask the client 106 if they would like help (operation 1404). When the client 106 indicates that they do not want help, the client 106 can be sent to the dashboard (operation 1406) (further described below with reference to dashboard 1570 in FIG. 15B).

When the client 106 indicates that they do want help, such as by answering "Yes" to the question "would you like help?" (operation 1408), requesting help using the client supporter management widget 1312, or requesting help on a link provided on a suggestion (operation 1410), then the client 106 may be presented with a list of supporters. The list of supporters may be provided from list of supporters from the client supporter management widget 1312 (operation 1412). The client 106 may be asked who they would like to contact to help them (operation 1414). When the client 106 requests help using a link or button on a suggestion, such as an accepted suggestion, that was sent to the client 106 from a supporter, then the client 106 may be directed (e.g., automatically), to the supporter that sent the suggestion. The client 106 may select one or more supporters, or groups of supporters to help. The client 106 may add a message to a help request (operation 1416) and the help request may be sent to the respective supporter(s), such as by the client 106 selecting a "send request" option (operation 1418). The application may send the help request (along with any messages the client 106 added) to the selected supporters (operation 1420). The help request may be accompanied by notifications that are configured to alert the supporter, such as a text, email, or other notification, that the client 106 is looking for help.

The supporter can click on or otherwise interact with the help request (operation 1422). The application may prompt the supporter to take an action (decision 1424) by asking if the supporter if he or she would like to send an inspirational message, suggestion, other message, or if they would like to contact the client 106 directly. If the supporter would like to contact the client 106 directly then a conversation box or other conversations widget can be opened for the supporter to chat with the client 106 (operation 1426). If the supporter would like to send inspiration to the client 106, the client inspiration widget 1318 may be accessed so that the supporter can determine what inspires the client 106 (operation 1428). If the supporter would like to forward a suggestion produced by the information system, a supporter suggestion interaction widget 1324 or other suggestion forwarding widget may be accessed to forward suggestions from the supporter to the client 106 (operation 1430).

Figure 15A:
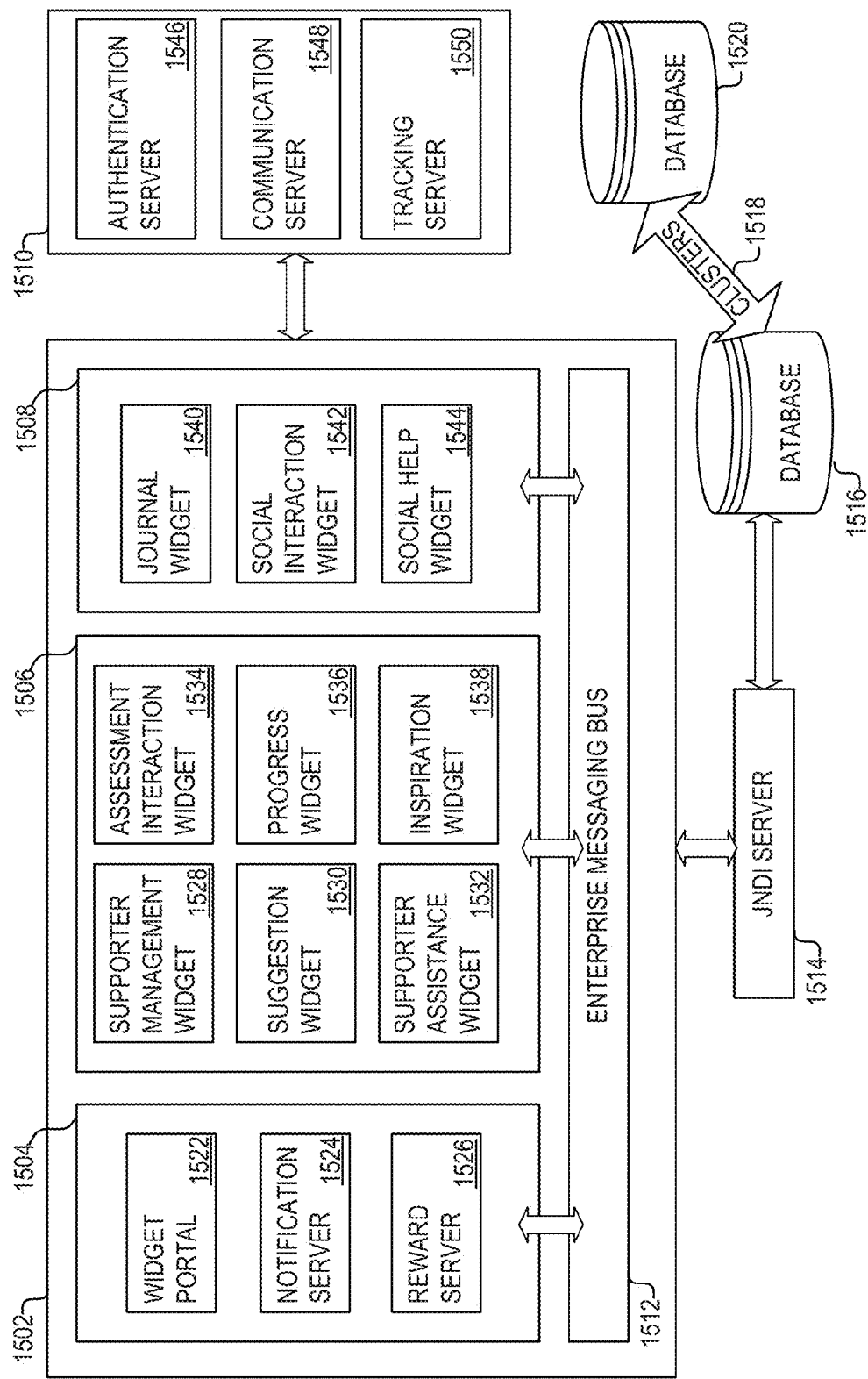
FIG. 15A illustrates a block diagram of data serving and processing components within an information service configured for facilitating goal-based workflows according to an example described herein.

FIG. 15A illustrates a block diagram of data serving and processing components within an information service content server 1502 configured for facilitating goal-based workflows according to an example described herein. The information service content server 1502 may be structured to include a core functionality server 1504, a goal functionality server 1506, and a social functionality server 1508. The information service content server communicates with each of the servers 1504, 1506, 1508 through an enterprise messaging bus 1512, with each interaction exchanging one or more messages. The information service content server 1502 also may be in communication with external servers 1510, and a Java Naming and Directory Interface (JNDI) server 1514.

The external servers 1510 may include an authentication server 1546 used for obtaining authentication to various data services and content during the workflow, a communication server 1548 used for facilitating communications during the workflow, and a tracking server 1550 used for tracking various user actions and content provisions during the workflow.

In the information service content server 1502, the core functionality server 1504 contains various servers including a widget portal 1522 for displaying and rendering widgets in connection with workflow activities, a notification server 1524 for generating and outputting notifications within the workflow activities, and a reward server 1526 for generating and outputting rewards in response to the workflow activities.

The goal functionality server 1506 includes various user interface widgets used for generation of appropriate user interface displays and interactions. These include a supporter management widget 1528 for management of supporters and supporter relationships; a suggestion widget 1530 for the management and output of various suggestions from the information system; a supporter assistance widget 1532 for the initiation and response to supporter assistance actions; an assessment interaction widget 1534 for the display and receipt of input for user assessments within the workflow; a progress widget 1536 for outputting a display of progress within the workflow; an inspiration widget 1538 for outputting inspiration content within the workflow.

The social functionality server 1508 includes various user interface widgets used for appropriate user interface displays and interactions in connection with social activities. These include a journal widget 1540 for the receipt of user journal content in connection with the workflow; a social interaction widget 1542 used for facilitating social interaction, messaging, and other social exchanges during activities in the workflow; and a social help widget 1544 used for requesting help for activities in the workflow from social connections.

Requests for information and like messages from information service content server 1502 may be exchanged with one or more databases 1516 through the use of a JNDI server 1514 in operable communication with the information service content server 1502. Various clusters 1518 of relevant data for particular users, activities, or supporters may be communicated from additional databases 1520.

Figure 15B:
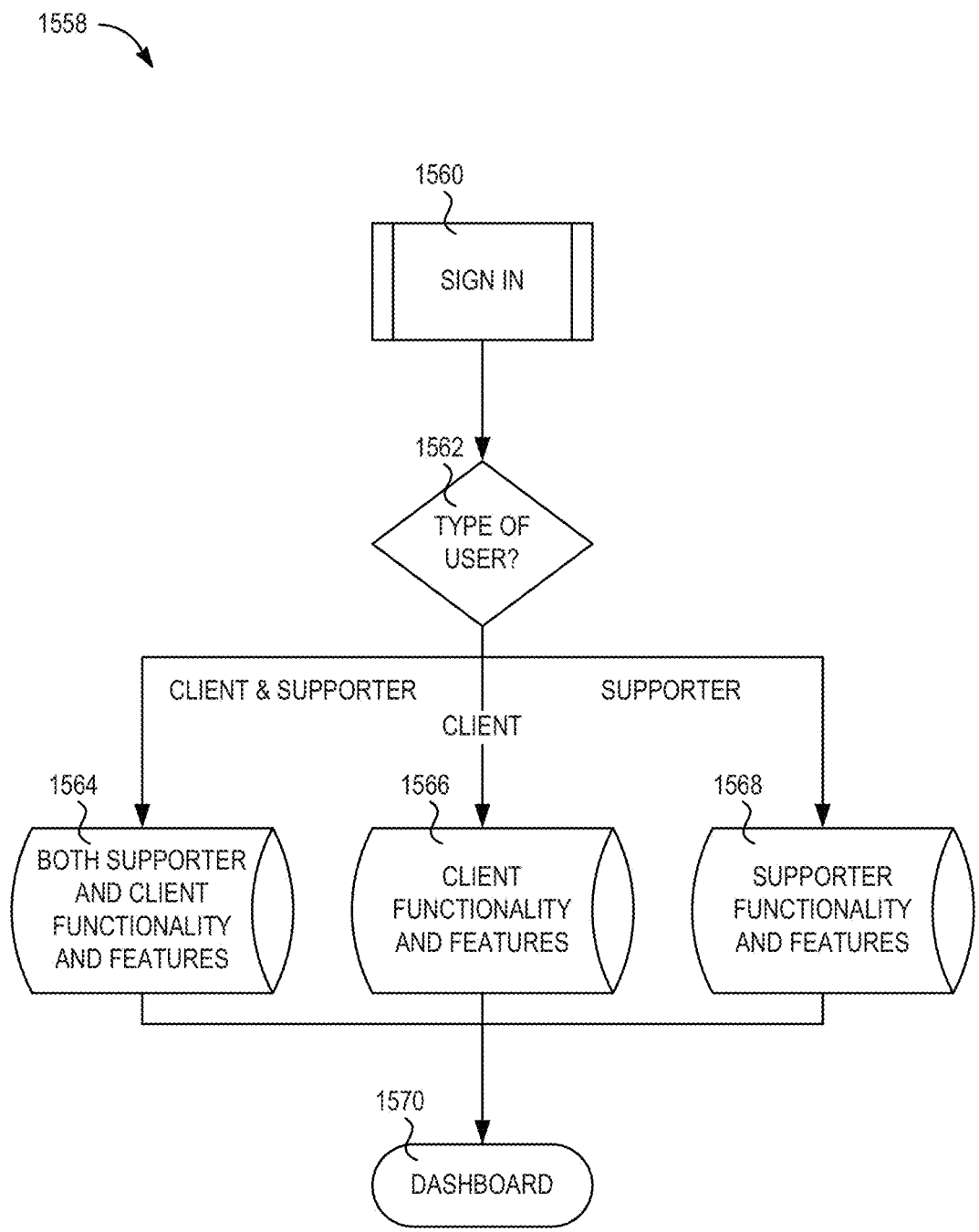
FIG. 15B illustrates a flowchart of data functionality and feature components available to a client and a supporter within an information service according to an example described herein.

FIG. 15B illustrates a flowchart 1558 of data functionality and feature components available within an information service according to an example described herein. A client or supporter may access the functionality and feature components through sign in to the information service (data operation 1560). The type of user that has signed in can be determined (decision 1562). If the user is both a client and a supporter, the supporter and client functionality and features may be loaded for viewing and interaction (using data set 1564). If the user is just a client, then the client functionality and features may be loaded for viewing and interaction (using data set 1566). If the user is just a supporter, then the supporter functionality and features may be loaded for viewing and interaction (using data set 1568). Client functionality and features (from data set 1566) may include the widgets provided in the client content service interface 1302 (described with reference to FIG. 13). Supporter features and functionality (from data set 1568) may include the features and functionality of the widgets provided in the content service interfaces 1302, 1304. A dashboard 1570 that displays the client or supporter features and provides the client or supporter functionality to the respective user may be displayed to the user.

Computing System Architectures and Example Implementations

Figure 16:
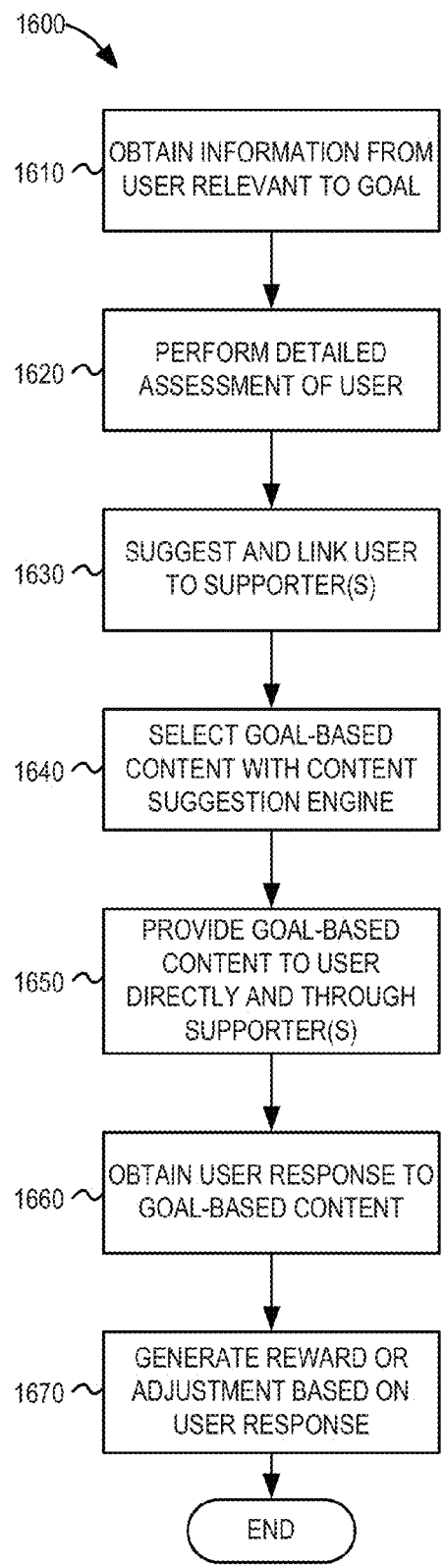
FIG. 16 illustrates an example method implementing a goal-based workflow for effecting behavior change using an information system according to an example described herein.

FIG. 16 illustrates a flowchart 1600 of an example implementation method of a goal-based workflow for effecting behavior change using the information system 100 according to an example described herein. The particular sequence depicted in the flowchart 1600 is provided as a non-limiting example, and illustrates a workflow involving an initial content selection and content display. Other aspects of the workflow described herein may include other portions of interaction with the information systems and associated graphical user interfaces.

The flowchart 1600 illustrates a workflow of information system operations originating with various data collection operation steps. These data collection steps are designed to continually adapt and learn from users, considering the current state or mood of the user, while refreshing data stored in the system as appropriate. The data collection steps may include obtaining information relevant to goal from a user (operation 1610) and performing a detailed assessment of the user (operation 1620). The information relevant to the goal may include a self-selection of the overall goal or goals, or other mechanisms such as questionnaires to filter the goal. The detailed assessment may include a psychological assessment or other profiling assessments.

The information system may operate to suggest one or more supporters, and link the user to the suggested supporters (operation 1630). The supporter link may be created in response to user acceptance provided with automatic criterion or manual selection.

The content for the user from the information system may be selected and delivered, through operations to select goal-based content with a content suggestion engine (operation 1640), and provide the goal-based content to the user directly or through one or more supporters (operation 1650).

The response to the content (including any suggested action and the results of the response to the suggestion action) may be obtained from the user (operation 1660). Based on the user response and the particular action performed or not performed, a reward or adjustment may be generated in the information system (operation 1670). This may include the refinement of content and suggested action selections (and the exclusion of particular suggested actions).

Although some of the previous examples were provided with reference to specific medical conditions and human activities such as weight loss and weight loss-related activities, it will be understood that the applicability of the present system may apply to a variety of human behaviors and goal-based activities in medical and non-medical settings. A non-limiting, illustrative listing of the applicability of the present techniques to medical conditions includes weight loss, smoking cessation, addition recovery, chronic illness management, psychological support, and the like. Another non-limiting, illustrative listing of the applicability of the present techniques includes application to non-medical settings such as education and learning, sport activities and sports training, and other scenarios where human activity is correlated to some goal or achievement.

Figure 17:
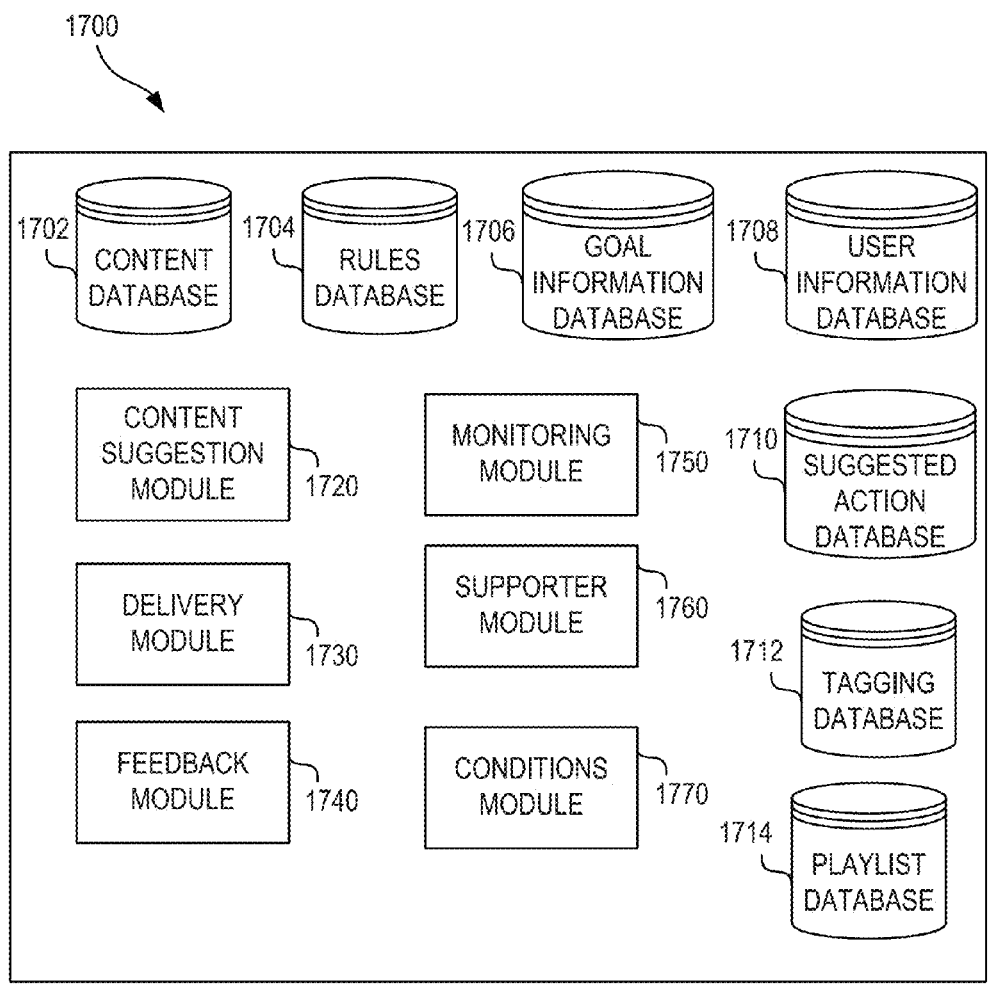
FIG. 17 illustrates an example system configuration of an information system arranged to provide suggested content according to an example described herein.

FIG. 17 illustrates an example of a system configuration of an information system 1700 configured to provide content.

The information system 1700 may include a content database 1702, a rules database 1704, a goal information database 1706, a user information database 1708, a suggested action database 1710, and a tagging database 1712.

The content database 1702 may include information from external sources, such as the supporter network 104, a professional expert working in a field relevant to a goal 204, other databases, or a combination thereof, among others. The rules database 1704 may include rules for formatting and providing personalized suggestions (e.g., suggested actions) to the client 106. Such rules may include timing restrictions, wording suggestions or restrictions, or suggested action restrictions (e.g., a suggestion with a certain tag should not be presented to a specific client, such as the client 106).

The goal information database 1706 may include data relevant to getting the client 106 to achieve a particular goal 204. The goal information may include certain activities that are a prerequisite to achieving a goal 204 (e.g., running a marathon requires the client to run to achieve the goal 204), recommended for achieving the goal 204 (e.g., stretching muscles and breathing exercises are helpful, but not essential, in training for a marathon), fun (e.g., things to keep the client 106 in a positive state of mind or reward the client 106 for their hard work or achievements), or a combination thereof, among others.

The user information database 1708 may include information gained from questionnaires or learned through the client 106 or supporters in the supporter network 104 using the system. The user information database 1708 may include information about all users of the system including supporters, clients 106, administrators of the system, or potential clients, among others. The suggested action database 1710 may include suggestions including pre statements, action statements, and post statements. The suggested action database 1710 may also include a record of which client has completed which suggestion, when the client 106 completed the suggestion, or how long it has been since the system recommended that suggestion to the client 106. The tagging database 1712 may include a record of all the tags and tagging relationships that have been created for suggestions, playlists, or programs, and which suggestions, programs, or playlists the tag is associated with.

While FIG. 17 shows six separate databases 1702-1712, the information contained within the databases may be contained within any number of databases. For example, the information in the suggested action and tagging databases 1710, 1712 may be combined into a single database.

The information system 1700 may include one or more modules including a content suggestion module 1720, a delivery module 1730, a feedback module 1740, a monitoring module 1750, a supporter module 1760, or a conditions module 1770. The content suggestion module 1720 may receive suggestions or have access to the suggested action database 1710. The content suggestion module 1720 may include filter(s) and the weight(s), such as to allow the content suggestion module 1720 to filter, prioritize, or present suggestions to the client 106.

The delivery module 1730 may present at least one suggestion or message to the supporter network 104 or the client 106, such as at a certain relevant time. The delivery module 1730 may be configured to modify or amend the suggestion or message that is delivered so as to be appropriate for the client 106. Such a configuration may make the client 106 more likely to complete the suggestion.

The feedback module 1740 may be configured to receive feedback about suggestions from a client 106, process the feedback, and send the processed feedback to the user information database 1708, rules database 1704, content database 1702, or suggested action database 1710.

The monitoring module 1750 may be configured to monitor a client's progress towards their goal(s) 204, a client's progress on completing a suggestion, program, or playlist, and may provide the delivery module 1730 with information relevant to what messages (e.g., prompts, reminders, or encouragements) should be sent to the client 106.

The supporter module 1760 may be configured to provide the supporter network 104 with the ability to make suggestions for a suggestion to present to the client 106, provide information relevant to getting the client 106 to their goal 204 (e.g., likes, dislikes, barriers 214, or incentives 216 for the client 106, etc.), suggest messages to send to the client 106 that may be modified by the delivery module 1730, or suggest tags that should be associated with the client 106.

The conditions module 1770 may be configured to maintain relevant information from the ecosystem of conditions 212 and the client data conditions 108 that are relevant to the selection and delivery of relevant content. This may include direct or derived contextual data, or data relevant to barriers and incentives. For example, the contextual information maintained in conditions module 1770 may provide input for rules to express the conditions to deliver content to the proper user, at the proper time, in the proper context, and with the proper communication medium.

Figure 18:
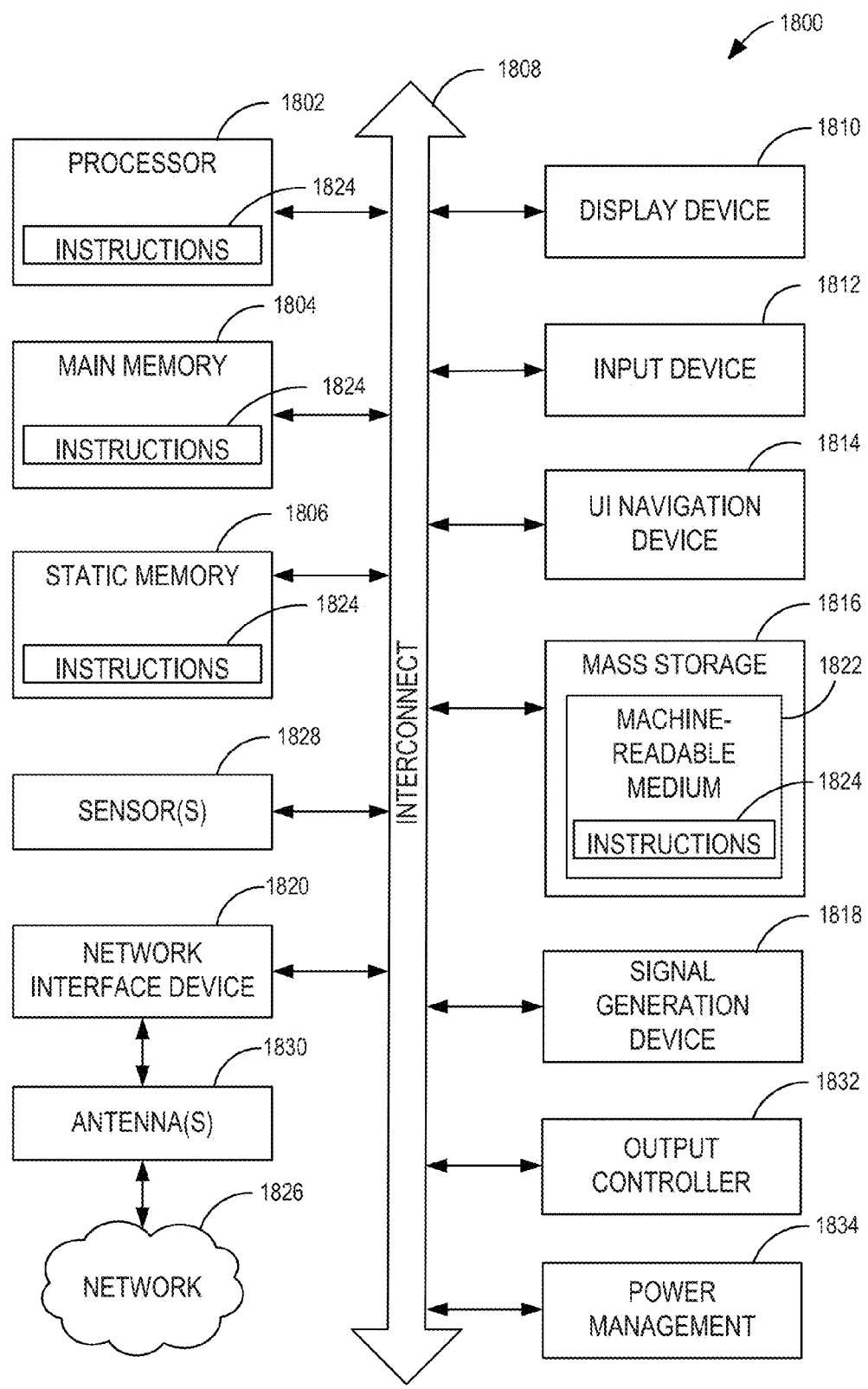
FIG. 18 illustrates an example of a computer system to implement techniques and system configurations according to an example described herein.

FIG. 18 is a block diagram illustrating an example computer system machine upon which any one or more of the methodologies herein discussed may be run. Computer system 1800 may be embodied as a computing device, providing operations of the suggestion engine 102, supporter network 104, information system 100 or interface components 1300 (from FIGS. 1 and 13), or any other processing or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a set-top box (STB), a gaming console, a Personal Digital Assistant (PDA), a mobile telephone or smartphone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 1800 includes a processor 1802 (e.g., a central processing unit (CPU), a graphics processing unit (GPU) or both), a main memory 1804 and a static memory 1806, which communicate with each other via an interconnect 1808 (e.g., a link, a bus, etc.). The computer system 1800 may further include a video display unit 1810, an alphanumeric input device 1812 (e.g., a keyboard), and a user interface (UI) navigation device 1814 (e.g., a mouse). In one embodiment, the video display unit 1810, input device 1812 and UI navigation device 1814 are a touch screen display. The computer system 1800 may additionally include a storage device 1816 (e.g., a drive unit), a signal generation device 1818 (e.g., a speaker), an output controller 1832, a power management controller 1834, and a network interface device 1820 (which may include or operably communicate with one or more antennas 1830, transceivers, or other wireless communications hardware), and one or more sensors 1828, such as a GPS sensor, compass, location sensor, accelerometer, or other sensor.

The storage device 1816 includes a machine-readable medium 1822 on which is stored one or more sets of data structures and instructions 1824 (e.g., software) embodying or utilized by any one or more of the methodologies or functions described herein. The instructions 1824 may also reside, completely or at least partially, within the main memory 1804, static memory 1806, and/or within the processor 1802 during execution thereof by the computer system 1800, with the main memory 1804, static memory 1806, and the processor 1802 also constituting machine-readable media.

While the machine-readable medium 1822 is illustrated in an example embodiment to be a single medium, the term "machine-readable medium" may include a single medium or multiple media (e.g., a centralized or distributed database, and/or associated caches and servers) that store the one or more instructions 1824. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1824 may further be transmitted or received over a communications network 1826 using a transmission medium via the network interface device 1820 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Other applicable network configurations may be included within the scope of the presently described communication networks. Although examples were provided with reference to a local area wireless network configuration and a wide area Internet network connection, it will be understood that communications may also be facilitated using any number of personal area networks, LANs, and WANs, using any combination of wired or wireless transmission mediums.

The embodiments described above may be implemented in one or a combination of hardware, firmware, and software. For example, the information system 100, 1700 may include or be embodied on a server running an operating system with software running thereon. While some embodiments described herein illustrate only a single machine or device, the terms "system", "machine", or "device" shall also be taken to include any collection of machines or devices that individually or jointly execute a set (or multiple sets) of instructions to perform any one or more of the methodologies discussed herein.

Embodiments may also be implemented as instructions stored on a computer-readable storage device or storage medium, which may be read and executed by at least one processor to perform the operations described herein. A computer-readable storage device or storage medium may include any non-transitory mechanism for storing information in a form readable by a machine (e.g., a computer). For example, a computer-readable storage device or storage medium may include read-only memory (ROM), random-access memory (RAM), magnetic disk storage media, optical storage media, flash-memory devices, and other storage devices and media. In some embodiments, the electronic devices and computing systems described herein may include one or more processors and may be configured with instructions stored on a computer-readable storage device.

Examples, as described herein, may include, or may operate on, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Additional examples of the presently described method, system, and device embodiments include the following, non-limiting configurations. Each of the following non-limiting examples can stand on its own, or can be combined in any permutation or combination with any one or more of the other examples provided below, in the claims, or elsewhere in the present disclosure.

A first example can include the subject matter (such as an apparatus, a method, a means for performing acts, or a machine readable medium including instructions that, when performed by the machine, that can cause the machine to perform acts), for facilitating selection of goal-based content from an information system, including: obtaining contextual user information maintained in an information system relevant to a health goal for a human user; presenting an assessment prompt to the human user, by using a graphical user interface to the information system; performing an ongoing assessment of behavior of the human user to measure progress of the human user to achieving the health goal, by using input from the human user provided in the assessment prompt; selecting content maintained in the information system relevant to activity for achieving the health goal, by using the contextual user information and the measured progress of the human user; and presenting the content relevant to achieving the health goal to the human user, by using the graphical user interface.

A second example can include, or can optionally be combined with the subject matter of the first example, to include subject matter (such as an apparatus, a method, a means for performing acts, or a machine readable medium including instructions that, when performed by the machine, that can cause the machine to perform acts), for an information system, including: a user information database storing behavior and assessment information for a human subject; a content database storing context-sensitive content items available to be provided to the human subject, the context-sensitive content items being relevant to attainment of an overall goal by the human subject; a content suggestion module implemented using a processor, the content suggestion module configured for selection of suggested content from the context-sensitive content items in the content database; and a content delivery module implemented using the processor, the content delivery module configured to electronically provide the suggested content to the human subject at a determined timing and to modify the suggested content to increase relevance to the human subject; wherein the suggested content includes a suggested action for performance by the human subject, the suggested action being relevant to the attainment of the overall goal by the human subject.

A third example can include, or can optionally be combined with the subject matter of one or any combination of the first and second example, to include subject matter (such as an apparatus, a method, a means for performing acts, or a machine readable medium including instructions that, when performed by the machine, that can cause the machine to perform acts), for an information system, configured to: generate a client content service interface for display within a graphical user interface accessible by a client user to: capture an assessment of the client user; measure progress of the client user towards a health goal using results of the assessment; receive an interaction from a supporter user related to the health goal; and provide suggested content related to the health goal to encourage progress of the client user towards the health goal, the suggested content obtained from an information system; generate a supporter content service interface for display within a graphical user interface accessible by the supporter user to: indicate the progress of the client user towards the health goal; establish the interaction between the supporter user and the client user related to the health goal; and provide additional suggested content for inclusion with the suggested content related to the health goal.

The following claims are hereby incorporated into the detailed description, with each claim and identified combination of claims standing on its own as a separate example.

What is claimed is:

1. A method for facilitating selection of goal-based content from an electronic information system, the method comprising electronic operations performed by at least one computing machine having at least one hardware processor and at least one memory, with the electronic operations comprising:
    obtaining contextual user information maintained in the electronic information system relevant to a health goal for a client user, wherein progress towards achieving the health goal is obtained through performance of a plurality of real-world activities, wherein the contextual user information tracks a plurality of user-relevant tags associated with characteristics of the client user;
    collecting input in response to at least one natural language inquiry to the client user related to at least one prior activity of the plurality of real-world activities;
    performing an ongoing assessment of behavior of the client user to measure progress of the client user towards achieving the health goal, by analyzing the input from the client user collected in the assessment prompt to determine at least one particular user-relevant tag for tracking in the plurality of user-relevant tags, the at least one particular user-relevant tag determined based on relevancy of the tag to the ongoing assessment of behavior of the client user;
    selecting a particular activity of the plurality of real-world activities for performance by the client user using the contextual user information maintained in the electronic information system, the particular activity being selected for the client user based on whether the particular activity is associated with at least one of the plurality of user-relevant tags and whether the particular activity is likely to be performed by the client user;
    selecting content maintained in the electronic information system relevant to performance of the particular activity to encourage progress towards achieving the health goal, the content being selected from the electronic information system by using the contextual user information and the measured progress of the client user, wherein the content is associated with the at least one particular user-relevant tag determined from the ongoing assessment;
    generating a client content service interface for display within a graphical user interface accessible by the client user to present the content relevant to achieving the health goal to the client user, wherein a presentation style and a delivery type of presenting the content is performed using the contextual user information maintained in the electronic information system; and
    generating a supporter content service interface for display within a graphical user interface accessible by a supporter user to assist the health goal of the client user, wherein the graphical user interface accessible by the supporter user is designed to: indicate the progress of the client user towards the health goal, establish an interaction between the supporter user and the client user related to the health goal, and provide additional suggested content for inclusion with suggested content related to the health goal.

2. The method of claim 1, wherein obtaining contextual user information from the client user includes performing a psychological and physiological assessment of the client user, by using an assessment questionnaire presented to the client user with the graphical user interface; and
    wherein presenting the assessment prompt to the client user includes presenting at least one question to query the client user in the assessment prompt about the at least one prior activity, the presenting of the at least one question matching a communication style determined from the psychological and psychological assessment of the client user.

3. The method of claim 1, wherein the content relevant to performance of the particular activity is tagged with the at least one particular user-relevant tag that corresponds to at least one behavior change attribute of behavior by the client user, and
    wherein selecting the content relevant to performance of the particular activity includes use of the at least one behavior change attribute to select the content, the at least one behavior change attribute determined from the ongoing assessment of behavior.

4. The method of claim 1, wherein the electronic information system links the client user with at least one supporter user in a social network; and wherein the content relevant to achieving the health goal from the electronic information system is delivered to the client user at least in part through communications initiated by the at least one supporter user.

5. The method of claim 4, wherein the content relevant to achieving the health goal from the electronic information system is supplemented by content from the at least one supporter user; and wherein the at least one supporter user receives communications including at least one measurement of the progress of the client user to achieving the health goal.

6. The method of claim 1, the electronic operations further comprising:

capturing a response, from the client user, to the content relevant to achieving the health goal; and changing the content relevant to achieving the health goal in response to the captured response and the ongoing assessment of behavior.

7. The method of claim 6, the electronic operations further comprising:

presenting a reward for the client user for the response to the content relevant to achieving the health goal, based on the response being an indication of completion of a real-world activity related to the health goal.

8. The method of claim 1, the electronic operations further comprising:

presenting a reward for the client user based on a determination of completion of a real-world activity related to the health goal, wherein the reward for the client user is at least one of: a reward for redemption with a charitable organization, a reward for redemption in a virtual game, or a reward for redemption of an object related to achievement of the health goal.

9. The method of claim 1, wherein the health goal is related to a medical condition of the client user, and wherein the content relevant to achieving the health goal includes information relating to performance of multiple activities of the plurality of real-world activities by the client user.

10. The method of claim 1, wherein the graphical user interface is presented by at least one of a website or a software application, wherein the electronic information system is a subscription-based information system used to deliver information related to achieving the health goal, and wherein the contextual user information is provided by the client user at least in part during establishment of a subscription with the subscription-based information system.

11. The method of claim 1, wherein performing the ongoing assessment of behavior of the client user to measure progress of the client user to achieving the health goal, further includes using data collected from a monitoring device.

12. An electronic information system, comprising:

at least one hardware processor;

at least one memory;

a user information database implemented using the hardware processor and the memory, the user information database configured to store contextual user information including behavior and assessment information for a human subject, wherein the contextual user information tracks a plurality of user-relevant tags associated with characteristics of a human subject;

a content database implemented using the processor and the memory, the content database configured to store context-sensitive content items available to be provided to the human subject, the context-sensitive content items being relevant to attainment of an overall health goal by the human subject, wherein progress towards attainment of the overall health goal for the human subject is obtained through performance of a plurality of real-world activities;

a content suggestion module implemented using the processor and the memory, the content suggestion module configured to select suggested content from the context-sensitive content items in the content database, by operations that:

perform an ongoing assessment of behavior of the human subject to measure progress of the human subject towards achieving the health goal, by analysis of the input from the human subject provided collected in the assessment prompt to determine at least one particular user-relevant tag for tracking in the plurality of user-relevant tags, the at least one particular user-relevant tag determined based on relevancy of the tag to the ongoing assessment of behavior of the human subject;

select a particular activity of the plurality of real-world activities for performance by the human subject using the contextual user information maintained in the electronic information system, the particular activity being selected for the human subject based on whether the particular activity is associated with at least one of the plurality of user-relevant tags and whether the particular activity is likely to be performed by the human subject; and select content maintained in the electronic information system relevant to performance of the particular activity to encourage progress towards achieving the health goal, the content being selected from the electronic information system by using the contextual user information and the measured progress of the human subject, wherein the content is associated with the at least one particular user-relevant tag determined from the ongoing assessment; and a content delivery module implemented using the processor and the memory, the content delivery module configured to present the content relevant to achieving the health goal to the human subject, wherein a presentation style and a delivery type of presenting the content is performed using the contextual user information maintained in the electronic information system;

a monitoring module implemented using the processor and the memory, the monitoring module configured to electronically monitor progress of the human subject towards the overall health goal and the performance of the particular activity by the human subject;

a feedback module implemented using the processor and the memory, the feedback module configured to electronically receive feedback from the human subject related to the performance of the particular activity by the human subject, and feedback from the human subject related to the progress of the human subject towards the overall goal; and a supporter module implemented using the processor and the memory, the supporter module configured to:

electronically communicate with at least one human supporter connected to the human subject in a social network;

receive at least one proposed suggestion from the information system;

enable a selection, by the at least one human supporter, of the particular activity from the at least one proposed activity;

enable the at least one human supporter to initiate communications to the human subject to deliver the content relevant to achieving the health goal; and communicate to the supporter the progress of the human subject towards the goal and achievement of the particular activity by the human subject.

13. The system of claim 12, further comprising:

a rules database implemented using the processor and the memory, the rules database configured to store rules related to selection of the context-sensitive content items and achievement of the particular activity by the human subject, wherein the rules are used by the content suggestion module to determine relevancy to the attainment of the overall goal by the human subject; and a conditions module implemented using the processor and the memory, the conditions module configured to control selection of the context-sensitive content items to match at least one data condition specified by the human subject.

14. An electronic information system, comprising:

at least one hardware processor;

at least one memory;

a user information database implemented using the hardware processor and the memory, the user information database configured to store contextual user information including behavior and assessment information for a human subject, wherein the contextual user information tracks a plurality of user-relevant tags associated with characteristics of a human subject;

a content database implemented using the processor and the memory, the content database configured to store context-sensitive content items available to be provided to the human subject, the context-sensitive content items being relevant to attainment of an overall health goal by the human subject, wherein progress towards attainment of the overall health goal for the human subject is obtained through performance of a plurality of real-world activities;

a content suggestion module implemented using the processor and the memory, the content suggestion module configured to select suggested content from the context-sensitive content items in the content database, by operations that:

perform an ongoing assessment of behavior of the human subject to measure progress of the human subject towards achieving the health goal, by analysis of the input from the human subject provided collected in the assessment prompt to determine at least one particular user-relevant tag for tracking in the plurality of user-relevant tags, the at least one particular user-relevant tag determined based on relevancy of the tag to the ongoing assessment of behavior of the human subject;

select a particular activity of the plurality of real-world activities for performance by the human subject using the contextual user information maintained in the electronic information system, the particular activity being selected for the human subject based on whether the particular activity is associated with at least one of the plurality of user-relevant tags and whether the particular activity is likely to be performed by the human subject; and select content maintained in the electronic information system relevant to performance of the particular activity to encourage progress towards achieving the health goal, the content being selected from the electronic information system by using the contextual user information and the measured progress of the human subject, wherein the content is associated with the at least one particular user-relevant tag determined from the ongoing assessment;

a content delivery module implemented using the processor and the memory, the content delivery module configured to present the content relevant to achieving the health goal to the human subject, wherein a presentation style and a delivery type of presenting the content is performed using the contextual user information maintained in the electronic information system; and a conditions module implemented using the processor and the memory, the conditions module configured to control selection of the context-sensitive content items to match at least one data condition specified by the human subject;

a suggested action database implemented using the processor and the memory, the suggested action database configured to store suggested actions including the particular activity and additional activities for performance by the human subject;

a tagging database implemented using the processor and the memory, the tagging database configured to associate the tags with the suggested actions for performance by the human subject; and a playlist database implemented using the processor and the memory, the playlist database configured to store a playlist of the suggested actions for performance by the human subject;

a rules database implemented using the processor and the memory, the rules database configured to store rules related to selection of the context-sensitive content items and achievement of the particular activity by the human subject, wherein the rules are used by the content suggestion module to determine relevancy to the attainment of the overall goal by the human subject; and wherein the content suggestion module is configured to interface with the suggested action database, the tagging database, and the playlist database, to provide the suggested actions within a playlist to the human subject, based on characteristics associated with the human subject matching the tags associated with the suggested actions.

15. The system of claim 14, wherein the content suggestion module applies at least one filter and at least one weight to prioritize the particular activity in the playlist of the suggested actions.

16. A non-transitory machine-readable storage medium comprising a plurality of instructions that, in response to being executed on a computing device, cause the computing device to facilitate selection of content for a health goal from a client user from an electronic information system, with the plurality of instructions causing the computing device to:

obtain contextual user information maintained in the electronic information system relevant to the health goal for the client user, wherein progress towards achieving the health goal is obtained through performance of a plurality of real-world activities, wherein the contextual user information tracks a plurality of user-relevant tags associated with characteristics of the client user;

collect input in response to at least one natural language inquiry to the client user related to at least one prior activity of the plurality of real-world activities;

perform an ongoing assessment of behavior of the client user to measure progress of the client user towards achieving the health goal, by analyzing the input from the client user collected in the assessment prompt to determine at least one particular user-relevant tag for tracking in the plurality of user-relevant tags, the at least one particular user-relevant tag determined based on relevancy of the tag to the ongoing assessment of behavior of the client user;

select a particular activity of the plurality of real-world activities for performance by the client user using the contextual user information maintained in the electronic information system, the particular activity being selected for the client user based on whether the particular activity is associated with at least one of the plurality of user-relevant tags and whether the particular activity is likely to be performed by the client user;

select content maintained in the electronic information system relevant to performance of the particular activity to encourage progress towards achieving the health goal, the content being selected from the electronic information system by using the contextual user information and the measured progress of the client user, wherein the content is associated with the at least one particular user-relevant tag determined from the ongoing assessment; and generate a client content service interface for display within a graphical user interface accessible by the client user to present the content relevant to achieving the health goal to the client user, wherein a presentation style and a delivery type of presenting the content is performed using the contextual user information maintained in the electronic information system;

generate a supporter content service interface for display within a graphical user interface accessible by a supporter user to:
  indicate the progress of the client user towards the health goal;
  establish an interaction between the supporter user and the client user related to the health goal; and
  provide additional suggested content for inclusion with the content relevant to achieving the health goal.

17. The machine-readable storage medium of claim 16, wherein the client content service interface is provided by a first plurality of user interface components in a first internet-accessible application coupled to the information system, and wherein the supporter content service interface is provided by a second plurality of user interface components in a second internet-accessible application coupled to the information system.

18. The machine-readable storage medium of claim 16, the instructions further configured to cause the computing device to:
  facilitate a communication interface between the client content service interface and the supporter content service interface, the communication interface used to collect communications related to the goal from the supporter user and used to deliver the communications related to the goal to the client user, the communications occurring according to at least one communication preference of the client user;
  wherein the client user and the supporter user are connected via a social network, and wherein the communication interface is used to exchange the communications via the social network.

19. The machine-readable storage medium of claim 16, wherein the client content service interface and the supporter content service interface are coupled to the information system through an exchange of at least one message, and wherein the client content service interface and the supporter content service interface are provided with an internet-connected server used to generate and transmit the content to the client user and the supporter user respectively.

20. The machine-readable storage medium of claim 16, wherein the supporter content service interface for display within the graphical user interface accessible by the supporter user is further generated to:
  receive a selection of the suggested content related to the health goal to be provided to the client user, the suggested content being selected from a set of available suggested content items.

* * * * *

UNITED STATES PATENT AND TRADEMARK OFFICE
CERTIFICATE OF CORRECTION

| | | |
|---|---|---|
| PATENT NO. | : 9,171,048 B2 | Page 1 of 1 |
| APPLICATION NO. | : 13/772405 | |
| DATED | : October 27, 2015 | |
| INVENTOR(S) | : Brust et al. | |

It is certified that error appears in the above-identified patent and that said Letters Patent is hereby corrected as shown below:

In the specification,

In column 15, line 30, delete "play list." and insert --playlist.--, therefor

In column 15, line 34, delete "304," and insert --504,--, therefor

In column 27, line 9, delete "1322" and insert --1312--, therefor

Signed and Sealed this
Sixteenth Day of February, 2016

Michelle K. Lee
*Director of the United States Patent and Trademark Office*